US012635976B2

(12) United States Patent
Wegner

(10) Patent No.: US 12,635,976 B2
(45) Date of Patent: *May 26, 2026

(54) COHERENT SPREAD-SPECTRUM CODED WAVEFORMS IN SYNTHETIC APERTURE IMAGE FORMATION

(71) Applicant: Decision Sciences International Corporation, Poway, CA (US)

(72) Inventor: Allan Wegner, Del Mar, CA (US)

(73) Assignee: Decision Sciences International Corporation, Poway, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/903,890

(22) Filed: Oct. 1, 2024

(65) Prior Publication Data

US 2025/0261928 A1      Aug. 21, 2025

Related U.S. Application Data

(63) Continuation of application No. 18/177,649, filed on Mar. 2, 2023, now Pat. No. 12,121,394, which is a
(Continued)

(51) Int. Cl.
| | |
|---|---|
| *A61B 8/14* | (2006.01) |
| *A61B 8/00* | (2006.01) |
| *G01S 15/89* | (2006.01) |

(52) U.S. Cl.
CPC .............. *A61B 8/14* (2013.01); *A61B 8/4461* (2013.01); *A61B 8/4494* (2013.01);
(Continued)

(58) Field of Classification Search
CPC ....... A61B 8/14; A61B 8/4461; A61B 8/4494; A61B 8/4488; A61B 8/463; A61B 8/5223;
(Continued)

(56) References Cited

U.S. PATENT DOCUMENTS

| | | | |
|---|---|---|---|
| 4,105,018 A | 8/1978 | Greenleaf et al. |
| 4,110,755 A | 8/1978 | Zottl |

(Continued)

FOREIGN PATENT DOCUMENTS

| | | |
|---|---|---|
| AU | 2016233279 | 7/2019 |
| CA | 2427186 | 10/1999 |

(Continued)

OTHER PUBLICATIONS

Callow, H.J., "Signal Processing for Synthetic Aperture Sonar Image Enhancement," Thesis for Ph.D. in Electrical and Electronic Engineering at the University of Canterbury, Christchurch, New Zealand, 273 pages, Apr. 2003.

(Continued)

*Primary Examiner* — Peter Luong
(74) *Attorney, Agent, or Firm* — Perkins Coie LLP

(57) ABSTRACT

Techniques, systems, and devices are disclosed for synthetic aperture ultrasound imaging using spread-spectrum, wide instantaneous band, coherent, coded waveforms. In one aspect, a method includes synthesizing a composite waveform formed of a plurality of individual orthogonal coded waveforms that are mutually orthogonal to each other, correspond to different frequency bands and including a unique frequency with a corresponding phase; transmitting an acoustic wave based on the composite waveform toward a target from one or more transmitting positions; and receiving at one or more receiving positions acoustic energy returned from at least part of the target corresponding to the transmitted acoustic waveforms, in which the transmitting and receiving positions each include one or both of spatial positions of an array of transducer elements relative to the target and beam phase center positions of the array, and the transmitted acoustic waveforms and the returned acoustic waveforms produce an enlarged effective aperture.

14 Claims, 16 Drawing Sheets

Related U.S. Application Data continuation of application No. 17/395,057, filed on Aug. 5, 2021, now Pat. No. 11,607,192, which is a continuation of application No. 16/430,356, filed on Jun. 3, 2019, now Pat. No. 11,096,661, which is a continuation of application No. 15/804,955, filed on Nov. 6, 2017, now Pat. No. 10,321,889, which is a continuation of application No. 14/479,249, filed on Sep. 5, 2014, now Pat. No. 9,844,359.

(60) Provisional application No. 61/877,884, filed on Sep. 13, 2013.

(52) U.S. Cl.
CPC ...... *G01S 15/8913* (2013.01); *G01S 15/8915* (2013.01); *G01S 15/8927* (2013.01); *G01S 15/8959* (2013.01); *G01S 15/8997* (2013.01); *A61B 8/4488* (2013.01); *A61B 8/463* (2013.01); *A61B 8/5223* (2013.01); *A61B 8/54* (2013.01); *G01S 15/8945* (2013.01)

(58) Field of Classification Search
CPC ... A61B 8/54; G01S 15/8913; G01S 15/8915; G01S 15/8927; G01S 15/8959; G01S 15/8997; G01S 15/8945

See application file for complete search history.

(56) References Cited

U.S. PATENT DOCUMENTS

| | | | |
|---|---|---|---|
| 4,159,462 A | 6/1979 | Rocha et al. |
| 4,277,367 A | 7/1981 | Madsen et al. |
| 4,437,468 A | 3/1984 | Sorenson |
| 4,463,608 A | 8/1984 | Takeuchi et al. |
| 4,620,546 A | 11/1986 | Aida et al. |
| 4,821,206 A | 4/1989 | Arora |
| 4,830,015 A | 5/1989 | Okazaki |
| 4,888,746 A | 12/1989 | Wurster et al. |
| 5,005,418 A | 4/1991 | Anderson |
| 5,039,774 A | 8/1991 | Shikinami et al. |
| 5,107,837 A | 4/1992 | Ophir et al. |
| 5,181,513 A | 1/1993 | Touboul et al. |
| 5,241,964 A | 9/1993 | McQuilkin |
| 5,269,309 A | 12/1993 | Fort et al. |
| 5,284,143 A | 2/1994 | Rattner |
| 5,329,944 A | 7/1994 | Fabian et al. |
| 5,394,877 A | 3/1995 | Orr et al. |
| 5,417,218 A | 5/1995 | Spivey et al. |
| 5,445,144 A | 8/1995 | Wodicka et al. |
| 5,465,722 A | 11/1995 | Fort et al. |
| 5,522,878 A | 6/1996 | Montecalvo |
| 5,533,510 A | 7/1996 | Koch, III et al. |
| 5,608,690 A | 3/1997 | Hossack et al. |
| 5,623,928 A | 4/1997 | Wright et al. |
| 5,682,886 A | 11/1997 | Delp et al. |
| 5,793,701 A | 8/1998 | Wright et al. |
| 5,800,356 A | 9/1998 | Criton et al. |
| 5,803,089 A | 9/1998 | Ferre et al. |
| 5,806,518 A | 9/1998 | Mittelstadt |
| 5,829,444 A | 11/1998 | Ferre et al. |
| 5,868,676 A | 2/1999 | McCabe et al. |
| 5,873,830 A | 2/1999 | Hossack et al. |
| 5,882,557 A | 3/1999 | Hayakawa et al. |
| 5,902,244 A | 5/1999 | Kobayashi et al. |
| 5,913,823 A | 6/1999 | Hedberg et al. |
| 5,967,980 A | 10/1999 | Ferre et al. |
| 6,016,285 A | 1/2000 | Wright et al. |
| 6,039,694 A | 3/2000 | Larson |
| 6,045,507 A | 4/2000 | Muzilla et al. |
| 6,050,945 A | 4/2000 | Peterson et al. |
| 6,083,164 A | 7/2000 | Oppelt et al. |
| 6,106,464 A | 8/2000 | Bass et al. |
| 6,110,114 A | 8/2000 | Nock et al. |
| 6,113,544 A | 9/2000 | Mo |
| 6,123,669 A | 9/2000 | Kanda |
| 6,132,375 A | 10/2000 | Napolitano |
| 6,157,592 A | 12/2000 | Kriz et al. |
| 6,205,411 B1 | 3/2001 | DiGioia, III et al. |
| 6,231,834 B1 | 5/2001 | Unger et al. |
| 6,241,676 B1 | 6/2001 | Savord |
| 6,322,567 B1 | 11/2001 | Mittelstadt et al. |
| 6,338,765 B1 | 1/2002 | Statnikov |
| 6,340,363 B1 | 1/2002 | Bolger et al. |
| 6,341,231 B1 | 1/2002 | Ferre et al. |
| 6,402,707 B1 | 6/2002 | Ernst |
| 6,425,865 B1 | 7/2002 | Salcudean et al. |
| 6,436,045 B1 | 8/2002 | Rafter et al. |
| 6,445,943 B1 | 9/2002 | Ferre et al. |
| 6,508,766 B2 | 1/2003 | Sato et al. |
| 6,537,216 B1 | 3/2003 | Shifrin |
| 6,583,392 B2 | 6/2003 | Hershey et al. |
| 6,585,648 B1 | 7/2003 | Robinson |
| 6,620,101 B2 | 9/2003 | Azzam et al. |
| 6,626,916 B1 | 9/2003 | Yeung et al. |
| 6,652,461 B1 | 11/2003 | Levkovitz |
| 6,687,531 B1 | 2/2004 | Ferre et al. |
| 6,725,082 B2 | 4/2004 | Sati et al. |
| 6,736,780 B2 | 5/2004 | Song et al. |
| 6,757,582 B2 | 6/2004 | Brisson et al. |
| 6,785,571 B2 | 8/2004 | Glossop |
| 6,786,097 B2 | 9/2004 | Song et al. |
| 6,796,988 B2 | 9/2004 | Melkent et al. |
| 6,808,494 B2 | 10/2004 | Shifrin |
| 6,843,957 B2 | 1/2005 | Statnikov |
| 6,918,877 B2 | 7/2005 | Hossack et al. |
| 6,934,575 B2 | 8/2005 | Ferre et al. |
| 6,939,300 B2 | 9/2005 | Petersen et al. |
| 6,960,173 B2 | 11/2005 | Babaev |
| 7,004,906 B1 | 2/2006 | Guracar et al. |
| 7,066,886 B2 | 6/2006 | Song et al. |
| 7,070,565 B2 | 7/2006 | Vaezy |
| 7,207,939 B2 | 4/2007 | Husher |
| 7,226,456 B2 | 6/2007 | O'Neil et al. |
| 7,291,119 B1 | 11/2007 | de Guise et al. |
| 7,319,641 B2 | 1/2008 | Goudie |
| 7,344,609 B2 | 3/2008 | Statnikov |
| 7,395,181 B2 | 7/2008 | Foxlin |
| 7,473,250 B2 | 1/2009 | Makin et al. |
| 7,532,201 B2 | 5/2009 | Quistgaard et al. |
| 7,542,790 B2 | 6/2009 | Jensen et al. |
| 7,566,304 B2 | 7/2009 | Nakamura et al. |
| 7,601,966 B2 | 10/2009 | Ben-haim |
| 7,678,049 B2 | 3/2010 | Tsoref et al. |
| 7,719,515 B2 | 5/2010 | Fujiwara et al. |
| 7,719,689 B2 | 5/2010 | Lee et al. |
| 7,728,487 B2 | 6/2010 | Adachi et al. |
| 7,763,035 B2 | 7/2010 | Melkent et al. |
| 7,798,585 B2 | 9/2010 | Oguri |
| 7,806,823 B2 | 10/2010 | Sakai et al. |
| 7,826,889 B2 | 11/2010 | David et al. |
| 7,835,778 B2 | 11/2010 | Foley et al. |
| 7,835,784 B2 | 11/2010 | Mire et al. |
| 7,837,625 B2 | 11/2010 | Abe |
| RE42,194 E | 3/2011 | Foley et al. |
| 7,905,836 B2 | 3/2011 | Dan |
| 7,917,317 B2 | 3/2011 | McKeon |
| 7,938,777 B2 | 5/2011 | Amiot et al. |
| 7,938,778 B2 | 5/2011 | Sakai |
| 7,963,919 B2 | 6/2011 | Proulx |
| 7,982,362 B2 | 7/2011 | Adachi et al. |
| 8,002,705 B1 | 8/2011 | Napolitano et al. |
| 8,038,616 B2 | 10/2011 | Angelsen et al. |
| 8,043,220 B2 | 10/2011 | Okada et al. |
| 8,103,461 B2 | 1/2012 | Glaser et al. |
| 8,105,339 B2 | 1/2012 | Melkent et al. |
| 8,126,533 B2 | 2/2012 | Lavallee |
| 8,147,409 B2 | 4/2012 | Shifrin |
| 8,152,726 B2 | 4/2012 | Amiot et al. |
| 8,165,658 B2 | 4/2012 | Waynik et al. |
| 8,241,217 B2 | 8/2012 | Chiang et al. |
| 8,251,908 B2 | 8/2012 | Vortman et al. |
| 8,253,578 B2 | 8/2012 | Watabe et al. |

(56)　　　　References Cited

U.S. PATENT DOCUMENTS

| | | |
|---|---|---|
| 8,311,611 B2 | 11/2012 | Csavoy et al. |
| 8,323,200 B2 | 12/2012 | Kunita |
| 8,372,070 B2 | 2/2013 | Tanaka et al. |
| 8,374,674 B2 | 2/2013 | Gertner |
| 8,409,099 B2 | 4/2013 | Vitek et al. |
| 8,409,103 B2 | 4/2013 | Grunwald et al. |
| 8,444,564 B2 | 5/2013 | Mahfouz et al. |
| 8,447,388 B2 | 5/2013 | Igarashi |
| 8,491,476 B2 | 7/2013 | Iwama et al. |
| 8,556,834 B2 | 10/2013 | Gertner |
| 8,565,860 B2 | 10/2013 | Kimchy et al. |
| 8,626,267 B2 | 1/2014 | Lavallee |
| 8,675,939 B2 | 3/2014 | Moctezuma de la Barrera |
| 8,771,188 B2 | 7/2014 | Schers et al. |
| 8,774,900 B2 | 7/2014 | Buly et al. |
| 8,814,810 B2 | 8/2014 | Roche et al. |
| 8,864,686 B2 | 10/2014 | Roche et al. |
| 8,880,152 B2 | 11/2014 | Lavallee |
| 8,909,325 B2 | 12/2014 | Kimchy et al. |
| 8,939,909 B2 | 1/2015 | Wegner |
| 9,060,794 B2 | 6/2015 | Kang et al. |
| 9,101,394 B2 | 8/2015 | Arata et al. |
| 9,174,065 B2 | 11/2015 | Gertner |
| 9,196,046 B2 | 11/2015 | Meyer |
| 9,220,571 B2 | 12/2015 | Lavallee |
| 9,244,169 B2 | 1/2016 | Fan et al. |
| 9,248,001 B2 | 2/2016 | Colombet et al. |
| 9,352,171 B2 | 5/2016 | Gertner |
| 9,387,276 B2 | 7/2016 | Sun et al. |
| 9,420,999 B2 | 8/2016 | Wegner |
| 9,503,201 B2 | 11/2016 | Saulnier |
| 9,572,548 B2 | 2/2017 | Moctezuma de la Barrera |
| 9,597,058 B2 | 3/2017 | Kanayama et al. |
| 9,844,359 B2 | 12/2017 | Wegner |
| 9,872,667 B2 | 1/2018 | Wegner |
| 9,878,506 B2 | 1/2018 | Zhao et al. |
| 10,085,722 B2 | 10/2018 | Wegner |
| 10,321,889 B2 | 6/2019 | Wegner |
| 10,426,429 B2 | 10/2019 | Kruse et al. |
| 10,743,838 B2 | 8/2020 | Freiburg et al. |
| 10,993,699 B2 | 5/2021 | Wegner |
| 11,096,661 B2 | 8/2021 | Wegner |
| 11,154,274 B2 | 10/2021 | Wegner |
| 11,191,521 B2 | 12/2021 | Freiburg et al. |
| 11,520,043 B2 | 12/2022 | Kruse |
| 11,596,388 B2 | 3/2023 | Wegner |
| 11,607,192 B2 | 3/2023 | Wegner |
| 11,737,726 B2 | 8/2023 | Kruse et al. |
| 11,839,512 B2 | 12/2023 | Freiburg et al. |
| 11,860,273 B2 | 1/2024 | Kruse |
| 11,957,516 B2 | 4/2024 | Wegner |
| 12,121,394 B2 | 10/2024 | Wegner |
| 12,251,259 B2 | 3/2025 | Freiburg et al. |
| 2002/0068871 A1 | 6/2002 | Mendlein et al. |
| 2002/0099290 A1 | 7/2002 | Haddad |
| 2002/0122536 A1 | 9/2002 | Kerrien et al. |
| 2002/0188198 A1 | 12/2002 | Hong |
| 2002/0188229 A1 | 12/2002 | Ryaby et al. |
| 2003/0036702 A1 | 2/2003 | Davidsen |
| 2003/0125628 A1 | 7/2003 | Song et al. |
| 2004/0066708 A1 | 4/2004 | Ogawa |
| 2004/0236223 A1 | 11/2004 | Barnes et al. |
| 2005/0004465 A1 | 1/2005 | Abuhamad |
| 2005/0101861 A1 | 5/2005 | Satoh |
| 2005/0101867 A1 | 5/2005 | Johnson et al. |
| 2005/0113698 A1 | 5/2005 | Kristoffersen |
| 2005/0154302 A1 | 7/2005 | Sela et al. |
| 2005/0203399 A1 | 9/2005 | Vaezy |
| 2005/0215893 A1 | 9/2005 | Barnes et al. |
| 2006/0004290 A1 | 1/2006 | Smith et al. |
| 2006/0119223 A1 | 6/2006 | Ossmann |
| 2006/0173305 A1 | 8/2006 | Asafusa et al. |
| 2007/0066897 A1 | 3/2007 | Sekins et al. |
| 2007/0156050 A1 | 7/2007 | Barnes et al. |
| 2007/0167752 A1 | 7/2007 | Proulx |

| | | |
|---|---|---|
| 2007/0226976 A1 | 10/2007 | Zipparo et al. |
| 2007/0239001 A1 | 10/2007 | Mehi et al. |
| 2007/0239002 A1 | 10/2007 | Alam |
| 2007/0265690 A1 | 11/2007 | Lichtenstein et al. |
| 2007/0276238 A1 | 11/2007 | Sudol |
| 2008/0110263 A1 | 5/2008 | Klessel et al. |
| 2008/0119737 A1 | 5/2008 | Urbano et al. |
| 2008/0200810 A1 | 8/2008 | Buchalter |
| 2008/0208055 A1 | 8/2008 | Bertram et al. |
| 2008/0262347 A1 | 10/2008 | Batchelder et al. |
| 2008/0281202 A1 | 11/2008 | Fraser et al. |
| 2008/0281237 A1 | 11/2008 | Slayton et al. |
| 2009/0030312 A1 | 1/2009 | Hadjicostis |
| 2009/0043206 A1 | 2/2009 | Towfiq et al. |
| 2009/0093737 A1 | 4/2009 | Chomas |
| 2009/0124871 A1 | 5/2009 | Arshak et al. |
| 2009/0306497 A1 | 12/2009 | Manzke et al. |
| 2010/0179425 A1 | 7/2010 | Zadicario |
| 2010/0204577 A1 | 8/2010 | Sekins et al. |
| 2010/0268072 A1 | 10/2010 | Hall et al. |
| 2010/0274139 A1 | 10/2010 | Fukukita et al. |
| 2010/0280379 A1 | 11/2010 | Satoh |
| 2010/0286518 A1 | 11/2010 | Lee et al. |
| 2010/0286527 A1 | 11/2010 | Cannon |
| 2011/0008437 A1 | 1/2011 | Altman |
| 2011/0060226 A1 | 3/2011 | Yen et al. |
| 2011/0092862 A1 | 4/2011 | Chivers |
| 2011/0264012 A1 | 10/2011 | Lautzenhiser et al. |
| 2012/0029345 A1 | 2/2012 | Mahfouz et al. |
| 2012/0087564 A1 | 4/2012 | Tsujita |
| 2012/0238875 A1 | 9/2012 | Savitsky et al. |
| 2012/0281507 A1 | 11/2012 | Rikoski |
| 2013/0060121 A1 | 3/2013 | Patwardhan et al. |
| 2013/0144135 A1 | 6/2013 | Mahfouz et al. |
| 2013/0144166 A1 | 6/2013 | Specht et al. |
| 2013/0150863 A1 | 6/2013 | Baumgartner |
| 2013/0165005 A1 | 6/2013 | Berard-Andersen et al. |
| 2013/0218013 A1 | 8/2013 | Barthe et al. |
| 2014/0163377 A1 | 6/2014 | Kang et al. |
| 2014/0180116 A1 | 6/2014 | Lindekugel et al. |
| 2015/0018682 A1 | 1/2015 | Schers et al. |
| 2015/0038613 A1 | 2/2015 | Sun et al. |
| 2015/0088040 A1 | 3/2015 | Barthe et al. |
| 2015/0133788 A1 | 5/2015 | Mauldin, Jr. et al. |
| 2015/0164467 A1 | 6/2015 | Suetoshi et al. |
| 2015/0182191 A1 | 7/2015 | Caluser et al. |
| 2015/0313572 A1 | 11/2015 | Gerbaulet et al. |
| 2016/0000409 A1 | 1/2016 | Bruder et al. |
| 2016/0100821 A1 | 4/2016 | Eggers et al. |
| 2016/0270763 A1 | 9/2016 | Hayes et al. |
| 2018/0126677 A1 | 5/2018 | Zhao et al. |
| 2020/0284902 A1 | 9/2020 | Kruse |
| 2020/0337674 A1 | 10/2020 | Wegner |
| 2021/0361259 A1 | 11/2021 | Wegner |
| 2022/0155440 A1 | 5/2022 | Kruse |
| 2023/0052016 A1 | 2/2023 | Kruse |
| 2023/0089137 A1 | 3/2023 | Kruse |
| 2024/0090867 A1 | 3/2024 | Kruse et al. |
| 2025/0090140 A1 | 3/2025 | Wegner |

FOREIGN PATENT DOCUMENTS

| | | |
|---|---|---|
| CA | 2852801 | 4/2006 |
| CA | 3001315 | 6/2007 |
| CA | 3080561 | 11/2007 |
| CN | 102258399 | 5/2001 |
| CN | 100354651 | 8/2008 |
| CN | 101325913 | 3/2009 |
| CN | 104169739 | 1/2011 |
| CN | 107530061 | 5/2013 |
| CN | 116685847 | 5/2019 |
| CN | 108366775 | 12/2023 |
| EP | 1707124 | 4/1980 |
| EP | 1795917 | 11/1983 |
| EP | 1854406 | 3/1985 |
| EP | 1955668 | 5/1987 |
| EP | 952461 | 2/1996 |
| EP | 2033579 | 12/2007 |
| GB | 2472066 | 12/2008 |

(56) References Cited

FOREIGN PATENT DOCUMENTS

| | | |
|---|---|---|
| IL | 232148 | 11/2012 |
| JP | 62117535 | 2/2000 |
| JP | 2000041980 | 6/2000 |
| JP | 2000166922 | 10/2000 |
| JP | 2000287988 | 3/2002 |
| JP | 2003190157 | 7/2003 |
| JP | 2004147852 | 5/2004 |
| JP | 2005152608 | 6/2005 |
| JP | 2005527336 | 9/2005 |
| JP | 2007152127 | 3/2007 |
| JP | 2010082425 | 6/2007 |
| JP | 2011062531 | 6/2007 |
| JP | 2011177461 | 1/2009 |
| JP | 2012002586 | 2/2009 |
| JP | 2013056156 | 5/2009 |
| JP | 2013520235 | 4/2010 |
| JP | 2013539715 | 3/2011 |
| JP | 2014533154 | 9/2011 |
| JP | 2004147852 A | 1/2012 |
| JP | 55051351 A | 3/2013 |
| JP | 58195550 A | 5/2013 |
| JP | 2014103512 | 6/2013 |
| JP | 60048736 A | 7/2013 |
| JP | 8038473 | 11/2014 |
| WO | 2019084526 | 4/1980 |
| WO | 2020219705 | 11/1983 |
| WO | 2022104230 | 3/1985 |
| WO | 2018061025 | 5/2004 |
| WO | 2002024094 | 10/2013 |
| WO | 2007069156 | 8/2014 |
| WO | 2009009064 | 9/2014 |
| WO | 2009020617 | 9/2014 |
| WO | 2009063421 | 11/2014 |
| WO | 2013066821 | 12/2014 |
| WO | 2013103956 | 3/2015 |
| WO | 2014128593 | 3/2016 |
| WO | 2014150780 | 9/2016 |
| WO | 2014150961 | 9/2016 |
| WO | 2007023477 | 1/2017 |
| WO | 2014186904 | 11/2017 |
| WO | 2015038554 | 4/2018 |
| WO | 2016044830 | 5/2019 |
| WO | 2016138257 | 10/2020 |
| WO | 2016149427 | 5/2022 |

OTHER PUBLICATIONS

Cao, Z et al., "Fabrication and properties of thermosensitive organic/inorganic hybrid hydrogel thin films," Langmuir, American Chemical Society, vol. 24, No. 10, May 20, 2008, pp. 5543-5551.

Chiao, R., "Coded Excitation for Diagnostic Ultrasound: A System Developer's Perspective," *IEEE Transactions on Ultrasonics, Ferroelectrics, and Frequency Control*, 52(2):160-170, Feb. 2005.

Choe, J.W., et al., "Volumetric real-time imaging using a CMUT ring array," IEEE Transactions on Ultrasonics, Ferroelectrics, and Frequency Control, 59(6):1201-1211, Jun. 2012.

Demi, L., et al., "In Vitro and In Vivo Tissue Harmonic Images Obtained With Parallel Transmit Beamforming by Means of Orthogonal Frequency Division Multiplexing," IEEE Transactions on Ultrasonics, Ferroelectrics, and Frequency Control, 62(1):230-235, Jan. 2015.

European Search Report mailed on Apr. 19, 2017 for European Application No. 14844538.0, filed on Sep. 9, 2014 (10 pages).

European Search Report mailed on Feb. 1, 2019 for European Application No. 16756353.5, filed on Feb. 25, 2016 (14 pages).

European Search Report mailed on Jun. 29, 2015 for European Application No. 12845256.2, filed on Oct. 29, 2012 (8 pages).

European Search Report mailed on Nov. 9, 2018 for European Application No. 16765701.4, filed on Mar. 16, 2016 (6 pages).

Exam Report mailed on Feb. 26, 2019 for Singapore Application No. 11201706953Y, filed on Feb. 25, 2016 (6 pages).

Examination Report mailed Aug. 9, 2022 for European Patent Application No. 16854507.7, 8 pages.

Examination Report mailed Dec. 21, 2022 in Canadian Patent Application No. 3,001,315, 4 pages.

Examination Report mailed Oct. 4, 2022 in European Patent Application No. 14844538.0, 4 pages.

Examination Report mailed on Dec. 20, 2019 for Europe Patent Application No. 14844538.0, filed on Sep. 9, 2014 (7 pages).

Examination Report mailed on Jul. 19, 2021 for European Application No. 12845256.2, filed on Oct. 29, 2012 (8 pages).

Examination Report mailed on Jul. 26, 2018 for Canada Patent Application No. 2,852,801, filed on Oct. 29, 2012, 4 pages.

Examination Report mailed on Jun. 22, 2020 for Australian Application No. 2016334258, 4 pages.

Examination Report mailed on Mar. 16, 2018 for European Application No. 12845256.2, filed on Oct. 29, 2012 (8 pages).

Extended European Search Report mailed on Feb. 15, 2019 for European Application No. 16765701.4, filed on Mar. 16, 2016 (14 pages).

Extended European Search Report mailed on Jul. 2, 2019 for European Application No. 16756353.5, filed on Feb. 25, 2016 (14 pages).

Extended European Search Report mailed on Jun. 18, 2019 for European Application No. 16854507.7, filed on Oct. 7, 2016 (11 pages).

First Examination Report mailed Apr. 12, 2016 for Australian Patent Application No. 2012332817, filed on Oct. 29, 2012, 3 pages.

First Examination Report mailed Dec. 7, 2018 for Australian Patent Application No. 2018203912, filed on Sep. 9, 2014, 2 pages.

First Examination Report mailed Nov. 21, 2018 for Australian Patent Application No. 2018203785, filed on Oct. 29, 2012, 2 pages.

First Office Action mailed Aug. 14, 2020 for Chinese Patent Application No. 201680071645.1, with English translation, 35 pages.

Hunter, A.J., et al., "A Comparison of Fast Factorised Back-Projection and Wavenumber Algorithms for SAS Image Reconstruction," Proceedings of the World Congress on Ultrasonics, 4 pages, (2003).

International Search Report and Written Opinion mailed on Dec. 29, 2016 for International Application No. PCT/US2016/056159, filed on Oct. 7, 2016 (7 pages).

International Search Report and Written Opinion mailed on Jul. 6, 2016 for International Application No. PCT/US2016/019554, filed on Feb. 25, 2016 (12 pages).

International Search Report and Written Opinion mailed on Mar. 3, 2015 for International Application No. PCT/US2014/054855, filed on Sep. 9, 2014 (11 pages).

International Search Report and Written Opinion mailed on May 15, 2013 for International Application No. PCT/US2012/062435, filed on Oct. 29, 2012 (9 pages).

Ito, T., et al., "Evaluation of Acoustic Imaging System Using Correlation Division in Synthetic Transmit Aperture with Multicarrier Signals," IEICE Transactions on Fundamentals of Electronics, Communications and Computer Sciences, E94-A(10):1907-1919, Oct. 2011.

Jensen, J.A., et al., "Synthetic Aperture Ultrasound Imaging," Ultrasonics, 44(Suppl 1):e5-e15, Dec. 2006.

Koch, A., et al., "An Ultrasound Tomography System With Polyvinyl Alcohol (PVA) Moldings for Coupling: In Vivo Results for 3-D Pulse-Echo Imaging of the Female Breast," IEEE Transactions on Ultrasonics, Ferroelectrics, and Frequency Control, 62(2):266-279, Feb. 2015.

Kundur, D., et al., "A Novel Blind Deconvolution Scheme for Image Restoration Using Recursive Filtering," IEEE Transactions on Signal Processing, 46(2):375-390, Feb. 1998.

Lockwood et al., "Real-Time 3-D Ultrasound Imaging Using Sparse Synthetic Aperture Beamforming." 1998, IEEE Transactions on Ultrasonics, ferroelectrics, and frequency control, vol. 45, No. 4.

Misaridis, T., "Use of Modulated Excitation Signals in Medical Ultrasound. Part I: Basic Concepts and Expected Benefits," *IEEE Transactions on Ultrasonics, Ferroelectrics, and Frequency Control*, 52(2):177-191, Feb. 2005.

(56) References Cited

OTHER PUBLICATIONS

Misaridis, T., "Use of Modulated Excitation Signals in Medical Ultrasound. Part II: Design and Performance for Medical Imaging Applications," *IEEE Transactions on Ultrasonics, Ferroelectrics, and Frequency Control*, 52(2):192-207, Feb. 2005.

Misaridis, T., "Use of Modulated Excitation Signals in Medical Ultrasound. Part III: High Frame Rate Imaging," *IEEE Transactions on Ultrasonics, Ferroelectrics, and Frequency Control*, 52(2):208-219, Feb. 2005.

Notice of Final Rejection mailed Feb. 23, 2023 for Korean Patent Application No. 10-2017-7027091, with English Translation, 13 pages.

Notice of Preliminary Rejection mailed Jul. 28, 2022 for Korean Patent Application No. 10-2017-7027091, 22 pages.

Notice of Preliminary Rejection mailed Jul. 28, 2023 for Korean Patent Application No. 10-2018-7012592, English Translation, 2 pages.

Notice of Requisition mailed Aug. 20, 2024 in Canadian Patent Application No. 2,977,975, 4 pages.

Notice of Requisition mailed Mar. 10, 2023 in Canadian Patent Application No. 2,977,975, 4 pages.

Notification of Defects mailed Nov. 22, 2017 for Israel Patent Application No. 232148, filed on Oct. 29, 2012, 4 pages.

O'Donnell, M., "Coded Excitation for Synthetic Aperture Ultrasound Imaging," *IEEE Transactions on Ultrasonics, Ferroelectrics, and Frequency Control*, 52(2):171-176, Feb. 2005.

Office Action mailed Aug. 30, 2020 for Israel Application No. 264906, filed on Oct. 29, 2012, with English translation, 10 pages.

Office Action mailed Jan. 13, 2020 for Chinese Application No. 201680028663.1, filed on Mar. 16, 2016 (17 pages).

Office Action mailed Jan. 14, 2020 for Japanese Application No. 2017-563504, filed on Feb. 25, 2016 (14 pages).

Office Action mailed Jun. 3, 2021 for Israel Application No. 258533, 7 pages, with English Translation.

Office Action mailed Jun. 4, 2019 for Japanese Application No. 2017-187288, filed on Oct. 29, 2012 (3 pages).

Office Action mailed Mar. 17, 2020 for Japanese Application No. 2018-145683, filed on Sep. 9, 2014 (4 pages).

Office Action mailed Mar. 25, 2020 for Japanese Application No. 2016-542050, filed on Sep. 9, 2014 (4 pages).

Office Action mailed Oct. 20, 2020 for Canadian Application No. 2,923,861, 4 pages.

Office Action mailed Oct. 29, 2019 for Japanese Application No. 2018-145683, filed on Sep. 9, 2014 (3 pages).

Office Action mailed Oct. 29, 2021 in Chinese Patent Application No. 201680071645.1, with English translation, 28 pages.

Office Action mailed Oct. 7, 2021 in Israel Patent Application No. 254158, 6 pages, with English translation.

Office Action mailed on Dec. 4, 2019 for Chinese Application No. 201680023999.9, filed on Feb. 25, 2016 (23 pages).

Office Action mailed on Feb. 25, 2020 for Japanese Application No. 2017-549178, filed on Mar. 16, 2016 (8 pages).

Office Action mailed on Jul. 3, 2018 for Japanese Application No. 2017-187288, filed on Oct. 29, 2012 (6 pages).

Office Action mailed on Jun. 11, 2019 for Japanese Application No. 2016-542050, filed on Sep. 9, 2014 (15 pages).

Office Action mailed on Jun. 18, 2019 for Japanese Patent Application No. 2018-145683, filed on Sep. 9, 2014, 12 pages.

Office Action mailed on Jun. 5, 2018 for Chinese Patent Application No. 201480062224.3, filed on Sep. 9, 2014, 13 pages.

Office Action mailed on Sep. 13, 2016 for Japanese Application No. 2014-539114, filed on Oct. 29, 2012 (4 pages).

Office Action mailed on Sep. 19, 2017 for Japanese Application No. 2016-542050, filed on Sep. 9, 2014 (15 pages).

Office Action mailed on Sep. 2, 2015 for Chinese Application No. 201280065031.4, filed on Oct. 29, 2012 (26 pages).

Office Action mailed Sep. 23, 2020 for Israel Application No. 254158, filed Feb. 25, 2016, english translation, 3 pages.

Prokop A F et al., "Polyacrylamide gel as an acoustic coupling medium for focused ultrasound therapy." Ultrasound in Medicine and Biol, New York, NY, US, vol. 29, No. 9, Sep. 1, 2003, pp. 1351-1358.

Rui Silva, S., et al., "2 Synthetic Aperture Techniques for Sonar Systems," Advances in Sonar Technology, edited by Sergio Rui Silva, publisher I-Tech Education and Publishing, ISBN 978-3-902613-48-6, pp. 15-42, Feb. 2009.

Second Office Action mailed Jul. 14, 2020 for Chinese Patent Application No. 201680023999.9, filed on Feb. 25, 2016, 41 pages, with English translation.

Second Office Action mailed Jul. 20, 2016 for Chinese Patent Application No. 201280065031.4, filed on Oct. 29, 2012 (26 pages).

Second Office Action mailed Jun. 1, 2021 for Chinese Patent Application No. 201680071645.1, with English translation, 32 pages.

Singapore Search Report mailed on Sep. 24, 2018 for Singapore Application No. 11201706953Y, filed on Feb. 25, 2016 (13 pages).

Singapore Written Opinion mailed on Jul. 10, 2017 for Singapore Application No. 11201601906P, filed on Sep. 9, 2014 (8 pages).

Singapore Written Opinion mailed on Jun. 21, 2018 for Singapore Application No. 11201707641P, filed on Mar. 16, 2016 (8 pages).

Singapore Written Opinion mailed on Mar. 11, 2020 for Singapore Application No. 11201707641P, filed on Mar. 16, 2016 (8 pages).

Trots, I. et al., "Synthetic Aperture Method in Ultrasound Imaging," Chapter 3 of Ultrasound Imaging, edited by Masayuki Tanabe, 2011, pp. 37-56.

Zhu, S., et al., "SAS Autofocus Based on Phase Gradient Autofocus," IEEE 2011 Fourth International Workshop on Chaos-Fractals Theories and Applications (IWCFTA), pp. 298-301, Oct. 19-22, 2011.

Real Aperture Beam

Desired Resolution Cell

135

131a

131b

*Phase Center 1*

131n

Array 130

Sub 1 Sub 2 ••• Sub N

Position 1
(beam phase
center position)

135

131a

131b

*Phase Center 2*

131n

Array 130

Sub 1 Sub 2 ••• Sub N

Position 2
(beam phase
center position)

Transducer Array (211)

600

Received echo
data sampled at
each position

610

Store Data in Digial Memory

620

Perform Axial Range Compression

630

SA Image Formation

640

Image Processing

COHERENT SPREAD-SPECTRUM CODED WAVEFORMS IN SYNTHETIC APERTURE IMAGE FORMATION

CROSS REFERENCE TO RELATED APPLICATIONS

This patent document is a continuation of U.S. patent application Ser. No. 18/177,649, filed on Mar. 2, 2023, which is a continuation of U.S. patent application Ser. No. 17/395,057, filed on Aug. 5, 2021, now U.S. Pat. No. 11,607,192, which is a continuation of U.S. patent application Ser. No. 16/430,356, filed on Jun. 3, 2019, now U.S. Pat. No. 11,096,661, which is a continuation of U.S. patent application Ser. No. 15/804,955, filed on Nov. 6, 2017, now U.S. Pat. No. 10,321,889, which is a continuation of U.S. patent application Ser. No. 14/479,249, filed on Sep. 5, 2014, now U.S. Pat. No. 9,844,359, which claims the benefit of priority of U.S. Provisional Patent Application No. 61/877,884, filed on Sep. 13, 2013. The entire contents of the before-mentioned patent applications are incorporated by reference as part of the disclosure of this application.

TECHNICAL FIELD

This patent document relates to acoustic image formation.

BACKGROUND

Acoustic imaging is an imaging modality that employs the properties of sound waves traveling through a medium to render a visual image. High frequency acoustic imaging has been used as an imaging modality for decades in a variety of biomedical fields to view internal structures and functions of animals and humans. High frequency acoustic waves used in biomedical imaging may operate in different frequencies, e.g., between 1 and 20 MHz, or even higher frequencies, and are often termed ultrasound waves. Some factors, including inadequate spatial resolution and tissue differentiation, can lead to less than desirable image quality using conventional techniques of ultrasound imaging, which can limit its use for many clinical indications or applications.

SUMMARY

Techniques, systems, and devices are disclosed for synthetic aperture ultrasound imaging using coherent, spread-spectrum, instantaneous wideband, frequency- and/or phase-coded acoustic waveforms. The disclosed techniques, systems, and devices can be used to form one-dimensional (1D), two-dimensional (2D), and/or three-dimensional (3D) ultrasound images of biological tissue.

The subject matter described in this patent document can provide one or more of the following features and can be used in many applications. For example, the disclosed technology can be used during routine primary care screenings to identify and locate early-stage pathologies including malignancies, as well as later stage cancers, which can potentially raise survival rates of hard-to-diagnose asymptomatic patients. The disclosed technology can be used by board-certified radiologists to diagnose neoplasms as benign or malignant prior to any surgical biopsy or resection intervention, which may also improve patient survival rate while reducing unnecessary biopsies. The disclosed technology, when integrated with a fine needle biopsy instrument, can be used in medical procedures to confirm noninvasive diagnoses, which can reduce the level of invasiveness of such biopsy procedures. The disclosed technology, when integrated pre-operatively with Computed Tomography (CT) x-ray images and/or intra-operatively with minimally invasive surgical high definition video instrumentation, can fuse CT, optical and ultrasound images, and thereby can further give surgeons added abilities to locate, diagnose, and surgically excise or repair diseased tissue without damaging healthy tissue. The disclosed technology, when integrated with specialized surgical instrumentation, can fuse ultrasound images with other data, and can give surgeons added abilities to locate and manipulate anatomic areas of interest while minimizing unnecessary damage to nearby structures. The disclosed technology can reduce the amount of time for the brachytherapy treatment of malignant neoplasms, for example, by precisely guiding the insertion of sealed radioactive sources and catheters into the proper location. Similarly, the disclosed technology can aid insertion of high-dose, localized pharmaceuticals for treatments of diseases.

DETAILED DESCRIPTION

Ultrasound imaging can be performed by emitting an acoustic waveform (pulse) within a physical elastic medium, which is partly reflected from a boundary between two mediums (e.g., biological tissue structures) and partially transmitted. The reflection depends on the acoustic impedance difference between the two mediums (e.g., at the interface between two different biological tissue types). For example, some of the acoustic energy of the transmitted acoustic waveform can be scattered back to the transducer at the interface to be received, and processed to extract information, while the remainder may travel on and to the next medium. In some instances, scattering of the reflection may occur as the result of two or more impedances contained in the reflective medium acting as a scattering center. Additionally, for example, the acoustic energy can be refracted, diffracted, delayed, and/or attenuated based on the properties of the medium and/or the nature of the acoustic wave.

In some existing ultrasound imaging systems, a typical transducer may employ an array of piezoelectric elements to transmit an ultrasound pulse toward a target region (e.g., of a body of an organism) and receive the returned ultrasound signals (echoes) that return from scattering structures within. This transducer array functions as the aperture of the imaging system. Ultrasound pulses can be electronically steered and focused as a sequence pulses through a plane or volume and used to produce a 1D, 2D and/or 3D map of the returned echoes used to form an image of the target. Processes of steering and focusing ultrasound pulses is referred to as beamforming. In some examples, the ultrasound pulse and the returned echoes transmitted and received at the transducer array can be individually delayed in time at each transducer of the array to act as a phased array.

Figure 1A:
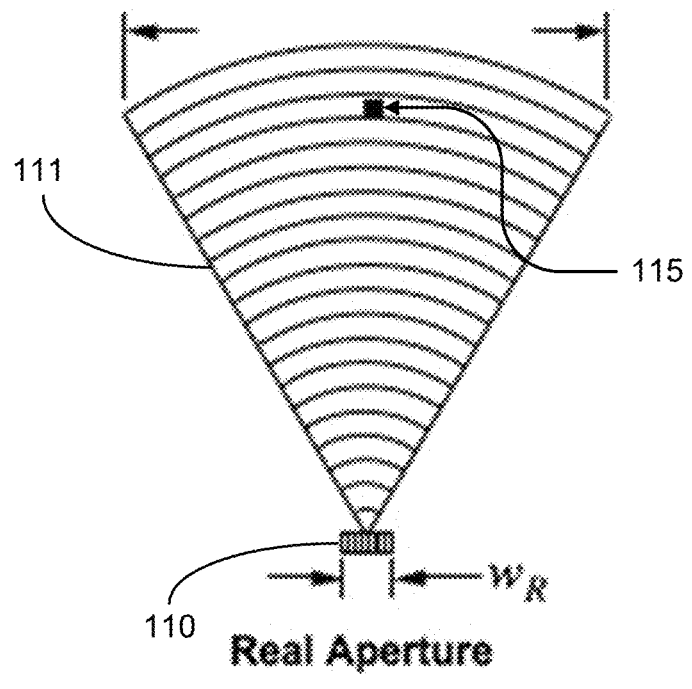
FIG. 1A shows a diagram of an ultrasound beam generated by a transducer array that forms a real aperture beam in ultrasound imaging.

In conventional real aperture ultrasound imaging systems, the quality of images directly depends on the acoustic field generated by the transducer of the ultrasound system. FIG. 1A shows a diagram of a real aperture ultrasound beam 111 generated by a transducer array 110, e.g., which can be configured as a single electro-acoustic transducer element or an array of multiple electro-acoustic transducer elements of width $w_R$, that forms a real aperture to form the ultrasound beam 111 directed toward a volume of interest (VOI) 115. For example, the image is typically acquired sequentially, one axial image line at a time (i.e., scan of the target area range slice by slice), which sets limits on the frame rate during imaging that may be detrimental in a variety of real-time ultrasound imaging applications, e.g., including the imaging of moving targets.

To address limitations with conventional real aperture ultrasound imaging, synthetic aperture ultrasound imaging can be used to improve the quality of ultrasound images. A "synthetic aperture" is the concept in which the successive use of one or more smaller, real apertures (sub-apertures) to examine a VOI, whose phase centers are moved along a known one-dimensional (1D), two-dimensional (2D), and/or three-dimensional (3D) path of a particular or arbitrary shape, to realize a larger effective (non-real) aperture for acquiring an image. The synthetic aperture can be formed by mechanically altering the spatial position of the electro-acoustic transducer (e.g., transducer array) to the successive beam transmission and/or receiving locations, by electronically altering the phase center of the successive beam transmission and/or receiving locations on the electro-acoustic transducer array, or by a combination of both. Synthetic aperture-based imaging was originally used in radar systems to image large areas on the ground from aircraft scanning the area of interest from above. Synthetic aperture focusing in ultrasound imaging is based on the geometric distance from the ultrasound transmitting elements to the VOI location and the distance from that location back to the ultrasound receiving element. In ultrasound imaging, the use of the synthetic aperture enables the focusing on a point in the target region by analyzing the received amplitude and phase data of the returned echoes (e.g., mono-static and bi-static echoes), recorded at each of a plurality of transmitter and receiver positions from all directions, to provide information about the entire area. Since the direction of the returned echoes cannot be determined from one receiver channel alone, many receiver channels are used to determine the information contained in the returning echoes, which are processed across some or all of the channels to ultimately render information used to produce the image of the target region.

Figure 1B:
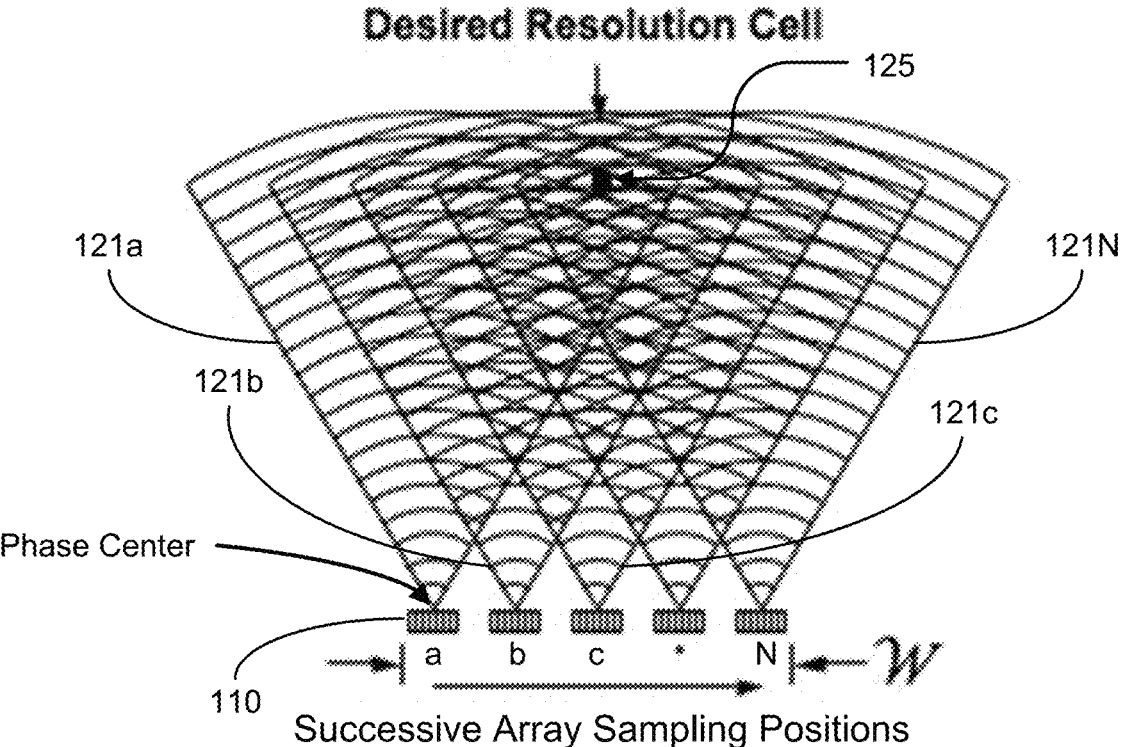
FIG. 1B shows a diagram of an ultrasound beam generated by a transducer array whose phase center is in successive positions to form a synthetic aperture beam in ultrasound imaging.

The synthetic aperture array may be comprised of one or more real beam aperture sub-arrays whose phase center is moved from sampling position to position, as shown in FIG. 1B. For example, the transducer array may be composed of multiple real aperture sub-arrays, which together in combination comprise an entire array, with the phase center of one or more of the sub-arrays moved (e.g., electronically, mechanically, or both) from sampling position to position.

In one example of a synthetic aperture ultrasound technique, a single or multiple transducer elements can be used to transmit a diverging wavefront at a plurality of positions across a region containing a VOI, forming an effective aperture covering the full image region. FIG. 1B shows a diagram of an ultrasound beam generated by transducer arrays whose phase centers are moved in successive positions to form a synthetic aperture beam in ultrasound imaging. As shown in the diagram, multiple ultrasound beams 121*a*, 121*b*, . . . 121N are generated by one or more transducer arrays 110 whose phase center is positioned mechanically, electronically, or both in N successive positions (positions a, b, c, . . . . N) along an arbitrary, but known, open or closed 1D, 2D or 3D path W, which for example, may be a straight line, an arc, a circle, a spiral, or any defined curvilinear path, etc., to form a synthetic aperture for ultrasound imaging of a VOI 125. The received mono-static and bi-static echo signals for all or some of the transducer elements of the transducer 110 in the effective aperture are sampled for each transmission. For example, the individual received ultrasound signal data can be used for making a low resolution image based on the individual unfocused transmissions, which are subsequently processed to produce a two-dimensional (2D) and/or three-dimensional (3D) focused image from the individual received ultrasound mono-static and bi-static echo signals. For example, the use of synthetic aperture ultrasound imaging can reduce the system complexity and cost in ultrasound imaging, e.g., as compared to a real beam system of equivalent performance.

The types of waveforms used to generate the acoustic pulse can also affect the quality of images produced in ultrasound imaging. Some conventional ultrasound imaging techniques may use only amplitude information from the reflected signal. For example, when one pulse is emitted, the reflected signal can be sampled continuously. In biological tissue, sound velocity can be considered fairly constant (e.g., to within less than 10%, excluding bone), in which the time between the emission of a waveform and the reception of a reflected signal is dependent on the distance the waveform travels in that tissue structure (e.g., the depth of the reflecting structure). Therefore, reflected signals may be sampled at multiple time intervals to receive the reflected signals being reflected from multiple depths. Also, different tissues at different depths can partially reflect the incident waveform with different amounts of energy, and thus the reflected signal from different mediums can have different amplitudes. A corresponding ultrasound image can be constructed based on depth. The time before a new waveform is emitted can therefore be dependent of the maximum depth that is desired to image. Ultrasound imaging techniques employing pulsed monochromatic and/or narrow instantaneous bandwidth waveforms can suffer from poor resolution of image processing and production. Yet, waveforms with spread-spectrum, wide instantaneous bandwidth characteristics that are coded (e.g., by frequency and/or phase) can enable real-time control of ultrasound imaging and higher quality resultant images.

Disclosed are techniques, systems, and devices for generating, transmitting, receiving, and processing coherent, spread-spectrum, instantaneous-wideband, coded waveforms used in synthetic aperture ultrasound (SAU) imaging.

The disclosed SAU imaging techniques can provide improved image quality, contrast and resolution over existing ultrasound imaging techniques and can enable tissue differentiation and classification. Additionally, the exemplary coherent, spread-spectrum, instantaneous-wideband, coded waveforms employed in the disclosed technology are not constrained by hardware design limitations currently present in conventional medical ultrasound devices.

The use of coherent waveforms in implementations of the disclosed SAU techniques can permit the complex correlation of a portion of, or the entire, echo return with a selected reference signal, such as, for example, the transmitted waveform. Such coherent complex correlations permit the reduction of image and signal artifacts and the extraction of data at lower signal-to-noise ratios and in the presence of interference.

The use of spread-spectrum signals in implementations of the disclosed SAU techniques can allow the definitive design of acoustic waveforms that have deliberate and explicit amplitude and phase frequency content. For example, by explicitly defining the amplitude and/or phase of each frequency component of the spread-spectrum composite acoustic waveforms can be constructed such that signal and information processing techniques can be employed to extract the maximal amount of information from the echo returns, e.g., approaching mathematical limits.

The use of instantaneous coherent, wideband, spread-spectrum, coded waveforms in implementations of the disclosed SAU techniques can enable the capture of all available information during each transmit-receive interval, e.g., thereby minimizing the corruption of the returned signal by the inhomogeneous, dynamic nature of living biological specimens, and by motion induced artifacts of the collection process. Additionally, for example, fundamental physical parameters (e.g., such as bulk modulus, density, attenuation, acoustic impedance, amplitude reflections, group delay, or other) can be extracted by using signal and information processing methods of the disclosed technology to enable differentiation and classification of the tissue in the VOI. For example, some signal and information processing methods of the disclosed SAU technology may include inverse mathematical techniques operating on the received frequency and angular dependent wideband, spread-spectrum, synthetic aperture received signal echoes for differentiating and/or classifying tissue in the VOI, as well as expert system techniques, e.g., deterministic, support vector network and neural network techniques.

Explicit amplitude and/or phase coding of each frequency component of waveforms in implementations of the disclosed SAU techniques can provide multiple benefits. For example, amplitude coding allows for the explicit compensation of the frequency-dispersive properties of the transducer array and of the acoustic propagation channel. The amplitude and/or phase coding of each frequency component permits deterministic beamforming and steering of wide-instantaneous waveforms. Explicit amplitude and phase coding of each frequency component of an exemplary transmitted signal permits the minimization of the peak-to-average power ratio (PAPR), and the spreading of the acoustic power over a wide band, e.g., to minimize deleterious biological effects. For example, by explicitly defining the amplitude and/or phase of each frequency component of spread-spectrum signals, waveforms can be constructed that may be transmitted simultaneously, which exhibit minimal interference with each other, such that signal and information processing techniques can be employed to recover the received signal associated with each individual transmitted waveform. Further, the coded, spread-spectrum acoustic waveforms of the disclosed SAU technology can allow for motion compensation due to particular ambiguity properties of these waveforms.

In one aspect, a method of producing an acoustic waveform in an acoustic imaging device is disclosed. The method includes synthesizing, in one or more waveform synthesizers, one or more composite waveforms formed of a plurality of individual coded waveforms to be transmitted toward a target from one or more spatial positions of a transducer array of the acoustic imaging device and/or one or more beam phase center positions of the transducer array. The individual coded waveforms of the composite waveform are mutually orthogonal to each other and are in different frequency bands, such that each of the individual mutually orthogonal coded waveforms includes a unique frequency with a corresponding phase. The method includes transmitting, from one or more transmitting positions relative to the target, one or more composite acoustic waveforms formed of a plurality of acoustic waveforms, in which the transmitting includes selecting one or more transducing elements of an array to transduce the plurality of individual orthogonal coded waveforms of the respective one or more composite waveforms into the plurality of corresponding acoustic waveforms of the respective one or more composite acoustic waveforms. The method includes receiving, at one or more receiving positions relative to the target, returned acoustic waveforms that are returned from at least part of the target corresponding to the transmitted acoustic waveforms, in which the receiving includes selecting at least some of the transducing elements of the array to receive the returned acoustic waveforms, and in which the receiving positions include one or both of spatial positions of the array of transducer elements relative to the target and beam phase center positions of the array to receive the returned acoustic waveforms. The transmitted acoustic waveforms and the returned acoustic waveforms produce an enlarged effective aperture of the acoustic imaging device.

In some implementations, for example, the method includes, in transmitting the acoustic waveforms to the target, controlling the transducer elements of the array to cause the composite waveforms to change in orientation with respect to the target so that the target receives the acoustic waveforms at different waveform orientations over an imaging period. For example, the change in orientation of the composite waveforms with respect to the target can include transmitting different composite waveforms from the same or different spatial positions, transmitting the same or different composite waveforms from different spatial positions, and transmitting the same or different composite waveforms from different beam phase center positions on the array of transducer elements.

In some implementations, for example, the method includes converting the received returned acoustic waveforms from analog format to digital format as one or more received composite waveforms corresponding to the one or more composite waveforms, each comprising information of the target, in which the information includes an amplitude and a phase associated with the corresponding frequency bands of the received composite waveform. Also, in some implementations, for example, the method can include processing the received returned acoustic waveforms (of the one or more received composite waveforms) to produce an image (e.g., 2D and/or 3D image) of at least part of the target.

In one aspect, a synthetic aperture ultrasound imaging system is disclosed. The system includes a waveform generation unit including one or more waveform synthesizers coupled to a waveform generator. The waveform generation unit synthesizes a composite waveform that includes a plurality of individual orthogonal coded waveforms corresponding to different frequency bands that are generated by the one or more waveform synthesizers according to waveform information provided by the waveform generator, in which the individual orthogonal coded waveforms are mutually orthogonal to each other and correspond to different frequency bands, such that each of the individual orthogonal coded waveforms includes a unique frequency with a corresponding phase. The system includes a transmit/receive switching unit that switches between a transmit mode and a receive mode. The system includes an array of transducer elements in communication with the transmit/receive switching unit. The array of transducer elements are configured to transmit a composite acoustic waveform comprising a plurality of acoustic waveforms from one or more transmitting positions relative to the target, in which the transmitted acoustic waveforms of the composite acoustic waveform are based on the synthesized individual orthogonal coded waveforms of the composite waveform. The array of transducer elements are also configured to receive, e.g., at one or more receiving positions relative to the target, returned acoustic waveforms corresponding to the plurality of transmitted acoustic waveforms that return from at least part of the target. The transmitted acoustic waveforms and the returned acoustic waveforms produce an enlarged effective aperture of the synthetic aperture acoustic waveform imaging system. The transmitting positions and the receiving positions for transmitting and receiving the respective waveforms, respectively, include one or both of spatial positions of the array of transducer elements relative to the target and beam phase center positions on the array to transmit and/or receive the acoustic waveforms. The system includes a multiplexing unit in communication with the array of transducer elements to select one or more transducing elements of an array to transduce the plurality of individual orthogonal coded waveforms into the plurality of corresponding acoustic waveforms, and to select one or more transducing elements of the array to receive the returned acoustic waveforms. In some implementations, for example, the system includes an array of analog to digital (A/D) converters to convert the received returned acoustic waveforms that are received by the array of transducer elements from analog format to digital format, in which the received returned acoustic waveforms provide information of the target. The system includes a controller unit in communication with the waveform generation unit and the array of transducer elements (e.g., which can be via the array of A/D converters), in which the controller unit includes a memory unit to store data and a processing unit coupled to the memory unit to process information about the target as data. The system can include a user interface unit in communication with the controller unit. In some implementations of the system, for example, the controller unit is configured to produce an image of at least part of the target from the processed data.

Figure 1C:
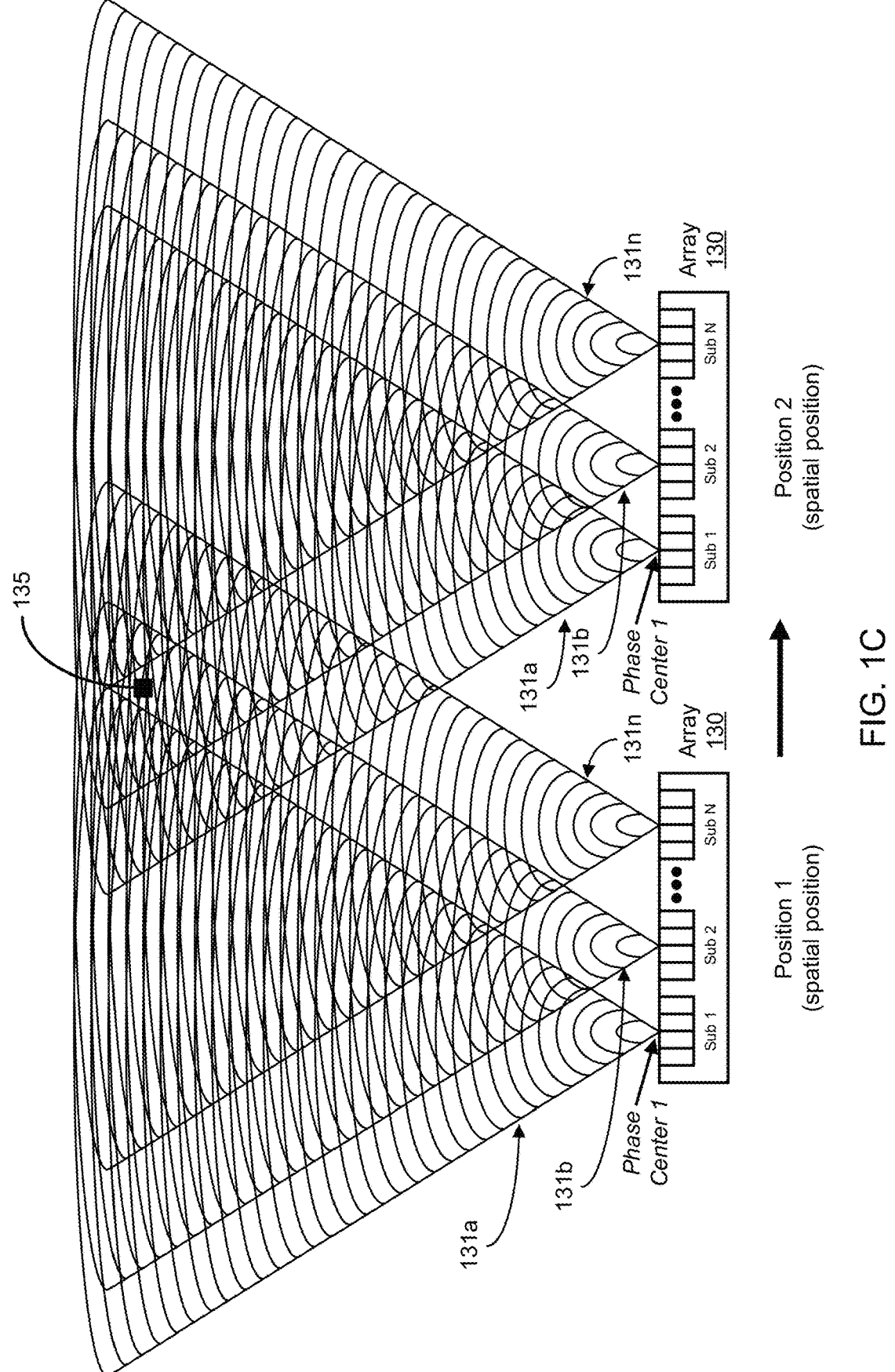
FIGS. 1C and 1D show diagrams of exemplary composite ultrasound transmit and/or receive beams generated by a transducer array that forms a synthetic aperture beam from multiple transmitting and/or receiving positions.
Figure 1D:
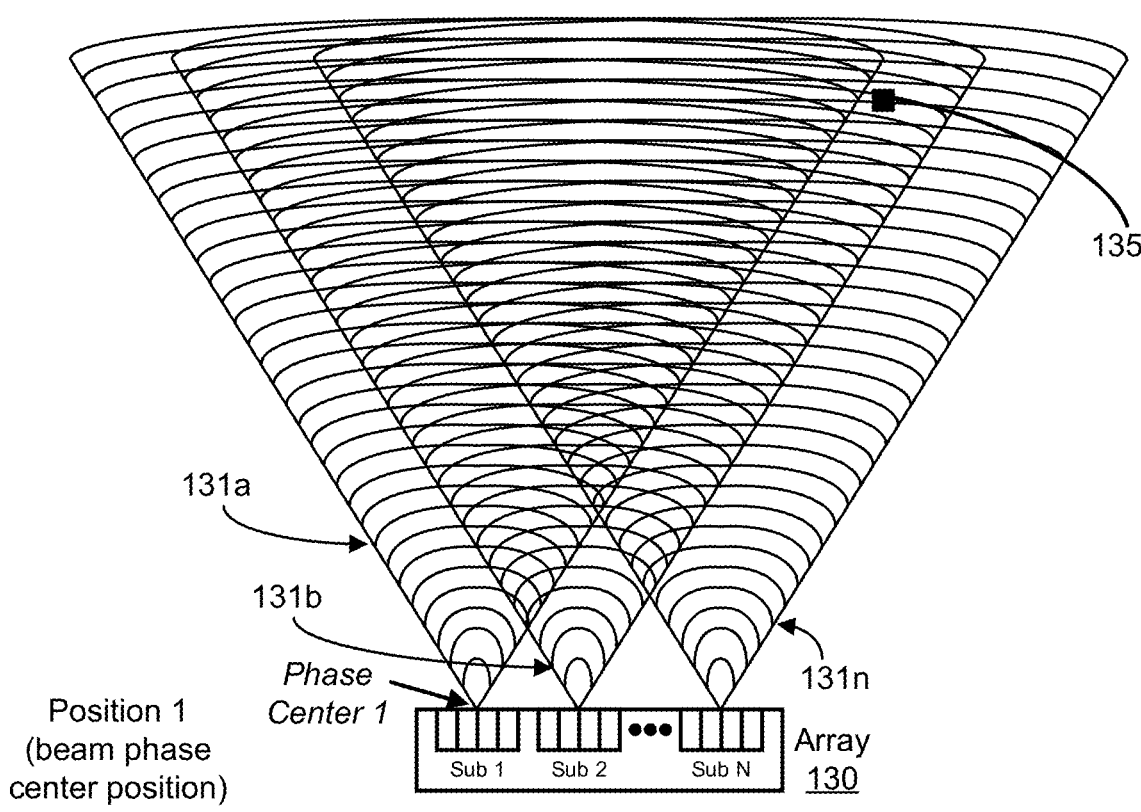
Figure 1D:
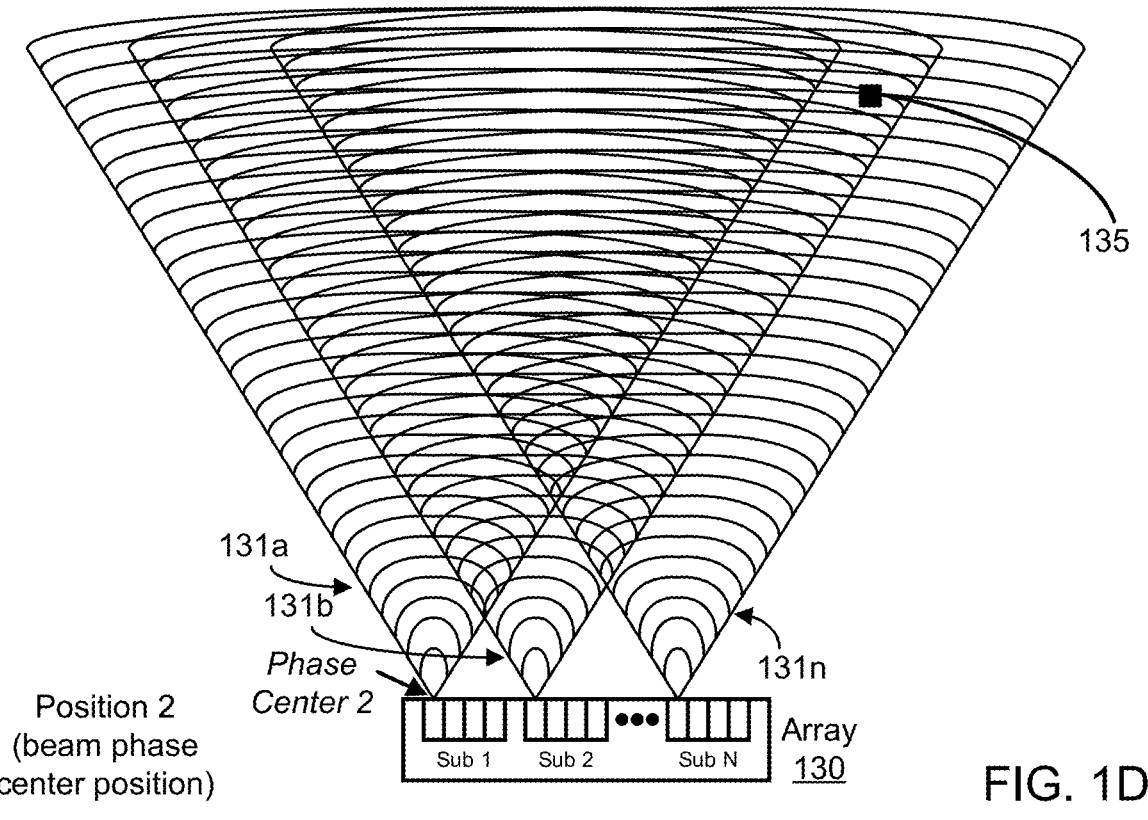

FIGS. 1C and 1D show diagrams of exemplary composite ultrasound beams generated by a transducer array that forms a synthetic aperture beam from multiple transmitting positions. As shown in the diagram, a transducer array 130 includes multiple real aperture sub-arrays Sub 1, Sub 2, . . . . Sub N, in which each sub-array includes individual transducer elements (e.g., such as 1 to 16, 32, 64, etc. elements). Some or all of the transducer elements that form array 130 can transmit (e.g., either sequentially, simultaneously or randomly) one or more composite acoustic waveforms of individual, mutually orthogonal, coded acoustic waveforms 131a, 131b, . . . 131n transmitted to a target volume of interest (VOI) 135 from multiple sub-array phase center positions to form a synthetic aperture for ultrasound imaging. Some or all of the transducer elements that form the array 130 can also receive the returned acoustic waveforms corresponding to the transmitted acoustic waveform (formed based on the individual, mutually orthogonal, coded acoustic waveforms 131a, 131b, . . . 131n), in which the received acoustic waveforms are scattered back and returned (e.g., reflected, refracted, diffracted, delayed, and/or attenuated) from at least part of the VOI 135. The received individual acoustic waveforms thereby form one or more received composite waveforms that correspond to the transmitted composite acoustic waveforms. The composite acoustic waveform is generated based on a composite synthetic waveform formed of multiple spread-spectrum, wide instantaneous bandwidth, coded waveforms used to generate the individual acoustic waveforms. The individual, composite, acoustic waveforms 131a, 131b, . . . 131n can be transducted by one or more of the sub-arrays of the transducer array 130. The transducer array 130 can be positioned at multiple physical positions along a known path (e.g., shown as position 1 to position 2 in FIG. 1C), and/or multiple beam-steering positions (e.g., shown as position 1 to position 2 in FIG. 1D), such that the phase center is positioned mechanically, electronically or both mechanically and electronically in the successive positions, e.g., forming a synthetic aperture.

Figure 1E:
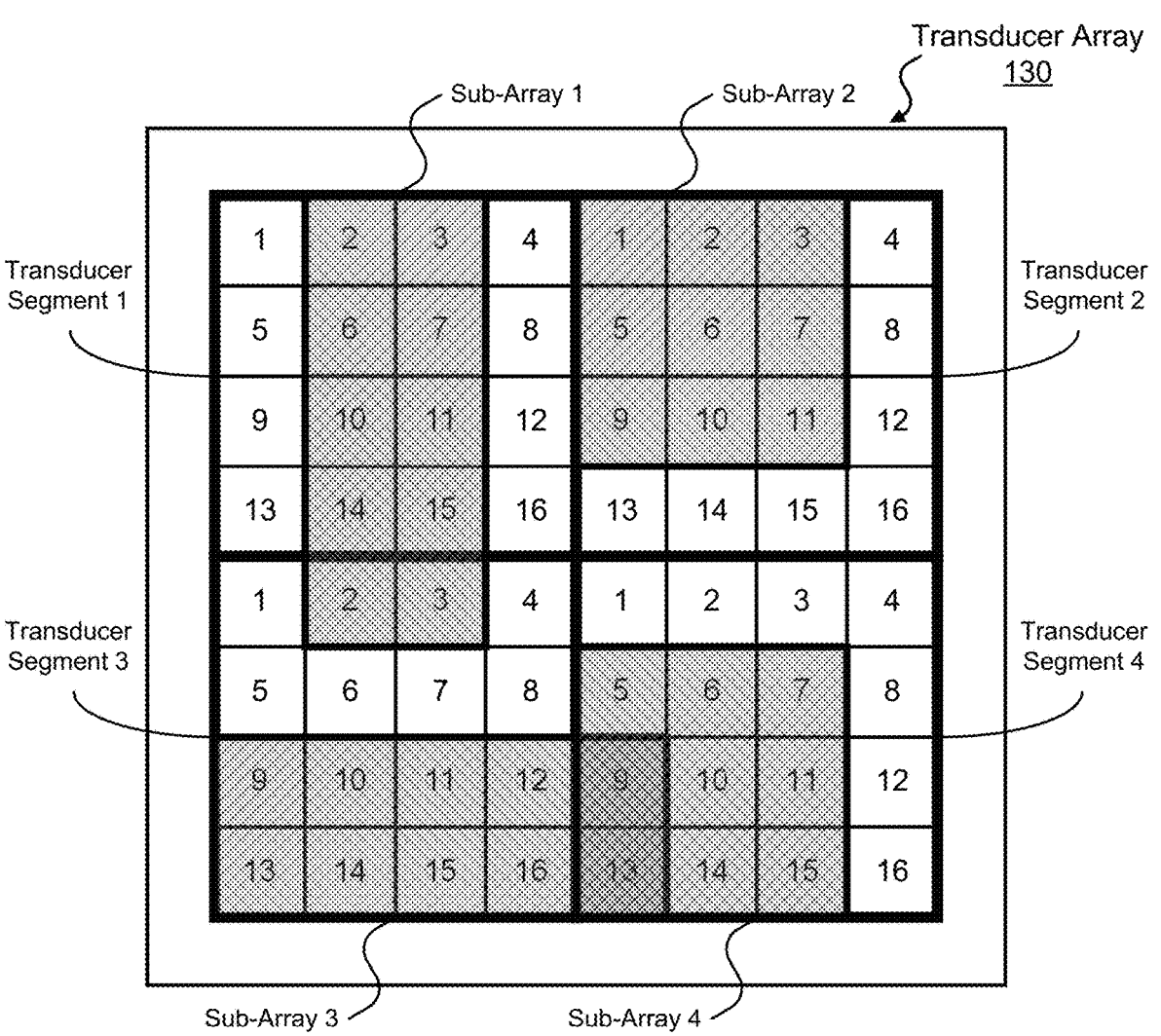
FIG. 1E shows a diagram of an exemplary transducer array for generating a composite ultrasound beam of the disclosed technology.

In some implementations, for example, various array segments comprising various combinations of transducer elements across one or more sub-arrays can be utilized to generate the orthogonal coded acoustic waveforms 131a, 131b, . . . 131n. FIG. 1E shows a diagram of an exemplary transducer array for generating a composite ultrasound beam of the disclosed technology. In the example of FIG. 1E, the transducer array 130 includes 64 individual transducer elements arranged in four transducer segments (e.g., transducer segment 1, 2, 3, and 4). In this example, one or more sub-arrays, comprising any of the 64 individual transducer elements (e.g., including transducer elements among one or more of the four transducer segments), can transmit (e.g., either sequentially, simultaneously or randomly) the individual, orthogonal, coded acoustic waveforms 131a, 131b, . . . 131n. A sub-array can include combinations of the individual transducer elements in one transducer segment or among a plurality of the transducer segments. For example, a sub-array 1 includes transducer elements 2, 3, 6, 7, 10, 11, 14 and 15 of transducer segment 1 and transducer elements 2 and 3 of transducer segment 3; a sub-array 2 includes transducer elements 1, 2, 3, 5, 6, 7, 9, 10, and 11 of transducer segment 2; a sub-array 3 includes transducer elements 9, 10, 11, 12, 13, 14, 15, and 16 of transducer segment 3 and transducer elements 9 and 13 of transducer segment 4; and a sub-array 4 includes transducer elements 5, 6, 7, 9, 10, 11, 13, 14, and 15 of transducer segment 4. Configurations of the sub-arrays can be produced using a switching element (e.g., such as a multiplexer unit) interfaced between waveform generators and the transducer array, as shown later in FIG. 2A and FIG. 2B.

Figure 2A:
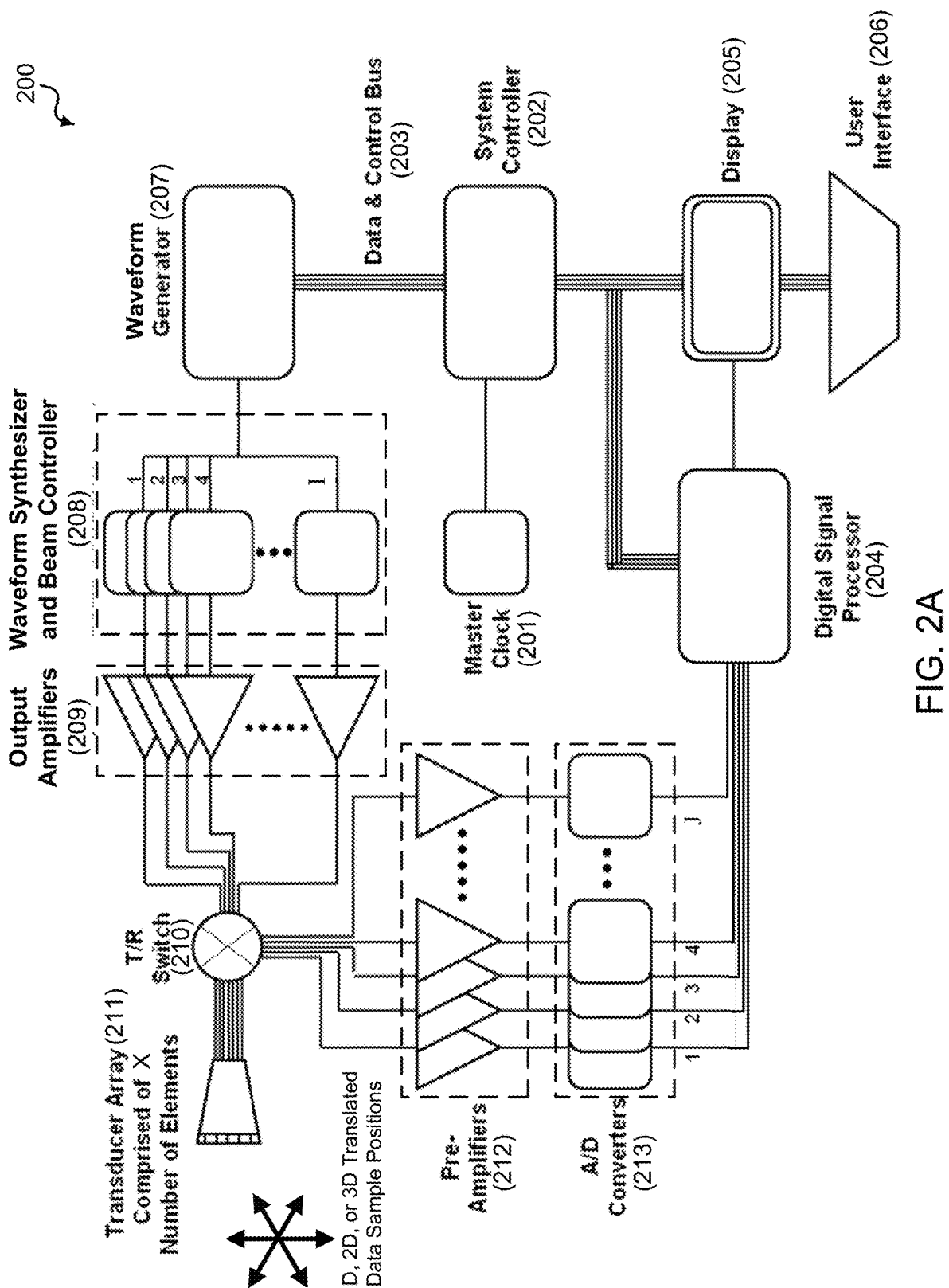
FIG. 2A shows a block diagram of an exemplary synthetic aperture ultrasound system using spread-spectrum coded waveforms.

FIG. 2A shows a block diagram of an exemplary Synthetic Aperture Ultrasound (SAU) System 200 that can produce acoustic waveforms with enhanced waveform properties across an expanded effective (synthetic) aperture. The enhanced waveform properties of the composite acoustic waveforms produced by the SAU System 200 include a spread-spectrum, wide instantaneous bandwidth, coherent, pseudo-random noise characteristics, and coding. The SAU System 200 can be configured in one of many system designs. In one example, the SAU System 200 can include a Master Clock 201 for time synchronization. The Master Clock 201 can be interfaced with a System Controller 202, as well as other modules of the SAU System 200 operating in temporal synchronization with each other. The System Controller 202 can include a processing unit, e.g., a central processing unit (CPU) of RISC-based or other types of CPU architectures. The System Controller 202 can also include at least one input/output (I/O) unit(s) and/or memory unit(s), which are in communication with the processing unit, to support various functions of the System Controller 202. For example, the processing unit can be associated with a system control bus, e.g., Data & Control Bus 203. The System Controller 202 can be implemented as one of various data processing architectures, such as a personal computer (PC), laptop, tablet, and mobile communication device architectures.

The memory unit(s) can store other information and data, such as instructions, software, values, images, and other data processed or referenced by the processing unit. Various types of Random Access Memory (RAM) devices, Read Only Memory (ROM) devices, Flash Memory devices, and other suitable storage media can be used to implement storage functions of the memory unit(s). The memory unit(s) can store pre-stored waveforms and coefficient data and information, which can be used in the implementation of generating a waveform, e.g., such as a spread-spectrum, wide-instantaneous bandwidth, coherent, pseudo-random noise, and frequency and/or phase-coded waveform. The memory unit(s) can store data and information obtained from received and processed waveforms, which can be used to generate and transmit new waveforms. The memory unit(s) can be associated with a system control bus, e.g., Data & Control Bus 203.

The I/O unit(s) can be connected to an external interface, source of data storage, and/or display device. The I/O unit(s) can be associated with a system control bus, e.g., Data & Control Bus 203. Various types of wired or wireless interfaces compatible with typical data communication standards, such as, but not limited to, Universal Serial Bus (USB), IEEE 1394 (Fire Wire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement the I/O unit. The I/O unit can interface with an external interface, source of data storage, or display device to retrieve and transfer data and information that can be processed by the processor unit, stored in the memory unit, or exhibited on an output unit.

The System Controller 202 can control all of the modules of the SAU System 200, e.g., through connection via the Data & Control Bus 203. For example, the Data & Control Bus 203 can link the System Controller 202 to one or more attached digital signal processors, e.g., Digital Signal Processor 204, for processing waveforms for their functional control. The Digital Signal Processor 204 can include one or many processors, such as but not limited to ASIC (application-specific integrated circuit), FPGA (field-programmable gate array), DSP (digital signal processor), AsAP (asynchronous array of simple processors), and other types of data processing architectures. The Data & Control Bus 203 can also link the System Controller 202, as well as the Digital Signal Processor 204, to one or more display units with modules for user interfaces, e.g., Display 205 with a module User Interface 206 to provide information to a user or operator and to receive input/commands from the user or operator. The Display 205 can include many suitable display units, such as but not limited to cathode ray tube (CRT), light emitting diode (LED), and liquid crystal display (LCD) monitor and/or screen as a visual display. The Display 205 can also include various types of display, speaker, or printing interfaces. In other examples, the Display 205 can include other output apparatuses, such as toner, liquid inkjet, solid ink, dye sublimation, inkless (such as thermal or UV) printing apparatuses and various types of audio signal transducer apparatuses. The User Interface 206 can include many suitable interfaces including various types of keyboard, mouse, voice command, touch pad, and brain-machine interface apparatuses.

The SAU System 200 can include Waveform Generator 207, which can be controlled by the System Controller 202 for producing one or more digital waveforms. The one or more digital waveforms can be generated as analog electronic signals (e.g., analog waveforms) by at least one element in an array of waveform synthesizers and beam controllers, e.g., represented in this example as Waveform Synthesizer and Beam Controller 208. The Waveform Generator 207 can be at least one of a function generator and an arbitrary waveform generator (AWG). For example, the Waveform Generator 207 can be configured as an AWG to generate arbitrary digital waveforms for the Waveform Synthesizer and Beam Controller 208 to synthesize as individual analog waveforms and/or a composite analog waveform. The Waveform Generator 207 can also include at least one memory unit(s) that can store pre-stored waveforms and coefficient data and information used in the generation of a digital waveform.

The SAU System 200, as shown in FIG. 2A, includes the Waveform Synthesizer and Beam Controller 208 comprising I number of array elements. In one example, the Waveform Synthesizer and Beam Controller 208 can be configured to include at least one waveform synthesizer element on each line of the I number of array waveform synthesizers. In another example, the Waveform Synthesizer and Beam Controller 208 can include at least one beam controller element on each line of the I number of array beam controllers. In another example, the Waveform Synthesizer and Beam Controller 208 can include at least one waveform synthesizer element and beam controller element on each line of the I number of array waveform synthesizers and beam controllers. The Waveform Synthesizer and Beam Controller 208 can include a phase-lock loop system for generation of an electronic signal, e.g., a radio frequency (RF) waveform. An exemplary RF waveform can be synthesized by the Waveform Synthesizer and Beam Controller 208 from individual waveforms generated in the array elements of the Waveform Synthesizer and Beam Controller 208, e.g., one individual RF waveform can be generated in one array element substantially simultaneously to all other individual waveforms generated by the other array elements of the Waveform Synthesizer and Beam Controller 208. Each individual orthogonal RF waveform can be defined for a particular frequency band, also referred to as a frequency component or 'chip', and the waveform properties of each individual orthogonal waveform can be determined by the Waveform Generator 207, which can include at least one amplitude value and at least one phase value corresponding to the chip. The Waveform Generator 207 can issue commands and send waveform data including information about each individual orthogonal waveform's properties to the Waveform Synthesizer and Beam Controller 208 for generation of individual orthogonal RF waveforms that may be combined together to form a composite RF waveform by the Waveform Synthesizer and Beam Controller 208.

The individual orthogonal RF waveforms and/or the composite RF waveform generated by the Waveform Synthesizer and Beam Controller 208 can be modified by Output Amplifiers 209, which includes an array of I number of amplifiers, e.g., by amplifying the gain and/or shifting the phase of a waveform. In some examples, the Output Amplifiers 209 are configured as linear amplifiers. The Output Amplifiers 209 can be used as transducer drivers. The individual RF waveforms and/or the composite RF waveform can be passed to Transmit/Receive (T/R) Switch 210, e.g., an N-pole double-throw transmit/receive switch. The T/R Switch 210 can be interfaced with a transducer module of the SAU System 200. The T/R Switch 210 can operate as a multiplexing unit, e.g., by including N-pole multiplexing switches. A generated RF waveform, e.g., the composite RF waveform and/or at least one individual RF waveform, that is to be transmitted into a target medium can be transduced into, for example, an acoustic wave by the transducer module. In the example shown in FIG. 2A, the transducer module is configured as an array of transducer elements, e.g., Transducer Array 211 comprising X number of transducer elements. For example, the transduced acoustic wave can be emitted in the form of an acoustic waveform burst. For example, selected array element of the Transducer Array 211 may generate (e.g., transduct) two or more individual orthogonal acoustic waveforms that correspond to the individual orthogonal waveforms determined by the Waveform Generator 207 and combined spatially to form a composite acoustic waveform. As an additional example, selected array element of the Transducer Array 211 may generate (e.g., transduct) one or more composite acoustic waveforms that correspond to the composite waveforms determined by the Waveform Generator 207.

For example, when the T/R Switch 210 is configured in transmit mode, the exemplary transduced and transmitted composite acoustic waveform can be transmitted toward a target area from a plurality of positions of the Transducer Array 211 relative to the target, e.g., biological tissue, in which the transduced and transmitted acoustic waveform forms a spatially combined acoustic waveform. The transmitted composite acoustic waveform can propagate into the target medium, which for example, can have one or more inhomogeneous mediums that partially transmit and partially reflect the transmitted acoustic waveform. For example, after the acoustic waveform has been transmitted, the T/R Switch 210 can be configured into receive mode. The exemplary composite acoustic waveforms that are (at least partially) reflected by the target can be received by the Transducer Array 211, referred to as returned acoustic waveforms. In some examples, selected array element of X array elements of Transducer Array 211 can be configured to receive a returned acoustic waveform corresponding to the individual orthogonal waveforms (e.g., frequency chips) and convert it to an analog RF waveform. In other examples, selected transducer elements of the Transducer Array 211 can be configured to receive the returned acoustic waveform corresponding to the transmitted composite waveform, e.g., based on a selection control signal determined by the System Controller 202 in communication with exemplary control logic of the Transducer Array 211, and convert it to a composite analog RF waveform.

In some implementations, for example, the Transducer Array 211 can have the beam phase center(s) mechanically translated in one dimension, two dimensions, and/or three dimensions of data sampling/ultrasound scanning positions by spatially moving the Transducer Array 211 to produce a synthetic aperture during an ultrasound imaging implementation using the SAU System 200. In an additional example, the Transducer Array 211 can remain stationary, and the beam phase center(s) may be translated electronically in one dimension, two dimensions, and/or three dimensions along the stationary Transducer Array 211 by addressing a portion of the X transducer elements sequentially or randomly by the System Controller 202 as data sampling/ultrasound scanning positions to produce a synthetic aperture during an ultrasound imaging implementation using the SAU System 200. As a further example, the SAU System 200 can both mechanically and electronically translate the phase centers in one dimension, two dimensions, and/or three dimensions of data sampling/ultrasound scanning positions to produce a synthetic aperture during an ultrasound imaging implementation.

Figure 2B:
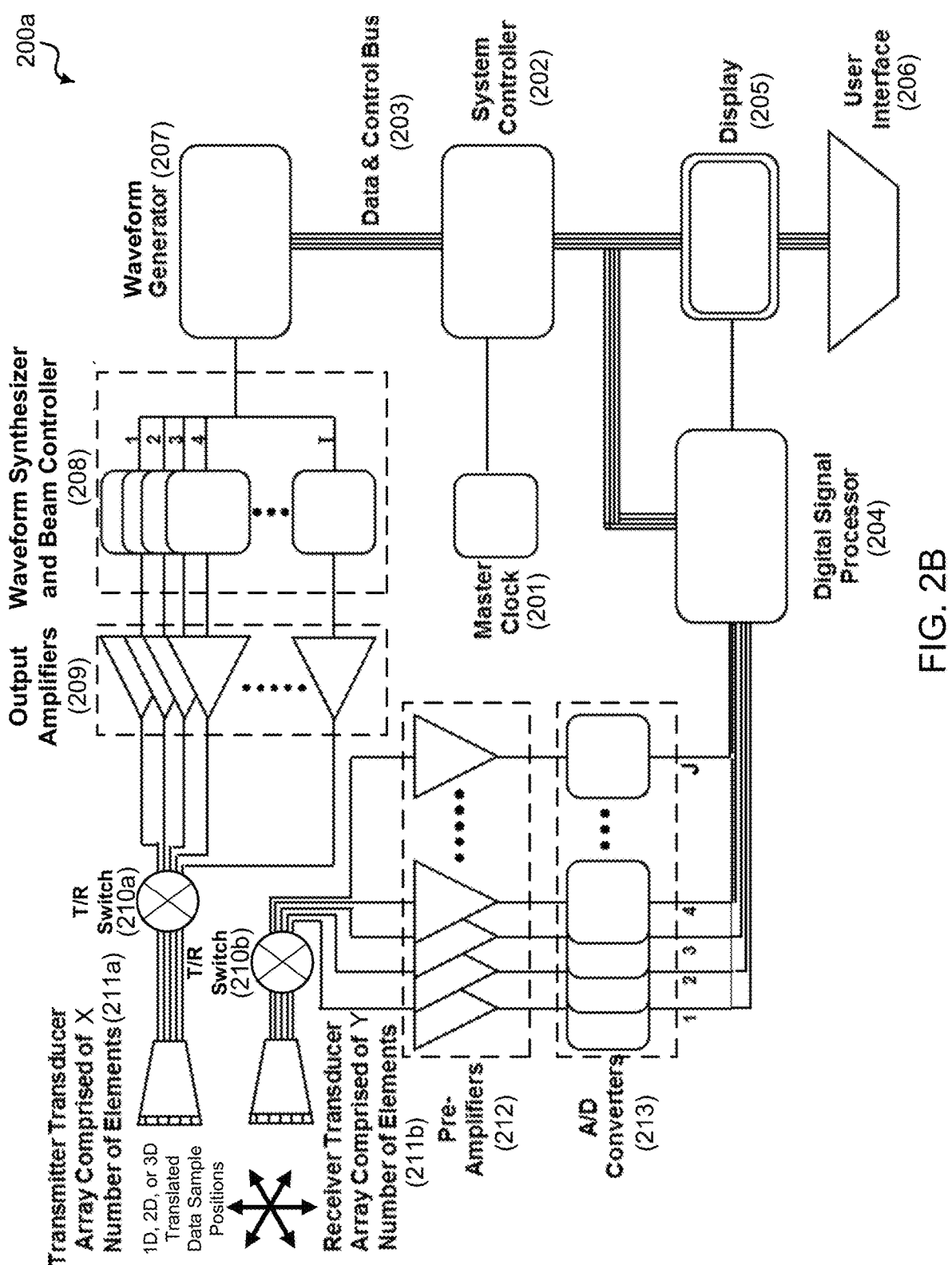
FIG. 2B shows a block diagram of another exemplary synthetic aperture ultrasound system using spread-spectrum coded waveforms.

In some implementations, for example, the individual RF waveforms and/or the composite RF waveform can be passed directly to separate transmitting transducer arrays, e.g., either separately or simultaneously in time, and separate receiving transducer arrays can be used to receive the acoustic waveforms scattered from the volume of interest. FIG. 2B shows another exemplary embodiment of a synthetic aperture ultrasound system of the disclosed technology in a block diagram showing an SAU System 200a. The SAU System 200a is operable similar to that of the SAU System 200 to produce acoustic waveforms with enhanced waveform properties across an expanded effective (synthetic) aperture, but including: (1) a Transmitter Transducer Array 211a comprising X number of transducer elements to transduce the I number of individual waveforms (e.g., which correspond to the individual orthogonal coded waveform determined by the Waveform Generator 207) and transmit one or more acoustic waveforms, e.g., either sequentially, or simultaneously, or randomly in time; and including (2) a separate Receiver Transducer Array 211b comprising Y number of transducer elements can be configured to receive returned acoustic waveforms, and convert each to an analog RF waveform. In some examples, X can be equal Y, but in other examples, X may not equal Y. In some implementations, the SAU System 200a can include a T/R Switch 210a, configured between the Output Amplifiers 209 and the Transmitter Transducer Array 211*a*, which can operate as a multiplexing unit, e.g., by including N-pole multiplexing switches. Also, in some implementations, the SAU System 200*a* can include a T/R Switch 210*b*, configured between the Receiver Transducer Array 211*b* and Pre-Amplifier module 212, which can operate as a multiplexing unit, e.g., by including N-pole multiplexing switches. For example, the Transmitter Transducer Array 211*a* can transduce the I number of individual orthogonal coded waveforms to one or more acoustic waveforms that correspond to RF waveforms determined by the Waveform Generator 207. The transduced acoustic waveform can be emitted in the form of an acoustic waveform burst. For example, selected array elements of the Transducer Array 211*a* may generate (e.g., transduct) two or more individual orthogonal acoustic waveforms that correspond to the individual orthogonal waveforms determined by the Waveform Generator 207 and combined spatially to form one or more composite acoustic waveforms that are transmitted one or more acoustic waveforms, e.g., either sequentially, or simultaneously, or randomly in time. As additional example, selected array elements of the Transducer Array 211*a* may generate (e.g., transduct) one or more composite acoustic waveforms that correspond to the composite waveforms determined by the Waveform Generator 207 that are transmitted either sequentially, or simultaneously, or randomly in time.

In the exemplary SAU System 200*a*, the Transmitter Transducer Array 211*a* and the Receiver Transducer Array 211*b* can have a portion or all of their phase centers translated either mechanically, electronically or both mechanically and electronically in one dimension, two dimensions, and/or three dimensions of data sampling/ultrasound scanning positions to produce a synthetic aperture during an ultrasound imaging implementation using the SAU System 200*a*. In some implementations, for example, the X transducer elements of the Transmitter Transducer Array 211*a* can have a portion or all of their phase centers translated either mechanically, electronically or both mechanically and electronically in unison in one, two, and/or three dimensions, while in other implementations, for example, one or more of the phase centers of X transducer elements of the Transmitter Transducer Array 211*a* can be translated either mechanically, electronically or both mechanically and electronically separately from the other elements of the Array 211*a* in one, two, and/or three dimensions. In some implementations, for example, the X or Y transducer elements of the Transducer Array 211*a* or 211*b*, respectively, can scan (e.g., mechanically, electronically or both) the radiated acoustic beam and the received beam in angle in one and/or two angular dimensions (e.g., in azimuth and/or elevation). Similarly for example, in some implementations, the phase centers of Y transducer elements of the Receiver Transducer Array 211*b* can be translated (e.g., mechanically, electronically or both) in unison in one, two, and/or three dimensions, while in other implementations, one or more of the Y transducer elements of the Receiver Transducer Array 211*b* can be translated separately from the other elements of the Array 211*b* in one, two, and/or three dimensions. For example in one embodiment, each of the X transducer elements of the Transducer Array 211 or 211*a* corresponds to one of the I Output Amplifiers 209, e.g., X=I. Alternatively, for example to reduce the number of components, several groups of transmitter transducer elements may be formed out of the total of X transducer elements and multiplexed together to communicate with less than I Output Amplifiers 209 through N-pole multiplexing switches.

Referring to FIGS. 2A and 2B, the individual received (analog) RF waveforms can be modified by Pre-Amplifier Module 212, which includes an array of J or a fewer number of amplifiers, which in some implementations, for example, each amplifier in the array may correspond to each of the X or Y transducer elements of the Transducer Array 211 or Receiver Transducer Array 211*b*, respectively. Alternatively, for example, to reduce the number of components, several groups of receiver transducer elements may be formed out of the total of receiver transducer elements and multiplexed together to communicate with the pre-amplifiers through N-pole multiplexing switches. For example, each of the corresponding amplifiers of the Pre-Amplifier Module 212 or at least some of the amplifiers can amplify the gain and/or shifting the phase of the individual received (analog) RF waveform. In some examples, the array of J amplifiers of the Pre-Amplifier Module 212 are configured as linear amplifiers. In some examples, the Pre-Amplifier Module 212 can be implemented to perform other signal conditioning techniques to the received waveforms. After amplification and/or signal conditioning, for example, the individual received waveforms can be converted from analog format to digital format by analog to digital (A/D) Converter Module 213, which includes an array of J number of A/D converters. The A/D Converter Module 213 can include A/D converters that have low least significant bit (LSB) jitter, spurious-free dynamic range (SFDR) and waveform dependency, such that the exemplary waveforms can be adequately decoded. The converted digital representations of the individual received waveforms can be processed by a processor, e.g., the Digital Signal Processor 204, in manner that creates and forms a representative image of the target medium.

The SAU System 200 can be operated in one of many operation modes. In one example, the Master Clock 201 can provide the time base for synchronizing the modules of the SAU System 200, e.g., including the Waveform Generator 207, the Waveform Synthesizers 208, and the DSP 204. The Master Clock 201 can be configured as a low-phase noise clock such that the exemplary waveforms can be phase encoded. An operator can select synthetic aperture modes of operation at the User Interface 206. In some implementations of the SAU System 200, the synthetic aperture modes can include, but is not limited to, a synthetic aperture strip scan (SASS) mode and an exemplary synthetic aperture spotlight (SASpl) mode.

Figure 2C:
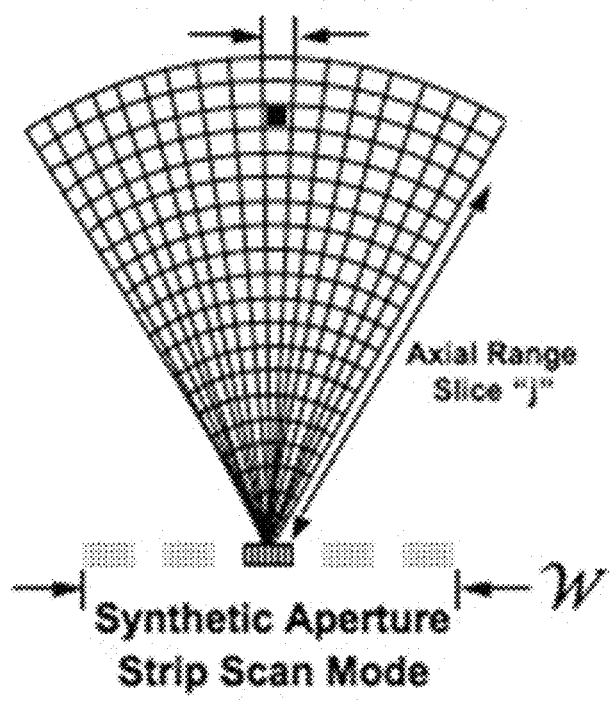
FIGS. 2C and 2D show a diagram of exemplary synthetic aperture imaging techniques of the disclosed technology.
Figure 2D:
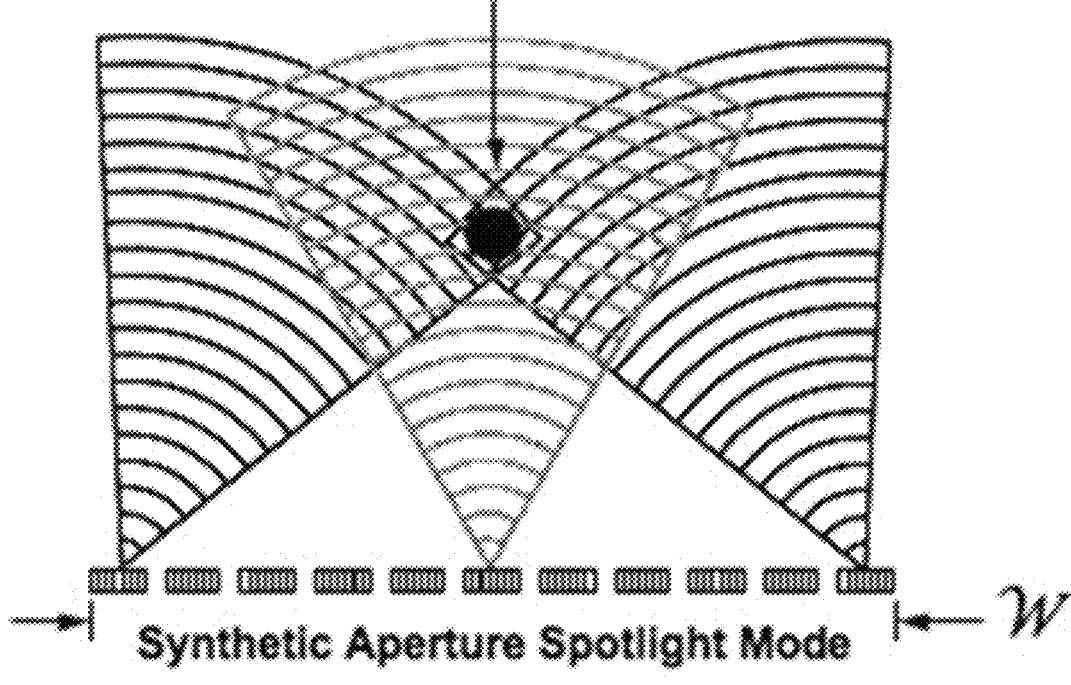

FIGS. 2C and 2D respectively show diagrams of the exemplary SASS mode and the exemplary SASpl mode of the disclosed technology. As shown in FIG. 2C, for example, the SASS mode is operable to produce a synthetic aperture based on multiple acoustic waveforms transmitted from a plurality of positions about the target via electronic, mechanical, or a combination of both electronic and mechanical translational movement of the phase center of the Transducer Array 211 in one, two, and/or three dimensions. As shown in FIG. 2D, for example, the SASpl mode is operable to steer the transmit and/or receive beams to remain centered on the VOI, e.g., thus producing a larger synthetic aperture than the SASS mode, which correspondingly produces finer lateral image resolution. The SASS and SASpl exemplary modes of operations can include 2D planar slice and/or 3D volume tomographic renderings, which can be manipulated by an operator, e.g., using the SAU System 200, to provide sagittal, coronal, transverse or any arbitrary plane of view. An operator can also select real aperture modes of operation.

For example, some exemplary modes of operation provided for the user to select at the User Interface 206 can include conventional A-Mode (e.g., 1D depth-only image), conventional B-Mode (e.g., 2D planer image—transverse vs. depth), conventional C-Mode (e.g., 2D planer image at selected depth), conventional D-Modes (e.g., Doppler Modes), and High Intensity Focused Ultrasound (HIFU) as an integrated surgical therapeutic mode combined with any one or more of the conventional or new modes of operation. Exemplary Doppler modes include Color Doppler (e.g., superposition of color coded Doppler and B-mode images), Continuous Doppler (e.g., 1D Doppler profile vs. depth), Pulsed Wave Doppler (e.g., Doppler vs. time for selected volume), and Duplex/Triplex Doppler (e.g., superposition of conventional B-Mode, conventional C-Mode or Color Doppler, and Pulsed Wave Doppler). The exemplary SAU System 200 can additionally implement new modes of operation that can generate spread-spectrum, wide-instantaneous bandwidth, frequency- and/or phase-coded waveforms. For example, a user can select a high-definition 2D image mode that is similar to the conventional B-Mode, but has significantly better image quality (e.g., higher resolution, contrast ratio, etc.), or the user can select a high-definition 3D imaging mode that produces volumetric images that can be displayed as user selectable, 2D images in a manner similar to CT and Magnetic Resonance Imaging (MRI) modalities. Additionally, for example, a user can select exemplary ATS-Modes (Artificial Tissue Staining Modes) that can comprise a B-Mode, a C-Mode, a D-Mode, or other mode combined with image color coding to aid tissue differentiation-analogous to tissue staining for microscopic histological studies; and exemplary CAD-Modes (Computer Aided Diagnostic Modes) that differentiate and identify tissue type. ATS-Modes can employ the use of features for image color coding in image processing based on one or more of a number of measured properties that are obtained from the returned echo waveform from the target area, e.g., the returned echo from an exemplary transmitted spread-spectrum, wide instantaneous bandwidth, coded acoustic waveform. CAD-Modes can use classifiers (algorithms) to classify, for example, tissue types based on features of the measured properties of the returned echoes from the target area, e.g., the returned echoes from an exemplary spread-spectrum, wide instantaneous bandwidth, coded, angularly diverse, mono-static and bi-static, synthetic aperture acoustic waveforms. The features properties can include differing impedances, waveform reflections (as a function of wavelength), group delay, etc. Some exemplary classifiers that can be employed using CAD-Modes can include deterministic classifiers, stochastic classifiers (e.g., Bayesian and Support Vector Network classifiers), and neural network classifiers.

Figure 2E:
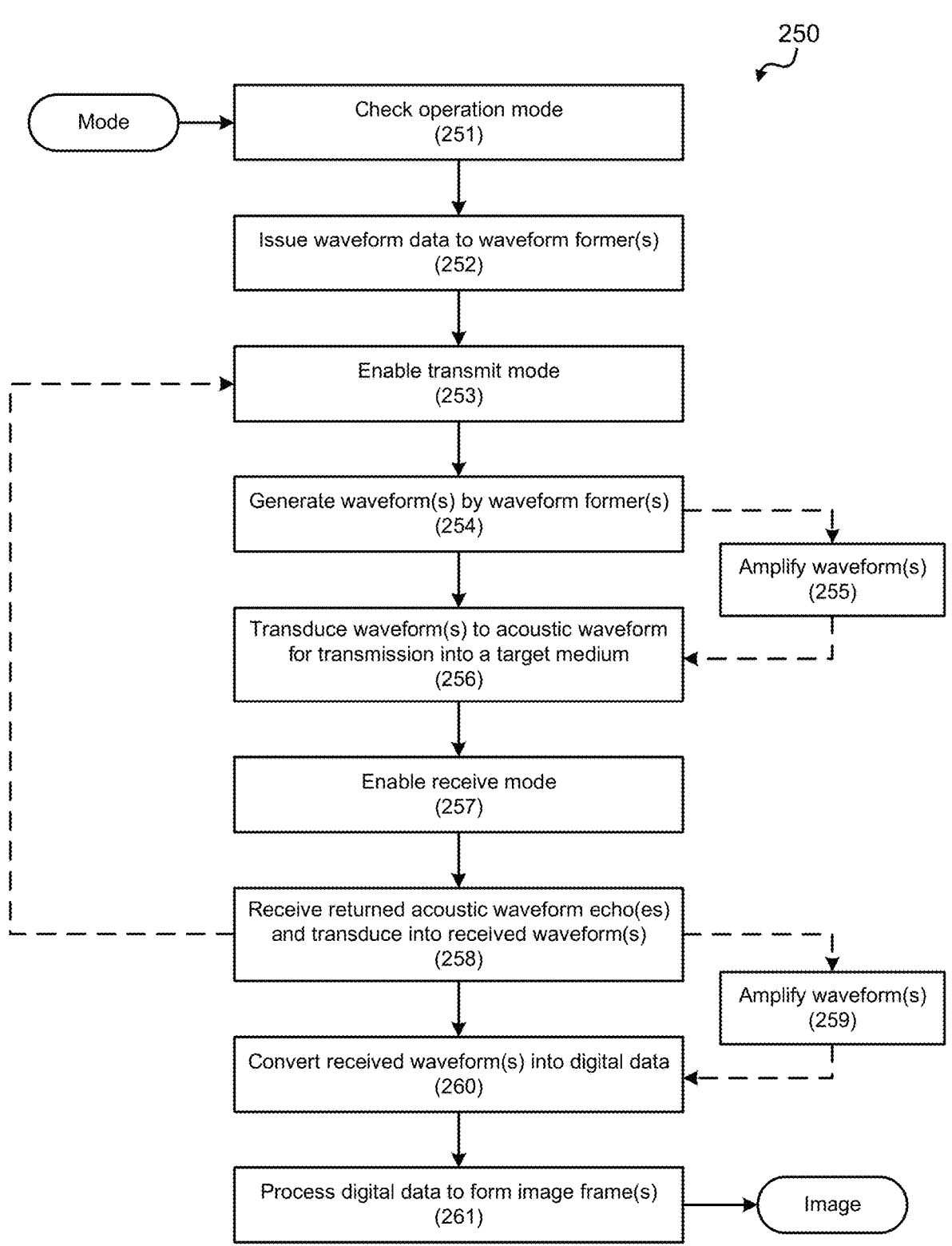
FIG. 2E shows a chart for operation of an exemplary synthetic aperture ultrasound imaging system using spread-spectrum coded waveforms.

FIG. 2E shows an exemplary operation method 250 for operating the SAU System 200 or 200a for synthetic aperture ultrasound imaging. For each time epoch, the method 250 can begin by implementing a process 251 to check a user-defined mode of operation. For example, mode of operation can be selected by a user using the User Interface 206, or the mode of operation can be selected by another entity or internally within the SAU System 200 or 200a. Based on the selected operation mode, the System Controller 202 can command the Waveform Generator 207 to issue a digital message (data) to one or more elements in the Waveform Synthesizers and Beam Controllers 208 that defines the frequency, amplitude and phase of each of the frequency chips that form a desired wideband composite RF waveform commanded, e.g., implemented in a process 252. The process 251 can occur anywhere and implemented in multiple instances during the method 250. The method 250 includes a process 252 to issue waveform data (e.g., the exemplary digital message/data) to waveform synthesizers and beamformers, such as the Waveform Synthesizers and Beam Controllers 208. The issued waveform data can include the frequency, amplitude and phase information of the desired frequency chips that are synthesized as the orthogonal frequency- and/or phase-coded waveforms, in which each coded waveform corresponds to a distinct frequency band. The method 250 includes a process 253 to enable transmit mode of the SAU System 200 or 200a. For example, when implementing the SAU System 200, the process 253 can switch the SAU System 200 in transmit mode by utilizing the System Controller 202 to command an N-pole double-throw T/R switch, e.g., T/R Switch 210, to transmit position. The process 253 can be implemented in multiple instances during the method 250, e.g., such as after receiving returned echo signals in a process 258, as described later. The method 250 includes a process 254 to generate individual analog RF waveforms that correspond to defined frequency chips. For example, each element in the array of Waveform Synthesizers and Beam Controllers 208 can convert the digital message/data from the Waveform Generator 207 into individual analog waveforms that can make up a coherent analog wideband composite waveform. In some implementations, the method 250 can include a process 255 to amplify the individual analog waveforms that can make up a coherent analog wideband composite waveform. For example, each analog waveform and/or wideband composite waveform can be amplified by an array element in the Output Amplifier 209. The amplified analog wideband composite waveform can then pass through the T/R Switch 210 and excite its respective array element of the Transducer Array 211, e.g., in an ultrasound probe. The method 250 includes a process 256 to transduce the composite analog waveform to an acoustic waveform that can propagate throughout the scanned volume. For example, each element of the Transducer Array 211 can provide an acoustic waveform from each of the individual analog waveform corresponding to the frequency chip generated in the Waveform Synthesizer and Beam Controller 208 that makes up the wideband composite acoustic waveform. The Transducer Array 211 can form the acoustic beam that propagates into the target medium, e.g., biological tissue volume under study. At the end of the process 256, the method 250 can implement a process 257 to enable receive mode of the SAU System 200 or 200a. For example, when implementing the SAU System 200, the process 257 can switch the SAU System 200 in receive mode by utilizing the System Controller 202 to command the N-pole double-throw T/R Switch 210 to receive position. The method 250 includes a process 258 to receive a returned acoustic waveform, which can be in the form of one or more returned acoustic waveforms. The process 258 can also include transducing the returned acoustic waveform echo(es) into individual received analog waveforms, e.g., corresponding to the frequency chips of the generated individual waveforms. For example, the returned acoustic waveform propagates back to and is received by Transducer Array 211. Each element of Transducer Array 211 can convert the received acoustic waveform it receives into an analog signal (waveform).

In some implementations of the method 250, the Transducer Array 211 can be translated to another position relative to the target. The processes 253-258 can be repeated for each of a plurality of positions of the Transducer Array 211 about the target to form a synthetic aperture, as exemplified in FIG. 2C. In some implementations of the method 250, the Transducer Array 211 can be used to steer the transmitted acoustic waveforms transmitted from one or more positions of the plurality of positions, e.g., which can be at one or more of the corresponding transducer elements of the Transducer Array 211, to form the synthetic aperture, as exemplified in FIG. 2D. For example, the transmitted acoustic waveforms can be steered based on the produced synthetic aperture image, at one or more positions of the plurality of positions in a direct path toward the target. Also, for example, the System Controller 202 can generate for each waveform of the plurality of coded waveforms a plurality of amplitudes and a plurality of phases that are individually amplitude weighted and individually phase weighted, respectively, thereby providing the steering of the acoustic waveform from the position toward the target.

In some implementations, the method 250 can include a process 259 to amplify the individual received analog waveforms. For example, each received analog waveform can be amplified by its respective low noise pre-amplifier element in Pre-Amplifier Module 212. The method 250 includes a process 260 to convert the individual received analog waveforms into digital waveform data. For example, each received (and amplified) analog waveform signal can be converted into a digital word by each respective A/D element in A/D Converter module 213. The digital format data can be sent to the Digital Signal Processor 204 for signal processing.

The method 250 includes a process 261 to process the digital waveform data into a synthetic aperture image and image frames representative of the target medium. The process 261 is explained further detail later in FIG. 6. The process 261 can also include compositing the digital waveform data into a composite digital signal representing the individual and composite received analog waveform. For example, the Digital Signal Processor 204 can detect the amplitude and phase of each of the frequency chips that comprise the wideband composite acoustic waveform received by each of the transducer array elements for the synthetic aperture. The Digital Signal Processor 204 can form the received beam and separate the amplitude and Doppler components of each resolution element of the beam, and can form an image frame associated with mode previously selected by operator. The image frame formed by the Digital Signal Processor 204 can be displayed on Display 205 to the user.

The SAU System 200 can be implemented to produce spread-spectrum, wide instantaneous bandwidth (e.g., up to 100% or more of fractional bandwidth), coherent, pseudo-random noise (PRN), frequency- and/or phase-coded waveforms for ultrasound imaging. There are limitless embodiments of such waveforms. One example is featured in FIG. 3, which shows an exemplary plot of a generated Composite Waveform 300 that is comprised of a plurality of individual waveforms (e.g., frequency chips). In some implementations, the individual waveforms of the Composite Waveform 300 can be PRN waveforms including a sequence of pulses for each frequency chip that repeats itself after a sequence or code period (T), e.g., such that the sequence has a very low correlation with any other sequence in the set of frequency chips, or with the same sequence at a significantly different time frame, or with narrow band interference or thermal noise. For example, the SAU System 200 can generate exactly the same sequences of the exemplary PRN waveforms at both the transmitter and the receiver ends, so a received signal sequence (based on the transmitted signal sequence) can exhibit a high correlation for signal processing to produce an acoustic image of the target.

Figure 3:
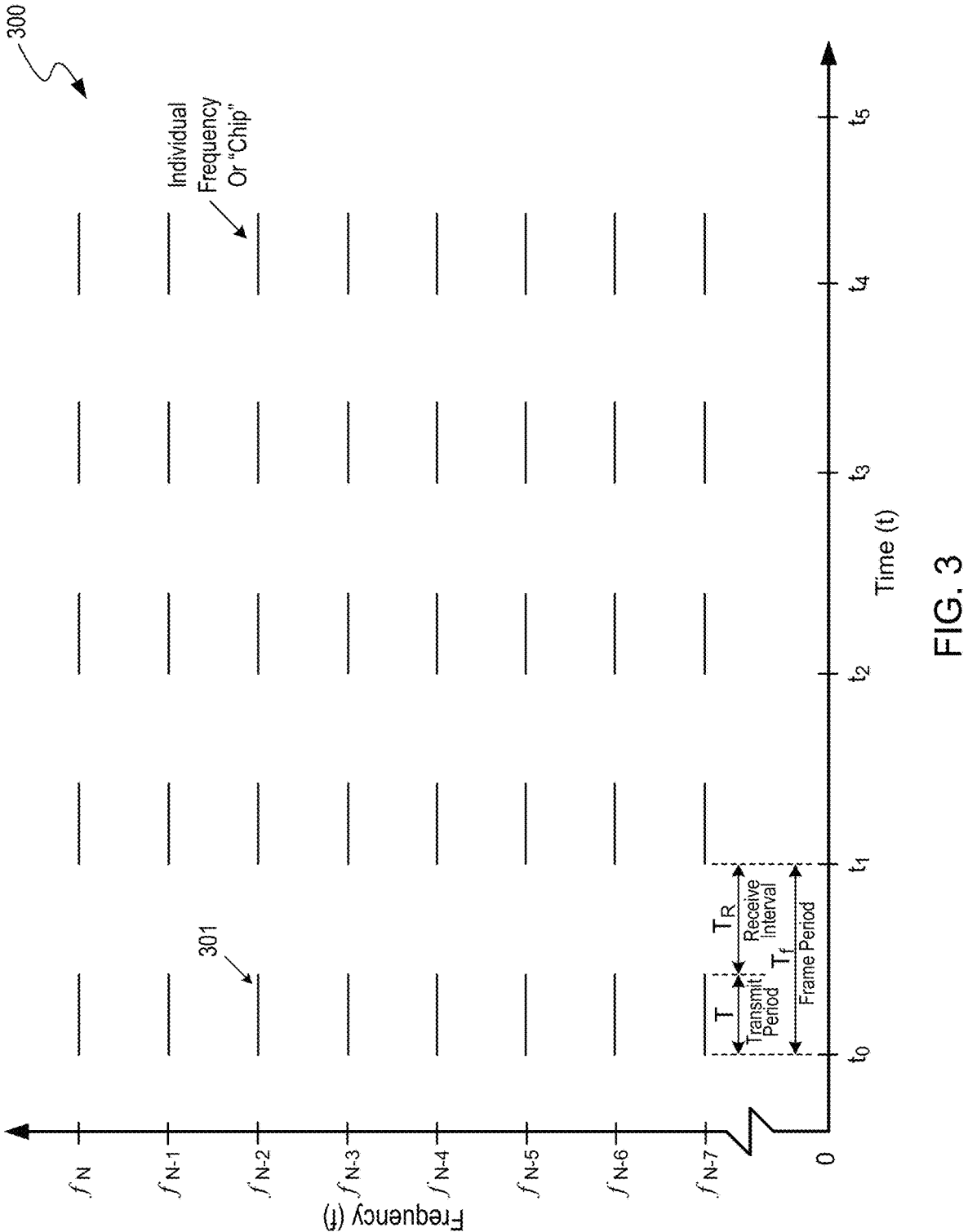
FIG. 3 shows a graph of an exemplary spread-spectrum, wide instantaneous bandwidth, frequency- and/or phase-coded composite waveform featuring a plurality of waveforms.

As shown in FIG. 3, an exemplary individual waveform or Chip 301 of the Composite Waveform 300 corresponds to the frequency chip $f_{N-2}$ that is transmitted during a transmit period T beginning at time frame to, e.g., as described in the process 256 in FIG. 2E. As shown in FIG. 3, following the transmit period T, a receive time interval TR is exhibited, in which returned acoustic waveform echoes are received as described in the process 258 in FIG. 2E. The transmit period T and the receive time interval TR form a frame period $T_f$, which can be repeated in subsequent time frames ($t_1$, $t_2$, $t_3$, . . . ).

The exemplary Composite Waveform 300 can be represented by an equation for waveform, W, which can be represented in the time domain as a complex number, given by Equation (1):

$$W(t) = \sum_k \sum_n^M A_n e^{j(2\pi n f_0 t + \Phi_{nk} + C_n)} U(t - kT_f) \tag{1}$$

W is comprised of M individual orthogonal waveforms (e.g., orthogonal frequency chips), where $j = -\sqrt{-1}$. In Equation (1), n represents the number of frequency chips in the composite waveform W; k represents the number of changes in time (e.g., frames); T represents the chip duration or period of the coded sequence; and $f_0$ represents the fundamental chip frequency, such that $f_0 = 1/NT$, and in which $Nf_0$ is the maximum frequency and $(M-N+1)f_0$ is the minimum frequency. For example, the number of frequency chips n represents a sequence of positive integers from N−M+1 to N. The waveform repetition frequency is $1/T_f$, with $T_f$ being the duration of a frame or epoch, and U(x)=1 for $0 \le x \le T_f$. $\Phi_{nk}$ represents the frequency chip phase term of the $n^{th}$ chip in the $k^{th}$ time epoch, and $A_n$ is the amplitude of the $n^{th}$ chip. For example, the frequency chip phase term $\Phi_{nk}$ can be a pseudo-random phase term, in which a pseudo-randomly scrambled starting phase $\Phi_{nk}$ is a random number in the set $\{I_{nk} 2\pi/N\}$, where Ink is a sequence of random, positive integers selected without replacement from the series I=0, 1, 2, 3, . . . . N, with N being a large number. In another example, the frequency chip phase term $\Phi_{nk}$ can be selected using any one of a number of numerical techniques to produce sets of waveforms $W_s(t)$ that are statistically orthogonal to each other to the degree desired. $C_n$, which is an additive phase term, is a number between 0 and $2\pi$. For example, the frequency chip phase pseudo-random values Ink can be pre-stored in an exemplary database within a memory unit of System Controller 202 and/or Waveform Generator 207.

The composite waveform, W, can be formed by synthesizing individual, substantially orthogonal, coded waveforms (e.g., frequency chips), in which each individual coded waveform corresponds to a distinct frequency band, and the coded waveforms includes at least one of frequency-coded waveforms or phase-coded waveforms, e.g., the coded waveforms synthesized in the Waveform Synthesizers 208. The composite coded waveforms can be synthesized as frequency-coded waveforms by selecting two or more frequencies that define the carrier frequencies of the frequency chips (e.g., including selecting the minimum and maximum frequency) and determining the $A_n$ amplitude values of the frequency chips. The synthesis of the frequency-coded waveforms can also include determining a time-bandwidth product $(Mf_0 T)$ parameter of each waveform of the coded waveforms. In some implementations, the amplitude for a particular frequency chip can be determined as a single value for that frequency chip during a particular time epoch and repeated in subsequent time epochs for the particular frequency chip. In other implementations, the amplitude for a particular frequency chip can be determined as a single value for that frequency chip during a particular time epoch and assigned a different single value in subsequent time epochs for the particular frequency chip. And in other implementations, the amplitude for a particular frequency chip can be determined to include multiple amplitude values for that frequency chip during a particular time epoch, in which the multiple values of the $A_n$ can be repeated or varied in subsequent time epochs for the particular frequency chip. The selection of the range of frequencies from the maximum frequency ($Nf_0$) to the minimum frequency (($M-N+1)f_0$) plus the set of individual waveform amplitude terms ($A_n$) can utilize one of many known code sequences (e.g. including pushing sequences, Barker Codes, etc.) or, for example, utilize a numerical search on pseudo-random codes or any other codes for minimum ambiguity sidelobes.

The composite coded waveforms can additionally or alternatively be synthesized as phase-coded waveforms by determining individual waveform phase terms ($\Phi_{nk}$) of each waveform of the individual coded, orthogonal waveforms (e.g., frequency chips). For example, to provide variation of the composite waveform, W, the phase $\Phi_{nk}$ can include one or more phase values for a frequency chip within the transmit period T. In some implementations, the phase $\Phi_{nk}$ for a particular frequency chip can be determined as a single value for that frequency chip during a particular time epoch and repeated in subsequent time epochs for the particular frequency chip. In other implementations, the phase $\Phi_{nk}$ for a particular frequency chip can be determined as a single value for that frequency chip during a particular time epoch and assigned a different single value in subsequent time epochs for the particular frequency chip. And in other implementations, the phase $\Phi_{nk}$ for a particular frequency chip can be determined to include multiple values for that frequency chip during a particular time epoch, in which the multiple values of the Ink can be repeated or varied in subsequent time epochs for the particular frequency chip. For example, the waveform 301 in the first time epoch ($t_0$) can include a first phase $\Phi_A$, for example, as its phase shift for the beginning portion of the transmit period T and a second phase $\Phi_B$, for example, as its phase shift for the latter portion of the transmit period T. The waveform 301 in the next time epoch ($t_1$) can repeat the exemplary phases $\Phi_A$ and $\Phi_B$ as its beginning and latter phase shifts or include another phase shift sequence (e.g., such as $\Phi_A$, $\Phi_B$, $\Phi_C$, or such as $\Phi_B$ and $\Phi_A$, or other configurations). The synthesis of the frequency-coded can also include determining a time-bandwidth product ($Mf_0T$) parameter of each waveform of the coded waveforms.

$A_n$ exemplary transmitted composite waveform, W, can be comprised of the set of M individual waveforms that are orthogonal and completely span the frequency range $f_{N-M+1}$ to $f_N$, as shown in FIG. 3. The parameter N can be chosen to be a large number to give W a wide instantaneous bandwidth. In the special case when the lowest frequency $f_{N-M+1}=1/T$, then W can describe any wideband waveform that may be contained within this range of frequencies. For any waveform among the M individual waveforms, one or more phases (e.g., $\Phi_{nk}$) can be encoded in a single waveform during the interval T. Additionally, any waveform among the M individual waveforms can include multiple amplitudes encoded in a single waveform. This can be implemented by amplitude weighting and phase weighting.

The family of individual, mutually orthogonal, waveform chips described by Equation (1) can form a coherent, pseudo-random noise, frequency- and/or phase-coded, spread-spectrum composite waveform. Based on the selection of parameters, the individual waveforms can be made to be statistically orthogonal to each other, to any degree desired. For example, the delay and frequency sidelobe levels of the ambiguity function, described in Equation (2), for a given waveform represents the degree of orthogonality of that waveform. By determining particular parameters of the waveforms, medical ultrasound image resolution can be significantly improved. For example, parameters that affect the resolution of medical ultrasound images include the time-bandwidth product ($Mf_0T$) parameter, which determines the inherent combined axial range (e.g., Doppler resolution) and the speckle reduction ability of the waveform, and the individual waveform phase terms ($\Phi_{nk}$), which determine the statistical degree of orthogonality, e.g., which in turn determines the degree that the waveform can function in inhomogeneous media of biological tissues. For example, the lower the sidelobes, the greater the orthogonality and greater the resolution (less noise). The selection of the set of individual waveform phase terms ($\Phi_{nk}$) can utilize one of many known code sequences (e.g. including Barker, Frank, Golay, etc.) or, for example, utilize a numerical search on pseudo-random codes or any other codes for minimum ambiguity sidelobes.

In some implementations, the Composite Waveform 300, described by Equation (1), which for example can be a single-wideband, coherent, frequency- and/or phase-coded waveform. For example, based on the selection of parameters, the single waveform can be made to be statistically orthogonal to any other signal waveform or noise signal present in the target medium.

The parameter $A_n$, which is the amplitude of the $n^{th}$ chip, and $C_n$, which is an additive phase term, in combination can provide pre-emphasis of the analog signal that excites each individual element of Transducer Array 211 to produce a transmitted acoustic waveform that has the desired amplitude and phase characteristics over the frequency range of W. Pre-emphasis of the transmitted waveform can compensate for both the non-constant amplitude and phase response of transducer elements as a function of frequency, and the non-uniform propagation characteristics of intervening tissue layers. For example, the pre-emphasis terms can provide an acoustic waveform that has equal amplitude chips with constant (e.g., flat) amplitude and a known phase versus frequency characteristic. Such constant amplitude versus frequency acoustic waveforms can be referred to as 'white' waveforms. Alternatively, if pre-emphasis is not provided, then the transmitted acoustic waveform can replicate the frequency response of the transducer, and such waveforms are referred to as 'colored' waveforms. De-emphasis of the received waveform can permit determination of the reflection characteristic of the target medium's volume, e.g., biological tissue volume.

The composite waveform W, as described by Equation (1), is an aggregate of two or more individual, mutually orthogonal, coded waveforms, which also may be referred to as chips. Each individual, mutually orthogonal, coded waveform of the composite waveform has a unique frequency with a corresponding specific phase that is associated with each unique frequency. In some implementations, the individual, mutually orthogonal, coded waveforms can be amplitude- and phase-coded, where each unique frequency waveform includes a corresponding specific phase and amplitude associated with each unique frequency. In implementations, for example, the individual, mutually orthogonal, coded waveforms of the composite waveform W can be transmitted sequentially or simultaneously transmitted toward a target, or in some implementations, can be randomly transmitted toward the target.

In one illustrative example, a composite waveform $W$/includes five individual coded waveforms orthogonal to one another: a first waveform comprising a frequency $f_1$ with a corresponding specific phase $\varphi_1$, a second waveform comprising a frequency $f_2$ with a corresponding specific phase $\varphi_2$, a third waveform comprising a frequency $f_3$ with a corresponding specific phase $\varphi_3$, a fourth waveform comprising a frequency $f_4$ with a corresponding specific phase $\varphi_4$, and a fifth waveform comprising a frequency $f_5$ with a corresponding specific phase $\varphi_5$, which can be represented as:

$$W_1 = f_1, \varphi_1 + f_2, \varphi_2 + f_3, \varphi_3 + f_4, \varphi_4 + f_5, \varphi_5.$$

Similarly, for example, a composite waveform $W_2$ having five individual orthogonal coded waveforms can include a first waveform comprising a frequency $f_1$ with a corresponding specific phase $\varphi_6$, a second waveform comprising a frequency $f_2$ with a corresponding specific phase $\varphi_7$, a third waveform comprising a frequency $f_3$ with a corresponding specific phase $\varphi_8$, a fourth waveform comprising a frequency $f_4$ with a corresponding specific phase $\varphi_9$, and a fifth waveform comprising a frequency $f_5$ with a corresponding specific phase $\varphi_{10}$, which can be represented as:

$$W_2 = f_1, \varphi_6 + f_2, \varphi_7 + f_3, \varphi_8 + f_4, \varphi_9 + f_5, \varphi_{10}.$$

Similarly, for example, a composite waveform $W_3$ having five individual orthogonal coded waveforms can include a first waveform comprising a frequency $f_6$ with a corresponding specific phase $\varphi_6$, a second waveform comprising a frequency $f_7$ with a corresponding specific phase $\varphi_7$, a third waveform comprising a frequency $f_5$ with a corresponding specific phase $\varphi_8$, a fourth waveform comprising a frequency $f_9$ with a corresponding specific phase $\varphi_9$, and a fifth waveform comprising a frequency $f_{10}$ with a corresponding specific phase $\varphi_{10}$, which can be represented as:

$$W_3 = f_6, \varphi_6 + f_7, \varphi_7 + f_8, \varphi_8 + f_9, \varphi_9 + f_{10}, \varphi_{10}.$$

Similarly, for example, a composite waveform $W_4$ having five individual orthogonal coded waveforms can include a first waveform (e.g., same as the first waveform in $W_1$) comprising the frequency $f_1$ with a corresponding specific phase $\varphi_1$, a second waveform (e.g., same as the second waveform in $W_1$) comprising a frequency $f_2$ with a corresponding specific phase $\varphi_2$, a third waveform comprising a frequency $f_8$ with a corresponding specific phase $\varphi_{11}$, a fourth waveform (e.g., same as the third waveform in $W_2$) comprising the frequency $f_3$ with a corresponding specific phase $\varphi_8$, and a fifth waveform (e.g., same as the fifth waveform in $W_3$) comprising the frequency $f_{10}$ with a corresponding specific phase $\varphi_{10}$, which can be represented as:

$$W_4 = f_1, \varphi_1 + f_2, \varphi_2 + f_8, \varphi_{11} + f_3, \varphi_8 + f_{10}, \varphi_{10}.$$

Similarly, for example, a composite waveform $W_s$ having five individual orthogonal coded waveforms can include a first waveform comprising the frequency $f_1$ with a corresponding specific phase $\varphi_{12}$, a second waveform comprising a frequency $f_2$ with a corresponding specific phase $\varphi_{12}$, a third waveform comprising a frequency $f_8$ with a corresponding specific phase $\varphi_{12}$, a fourth waveform comprising the frequency $f_3$ with a corresponding specific phase $\varphi_{12}$, and a fifth waveform (e.g., same as the fifth waveform in $W_3$) comprising the frequency $f_{10}$ with a corresponding specific phase $\varphi_{10}$, which can be represented as:

$$W_5 = f_1, \varphi_{12} + f_2, \varphi_{12} + f_8, \varphi_{12} + f_3, \varphi_{12} + f_{10}, \varphi_{10}.$$

All of these exemplary composite waveforms ($W_1$, $W_2$, $W_3$, $W_4$, $W_5$) in this example can be orthogonal to each other or can be designed to have as low of a cross-correlation as desired.

In another illustrative example, a composite waveform $W_6$ includes five individual coded waveforms orthogonal to one another: a first waveform comprising a frequency $f_1$ with a corresponding specific phase $\varphi_1$ and amplitude $A_1$, a second waveform comprising a frequency $f_2$ with a corresponding specific phase $\varphi_2$ and amplitude $A_2$, a third waveform comprising a frequency $f_3$ with a corresponding specific phase $\varphi_3$ and amplitude $A_3$, a fourth waveform comprising a frequency $f_4$ with a corresponding specific phase $\varphi_4$ and amplitude $A_4$, and a fifth waveform comprising a frequency $f_5$ with a corresponding specific phase $\varphi_5$ and amplitude $A_5$, which can be represented as:

$$W_6 = (f_1, \varphi_1, A_1) + (f_2, \varphi_2, A_2) + (f_3, \varphi_3, A_3) + (f_4, \varphi_4, A_4) + (f_5, \varphi_5, A_5).$$

Similarly, for example, a composite waveform $W_7$ having five individual orthogonal coded waveforms can include a first waveform comprising a frequency $f_1$ with a corresponding specific phase $\varphi_6$ and amplitude $A_6$, a second waveform comprising a frequency $f_2$ with a corresponding specific phase $\varphi_7$ and amplitude $A_7$, a third waveform comprising a frequency $f_3$ with a corresponding specific phase $\varphi_8$ and amplitude As, a fourth waveform comprising a frequency $f_4$ with a corresponding specific phase $\varphi_9$ and amplitude $A_9$, and a fifth waveform comprising a frequency $f_5$ with a corresponding specific phase $\varphi_{10}$ and amplitude $A_{10}$, which can be represented as:

$$W_7 = (f_1, \varphi_6, A_6) + (f_2, \varphi_7, A_7) +$$
$$(f_3, \varphi_8, A_8) + (f_4, \varphi_9, A_9) + (f_5, \varphi_{10}, A_{10}).$$

Similarly, for example, a composite waveform $W_s$ having five individual orthogonal coded waveforms can include a first waveform comprising a frequency $f_6$ with a corresponding specific phase $\varphi_6$ and amplitude $A_6$, a second waveform comprising a frequency $f_7$ with a corresponding specific

23 phase $\varphi_7$ and amplitude $A_7$, a third waveform comprising a frequency $f_5$ with a specific phase $\varphi_8$ and amplitude As, a fourth waveform comprising a frequency $f_9$ with a corresponding specific phase $\varphi_9$ and amplitude $A_9$, and a fifth waveform comprising a frequency $f_{10}$ with a corresponding specific phase $\varphi_{10}$ and amplitude $A_{10}$, which can be represented as:

$$W_8 = (f_6, \varphi_6, A_6) + (f_7, \varphi_7, A_7) +$$
$$(f_8, \varphi_8, A_8) + (f_9, \varphi_9, A_9) + (f_{10}, \varphi_{10}, A_{10}).$$

Similarly, for example, a composite waveform $W_9$ having five individual orthogonal coded waveforms can include a first waveform (e.g., same as the first waveform in $W_6$) comprising the frequency $f_1$ with a corresponding specific phase $\varphi_1$ and amplitude $A_1$, a second waveform (e.g., same as the second waveform in $W_6$) comprising a frequency $f_2$ with a corresponding specific phase $\varphi_2$ and amplitude $A_2$, a third waveform comprising a frequency $f_5$ with a corresponding specific phase Qu and amplitude $A_{11}$, a fourth waveform (e.g., same as the third waveform in $W_7$) comprising the frequency $f_3$ with a corresponding specific phase $\varphi_8$ and amplitude As, and a fifth waveform (e.g., same as the fifth waveform in $W_s$) comprising the frequency $f_{10}$ with a corresponding specific phase $\varphi_{10}$ and amplitude $A_{10}$, which can be represented as:

$$W_9 = (f_1, \varphi_1, A_1) + (f_2, \varphi_2, A_2) +$$
$$(f_8, \varphi_{11}, A_{11}) + (f_3, \varphi_8, A_8) + (f_{10}, \varphi_{10}, A_{10}).$$

All of these exemplary composite waveforms ($W_6$, $W_7$, $W_8$, $W_9$) in this example can be orthogonal to each other or can be designed to have as low of a cross-correlation as desired.

By inspection, single frequency modes (e.g., Conventional A-, B- and C-Mode), due to their monochromatic nature, do not need pre-emphasis. Such single frequency waveforms may require amplitude control, for example, to ensure biologically safe sound intensity limits.

If the phase of each chip is random, the transmitted waveform, W, can have random noise-like characteristics. If the phases ($\Phi_{nk}+C_n$) of each chip are uniquely determined, repeatable and synchronized to the Master Clock (as shown in FIG. 2A), the transmitted waveform, W, can be classified as pseudo-random noise. Such pseudo-random noise waveforms are coherent permitting implementation of coherent receivers.

Image processing advantages of wide instantaneous bandwidth, pseudo-random noise waveforms can include reduction, with proper waveform selection, and potential elimination of speckle, e.g., speckles/speckle patterns, which are random intensity patterns produced by the mutual interference waveforms, which are commonly associated with conventional medical ultrasound images. This exemplary reduction in speckle can be an analogous comparison of a scene illuminated by wide band, Gaussian noise-like white light, which has no observable speckle to narrow band laser illumination with exhibits strong speckle of the same scene.

Signal processing advantages of coherent, pseudo-random noise, frequency- and phase-coded waveforms can include waveforms having very low time and Doppler sidelobes. For example, an ambiguity function, $A(\tau,\upsilon)$, can be a two-dimensional representation that shows the distortion of a received waveform processed by a matched filter in the receiver due to the effect of Doppler shift ($\upsilon$) or propagation delay ($\tau$). Specifically, the exemplary ambiguity function $A(\tau,\upsilon)$ is defined by Equation (2) and is determined solely by the waveform properties and the receiver characteristics and not by the scenario. The ambiguity function of $A(\tau,\upsilon)$ is defined by $$A(\tau, \upsilon) = \int_{-\infty}^{+\infty} X_a(t)X_b^*(t-\tau)\, e^{j2\pi\upsilon t} \tag{2}$$

where $$X_k(t) = \frac{1}{\sqrt{T}} e^{j[2\pi f_k(t-t_k)+\Phi_k]},$$

for $0 \le t \le T$, $X_k(t)=0$ otherwise.

For waveforms of the type described by Equation (1), the following equation can be obtained:

$$A(\tau, \upsilon, t, f_n, \Phi_n, f_m, \Phi_m, T) = \tag{3}$$
$$\left(1 - \frac{|\tau - (\Delta t)|}{T}\right) \frac{\mathrm{Sin}\,[2\pi(\Delta f)\,(T-|\Delta t|)]}{[2\pi(\Delta f)\,(T-|\Delta t|)]} e^{j2\pi[\Delta f(T+\Delta t)-f_n^{\Delta t+\upsilon t}+\Delta\Phi]}$$

where $\Delta t=\tau-t$, $\Delta f=\upsilon-(f_n-f_m)$, and $\Delta\Phi=\Phi_n-\Phi_m$, which can result in the complete ambiguity equation shown in Equation (4):

$$x(\tau, \upsilon) = \frac{1}{M} \sum_n \sum_m A(T, \upsilon, t, f_n, \Phi_n, f_m, \Phi_m, T) \tag{4}$$

where both n and m are a sequence of positive integers from N−M+1 to N.

Figure 4:
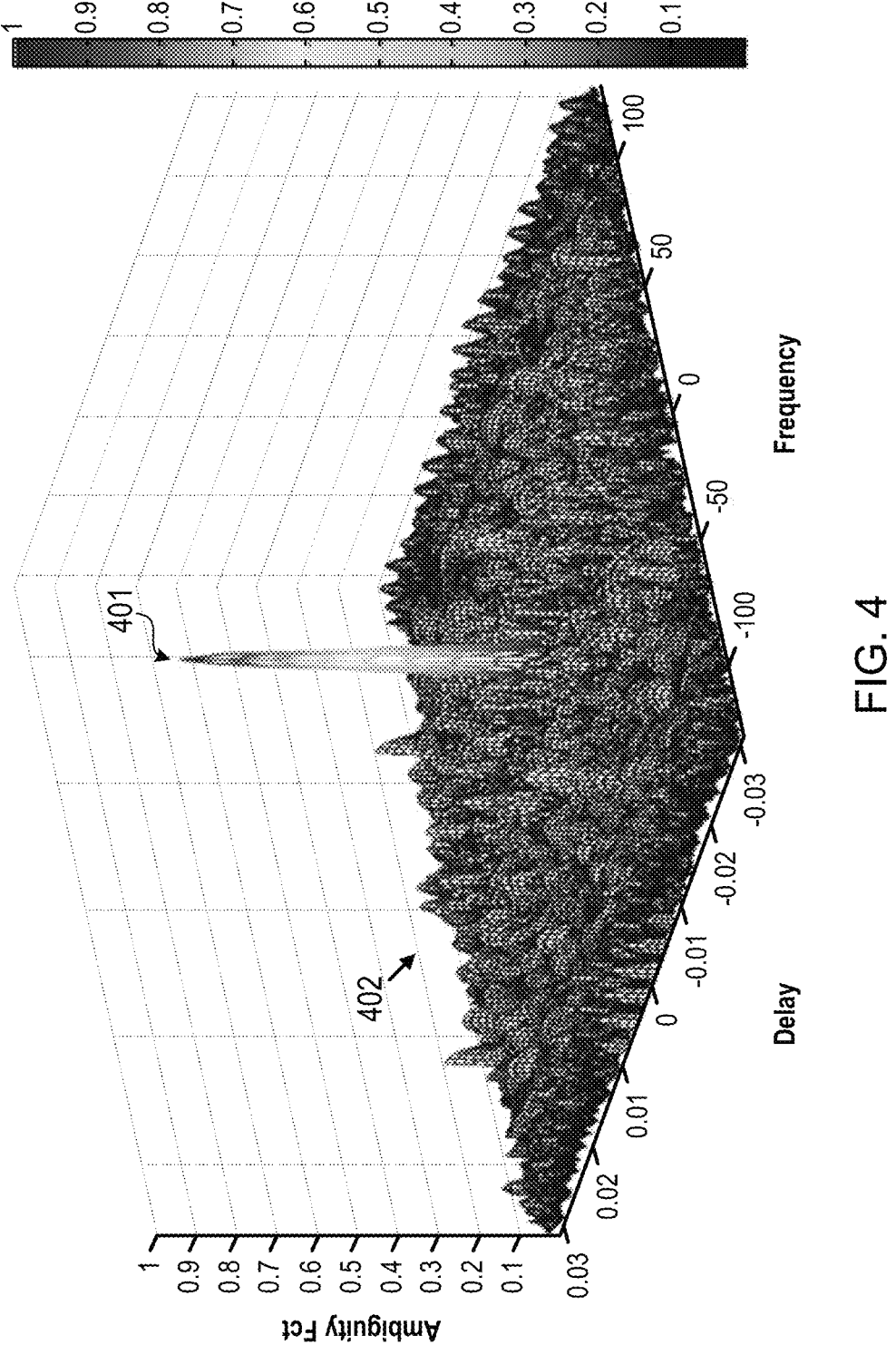
FIG. 4 shows ambiguity function characteristics of an exemplary spread-spectrum coded waveform.

FIG. 4 shows exemplary ambiguity function characteristics of a pseudo-random noise, frequency-coded, composite waveform 401, represented by Equation (1) for waveform, W. The exemplary frequency-coded, composite waveform 401 includes a code length of 128. As shown in FIG. 4, the sidelobes 402 of this ambiguity function are due to chip-to-chip phase interactions and have a plateau level in both delay and frequency below the peak that is a function of $N^2$.

By inspection, many composite waveforms (W) are possible depending on the specific codes ($I_{nk}$) selected. However, the sidelobe performance cannot be guaranteed for every waveform defined, and therefore only those codes which give sufficiently low sidelobes in both delay and frequency as determined by a numerical search of a set of possible codes should be used.

For example, in medical ultrasound applications, living tissue as a propagation medium is inhomogeneous. Propagation medium inhomogeneity can introduce differential time delays, and living tissue can introduce unwanted motion induced Doppler. Ultrasound transducer arrays also can have undesirable side lobes and grating lobes (e.g., due to physical size limitations) in the off-axis portions of ultrasound beam that add unwanted time delay and Doppler returns to the returns of the main lobe. Waveforms that exhibit low ambiguity function sidelobes can significantly improve SAU focusing and target contrast due through the reduction interference from differential time delays, motion-induced Doppler, and transducer side lobe effects.

Coherent pseudo-random noise, frequency- and/or phase-coded waveforms can enable higher-order cross-range focusing techniques to be employed that can improve the lateral resolution of size limited ultrasound transducer arrays, e.g., medical ultrasound transducer arrays.

For example, each biological tissue type and each diseased tissue type may exhibit their own unique ultrasound echo return signals as a function of frequency, mono-static and bi-static angles, and spatial morphology. Using conventional Elastograph-Mode (E-Mode) modalities, it can be difficult to take advantage of such properties to classify tissues, e.g., due to measurement errors such as the inability to accurately characterize the ultrasound wave propagation through overlaying inhomogeneous media. Exemplary waveforms produced by the exemplary SAU System 200, e.g., wide instantaneous bandwidth, coherent pseudo-random noise, frequency- and/or phase-coded waveforms, can enable tissue differentiation by determining the physical tissue features from the echo returns of the target volume under investigation. Classifiers, one example being Bayesian-inference classifiers among others, can be applied to the feature data obtained from the measured characteristics of the received echo to automatically classify tissue types observed in the target volume providing a Computer Aided Diagnostic-Mode (CAD-Mode).

Unlike conventional E-Modes, which inherently have significantly reduced image quality and rely on individual operator technique, the exemplary waveforms described by Equation (1) can inherently provide improved image quality while simultaneously colorizing the resultant image by tissue type in the ATS and/or CAD-Modes. With this advantage, user technique can be mitigated and the margins of a lesion are discernible, thus permitting improved diagnoses.

Figure 5A:
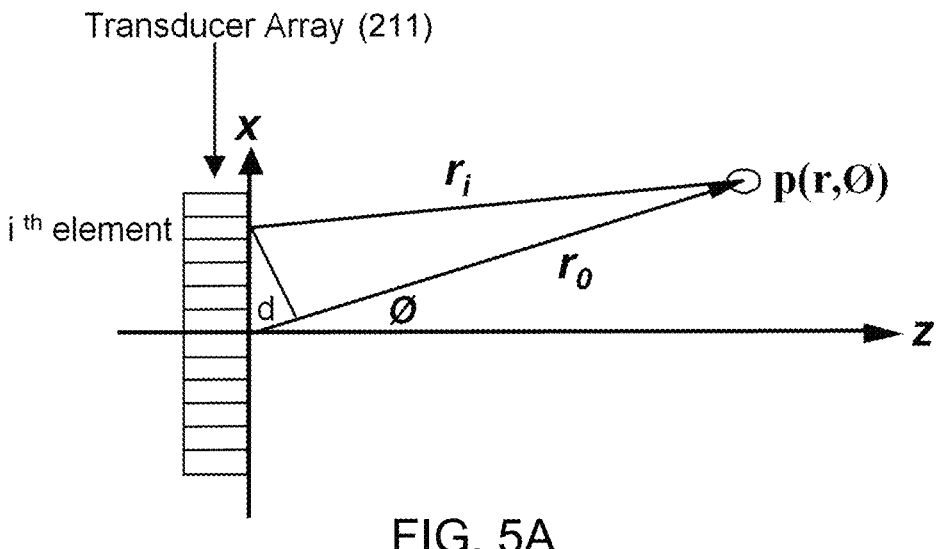
FIGS. 5A-5C show an exemplary diagram for beam steering, dynamic focusing, and forming.
Figure 5B:
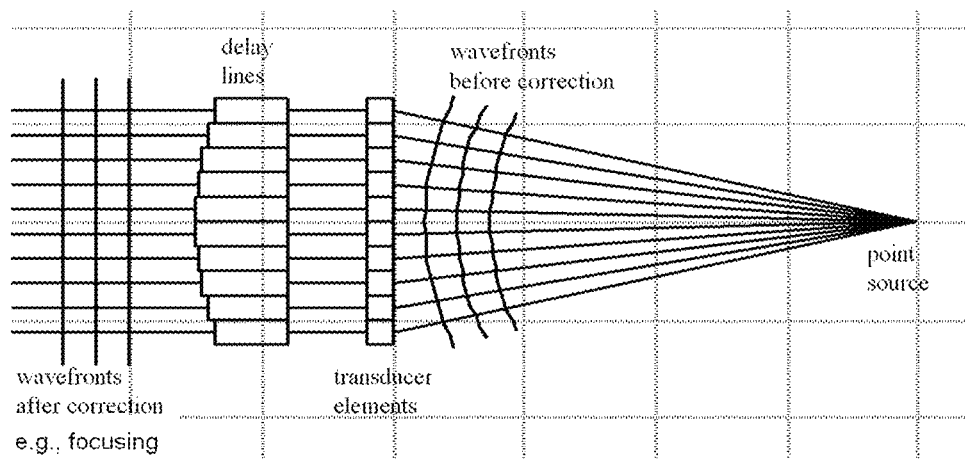
Figure 5C:
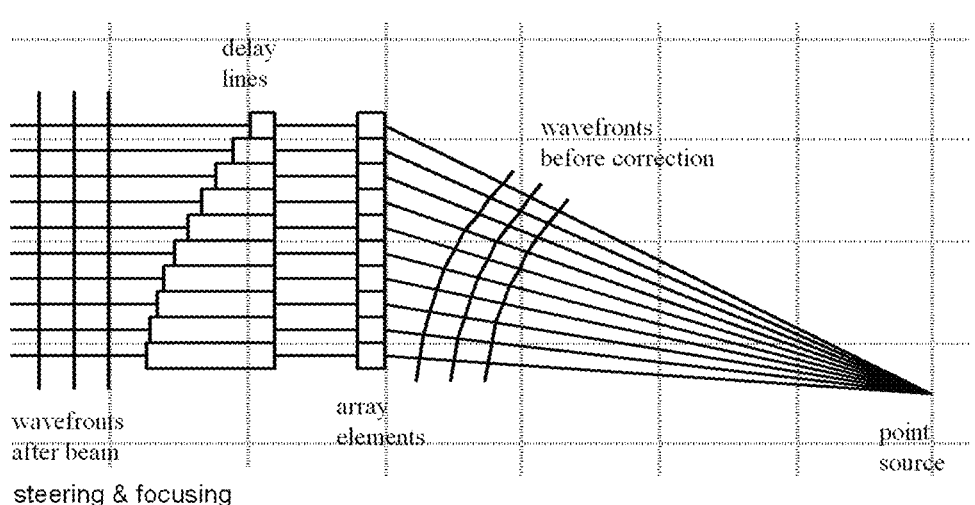

In addition, the Waveform Synthesizers 208 positioned on transmit and the Digital Signal Processor 204 positioned on receive (as shown in FIG. 2A), can also perform beam control (e.g., beam steering, dynamic beam focusing, and beamforming) functions. FIGS. 5A-5C show the basics of these digital electronic functions by introducing a differential time delay, or equivalently a phase shift, and amplitude weighting between each of the elements of the phased array. As can be seen in FIG. 5A, the differential phase shift can compensate for the differential change in distance (d) each acoustic ray ($r_1$, $r_2$, ... $r_i$, ... ) travels from $i^{th}$ element to the point of focus (p). An angle ($\theta$) is formed as the point of focus (p) is not along the z-axis direction of direct aim/alignment of the Transducer Array 211 toward a target in the target medium. Additionally, a differential amplitude weight can be applied to each element to control the beam shape and suppress side and grating lobes. Also, for one or more chips in an exemplary waveform, the Waveform Generator 207 can pre-encode a phase delay to delay the phase of the one or more chips transmitted at each transducer element in the Transducer Array 211. $A_n$ exemplary result of this feature can be seen in FIGS. 5B and 5C. The exemplary phase delay values for the one or more chips can be communicated to the Digital Signal Processor 204 and/or the System Controller 202 to incorporate the phase delay values in the signal processing of the received composite waveform.

For narrow instantaneous bandwidth ultrasound devices, this function can be accomplished by introducing phase shift and amplitude attenuation on the composite analog signal driving each element. However, for the exemplary spread-spectrum, wide instantaneous bandwidth, frequency- and phase-coded waveforms generated by the SAU System 200, each individual chip of the waveform ($W_i$) is individually amplitude weighted ($B_{ni}$) and phase weighted ($D_{ni}$) as a function of frequency (n) for each array element (i) individually for all X elements, as indicated by Equation (5).

$$W_i(t) = \sum_k \sum_n A_n B_{ni} e^{j(2\pi n f_0 t + \Phi_{nk} + C_n + D_{ni})} U(t - kT_f) \qquad (5)$$

On transmit, the amplitude and phase weighting required of each chip can be computed by the System Controller 202 and can be sent as an instruction to the Waveform Generator 207. The Waveform Generator 207 can then send the digital words (real and imaginary components) to the Waveform Synthesizers and the Beam Controller 208 that produces the analog drive signal that is amplified by Amplifier 209 and sent to each element of the array of the Transducer Array 211.

Synthetic aperture ultrasound signal processing includes collecting the received synthetic aperture ultrasound signal data and processing these data by using a sequence of algorithms that utilizes a replica of the transmitted waveform to produce a synthetic aperture ultrasound image. For example, the synthetic aperture ultrasound signal processing of the disclosed technology negates the propagation effects of living inhomogeneous tissue, e.g., by taking advantage of the "thumb-tack" ambiguity function, as shown in FIG. 4. On receive, the A/D Converter module 213 can convert the received analog signal to digital words. The A/D Converter module 213 can send the digital words that represent the amplitude and phase information of each chip for each sampled position of the real array element for each array element to the Digital Signal Processor 204, where the data is collected and stored over the entire synthetic aperture.

The axial resolution (da) of a synthetic aperture waveform is given by the expression $\partial_a = c/B$, where B is the bandwidth of the waveform and c is the speed of sound. The lateral resolution ($\partial_l$) of a real aperture can be approximated by the expression $\partial_l = d\lambda_c/w_R$. The lateral resolution for a synthetic aperture, e.g., formed by the SAU System 200, can be approximated by $\partial_l = d\lambda_c/2W$, where $\lambda_c$ is the wavelength of the center frequency of the transmitted waveform.

Figure 6:
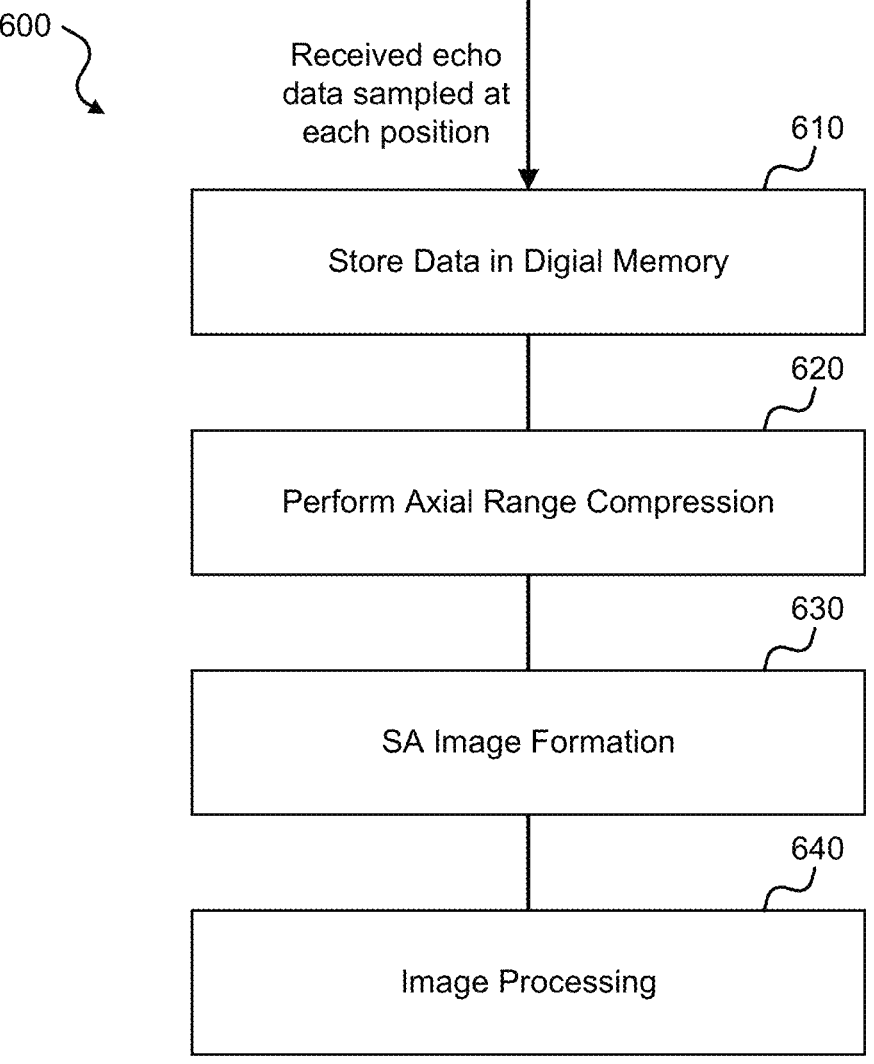
FIG. 6 shows a block diagram of an exemplary synthetic aperture ultrasound signal processing technique to produce an ultrasound image.

FIG. 6 shows a block diagram of an exemplary synthetic aperture ultrasound signal processing technique 600 using digital signal processing to produce an ultrasound image. The technique can be implemented to process exemplary coherent, wideband, instantaneous, spread-spectrum, coded, and noise-like ultrasound waveforms. The exemplary synthetic aperture ultrasound signal processing technique can be implemented using the Digital Signal Processor 204 of the SAU System 200 for the exemplary SASS and SASpl modes, as shown in FIGS. 2C and 2D, respectively. As shown in FIG. 6, the SAU signal processing technique 600 includes a process 610 to store the digital words that represent the amplitude and phase information of each frequency chip of the transmitted ultrasound pulse and the returned echo signals for each sampled position in a memory unit of the SAU System 200. In some implementations, for example, the SAU signal processing technique 600 can include a process 620 to performing axial range compression before the formation of the synthetic aperture, e.g., which can include the benefit of conserving memory. The SAU signal processing technique 600 can include a process 630 to form the synthetic aperture image by processing the stored block of axial-range compressed echo-data that encompass the entire synthetic aperture. The SAU signal processing technique 600 can include a process 640 to process the SA image data to form an ultrasound image for display.

Figure 7:
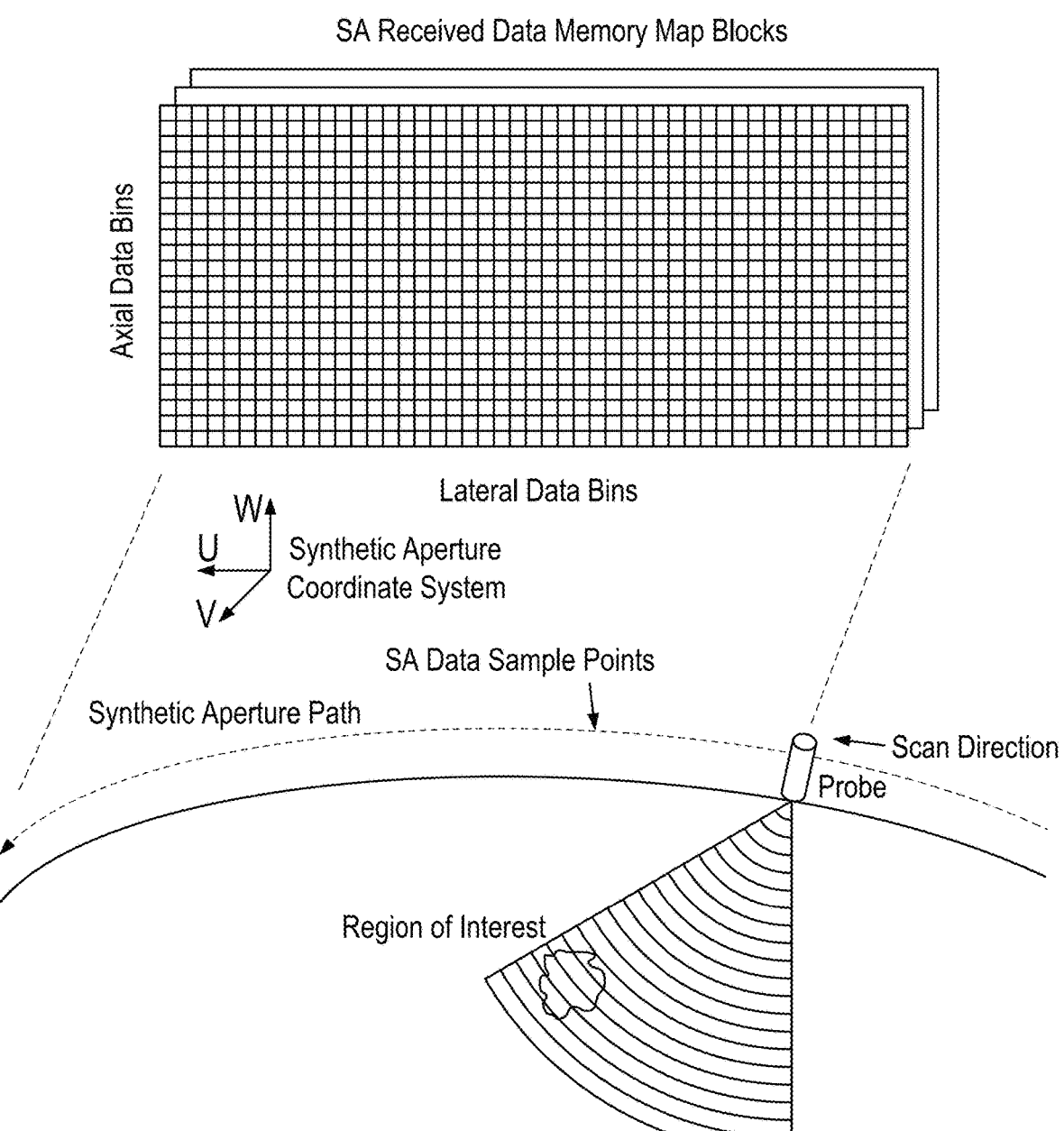
FIG. 7 shows a diagram of exemplary synthetic aperture-sampled received echo data and storage to memory.

FIG. 7 shows a diagram of exemplary synthetic aperture-sampled received echo data and storage to memory. In this exemplary SAU data collection scenario, the transducer sub-array phase center, which may be referred to simply as a probe, is translated either mechanically, or electronically as portion of a larger array, in the SA coordinate system shown along an arbitrary, but known, open or closed 3D path, in the general case, sampling raw echo-return data at each u,v,w data point, and for each θ, φ beam angle. The digitized received-echo data for each sample point and its 3D position are stored in a block of memory for each complete scan. As shown in the process 610 of FIG. 6, the received, digitized, echo returns are collected and stored in memory. FIG. 7 shows a conceptual diagram of an exemplary synthetic aperture received data memory map of the stored blocks of data. The collected digitized received-echo data can be processed as a block of data on a block-by-block basis.

Figure 8:
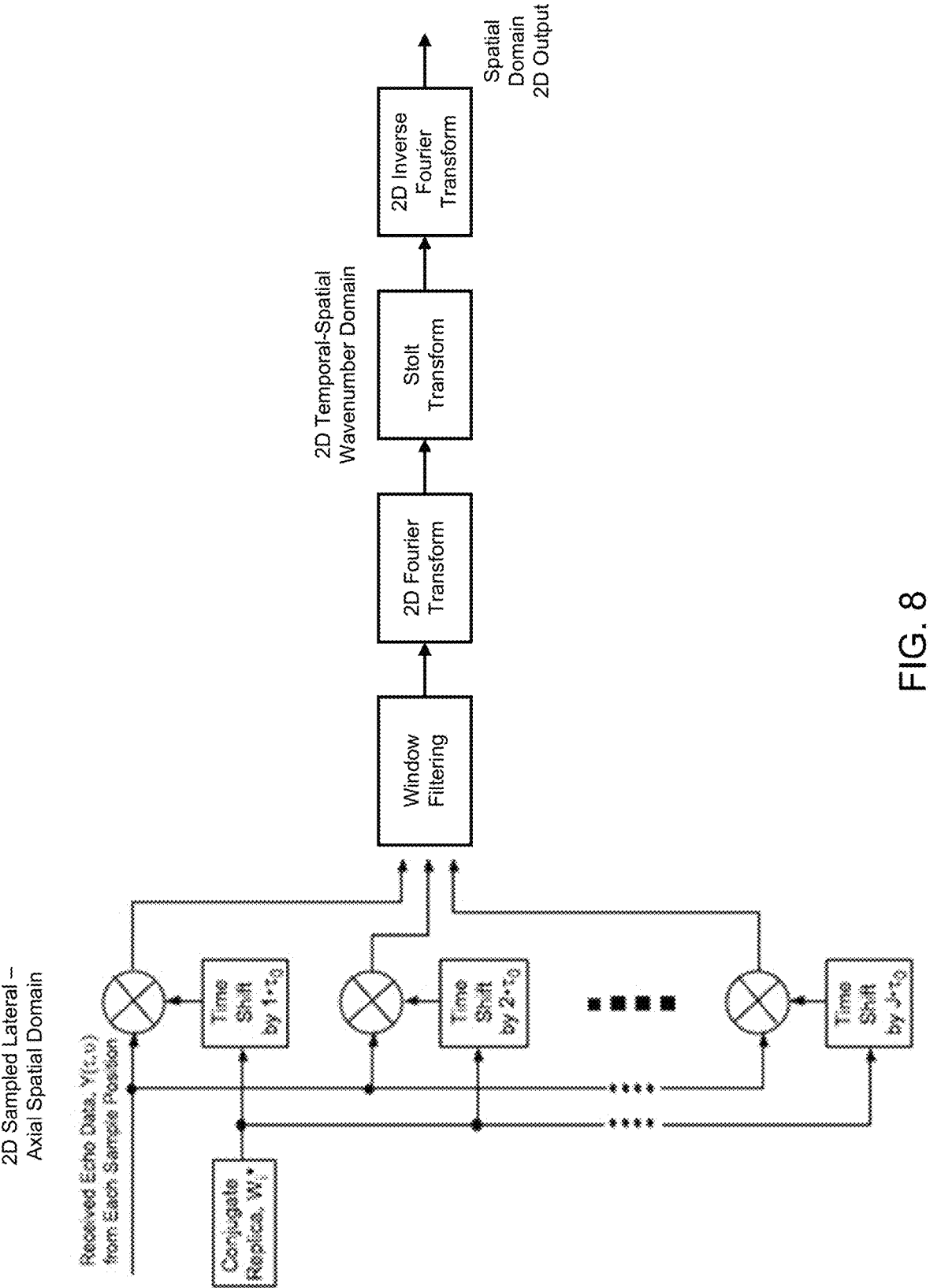
FIG. 8 shows a block diagram of an exemplary wave-number algorithm for wideband, spread-spectrum, noise-like, coherent synthetic aperture image formation.

The process 620 to perform axial range compression, e.g., using the Digital Signal Processor 204 of the SAU System 200, can be implemented according to the following example. FIG. 8 shows a block diagram of an exemplary wave-number algorithm for wideband, spread-spectrum, noise-like, coherent synthetic aperture image formation. In this example, the received signal, $Y_i(\tau,\upsilon)$, for each data collection sample point, can be multiplied by the complex conjugate replica of the transmitted digital waveform, $W_i^*$ $(\tau)$ that is shifted in time $t_0$. This multiplication operation can be repeated J times, e.g., typically in parallel; but for each operation, the waveform replica is shifted in time by an integral increment, $j \cdot t_0$, from the previous one, as shown in FIG. 8, and stored in memory based on the sampled data point in the exemplary memory map, as shown in FIG. 7. This step is repeated for each of the sampled data points, producing the compressed axial-range data for the axial-range slices, j, shown in the FIGS. 2C and 2D.

The process 630 to form the synthetic aperture image, e.g., using the Digital Signal Processor 204 of the SAU System 200, can be implemented using any of several different sets of algorithms. For example, these sets of synthetic aperture algorithms may be classified as either frequency domain algorithms or as time domain algorithms. For example, types of frequency-domain algorithms can include wave-number algorithms, chirp-scaling algorithms, and scaled inverse-Fourier-transform algorithms, among others. For example, types of time-domain algorithms can include explicit matched-filter algorithms, and back-projection algorithms, among others. While all of these exemplary algorithms are applicable to forming synthetic aperture coherent, wide instantaneous bandwidth, spread-spectrum, medical ultrasound images, the frequency domain wave-number algorithm is provided as an example shown in FIG. 8, e.g., as the wave-number algorithm may be conceptually the easiest to understand.

The process 630 can include a window-filtering step of the produced compressed axial-range data, as shown in FIG. 8. For example, to minimize spectral leakage due to the discontinuities at the extremities of finite-duration signal records, window-function filtering can be applied to improve image quality. In this example, for each axial-range slice j, the resultant products are multiplied by a window function, e.g., such as a rectangular, Hann, Hamming, Tukey, Kaiser Bessel, Dolph-Chebyshev, Blackman-Harris, etc. window. These exemplary window functions are tapered to zero at the extremities. The selection of a window function may involve a tradeoff between the suppression of spectral-leakage-induced image sidelobes and image resolution. For example, the more smoothly the window tapers to zero, the lower are the unwanted image sidelobes at the expense of reduced resolution. Conversely, for example, the 'steeper' the function goes to zero at the extremities, the sharper is the resolution at the expense of higher image sidelobes. In one example, a rectangular window function can produce the highest resolution and the highest sidelobes. Alternatively, for example, a Blackman-Harris window function can produce very low sidelobes (e.g. below −70 dB) and lower resolution, e.g., as compared to rectangular window functions. In the process 630, the selection of the specific window function or functions to be implemented may be left to the operator to the operator of the SAU System 200, e.g., since it is examination-dependent.

The process 630 can include a Fourier Transform step of the window-function filtered data, as shown in FIG. 8. In some examples, a two-dimensional, Discrete Fourier Transform (DFT) can be applied to a block of digitized, range-compressed, received-echo data that was previously collected and stored in memory for the entire synthetic aperture. There are many alternative discrete Fourier transform algorithms available for use in the process. Of the exemplary DFT class, a Cooley-Tukey algorithm can be implemented, albeit any of the DFT may suffice. In the process 630, the selection of the Fourier Transform algorithm to be implemented may be left to the operator to the operator of the SAU System 200.

The process 630 can include a Stolt Transform step subsequent to the Fourier Transform step, as shown in FIG. 8. The Stolt Transform can be used for lateral compression of the Fourier-transformed data collected over the total synthetic aperture. For example, the wave-number algorithm basically inverts the imaging system data through a coordinate transformation (Stolt Mapping) through interpolation in the spatial frequency domain. The compressed-echo data, which was converted to the wavenumber domain in the Fourier Transform step, has a matched filtering applied with respect to a target at a synthetic focus range, followed by a coordinate transformation in one step. The Stolt Transform converts the multiple polar data-set samples collected at each point, U, along the synthetic aperture, as illustrated in FIGS. 1B and 2D, to a single image, mapping it to a new X-Y coordinate system, focused at the origin, as shown in FIG. 9.

Figure 9:
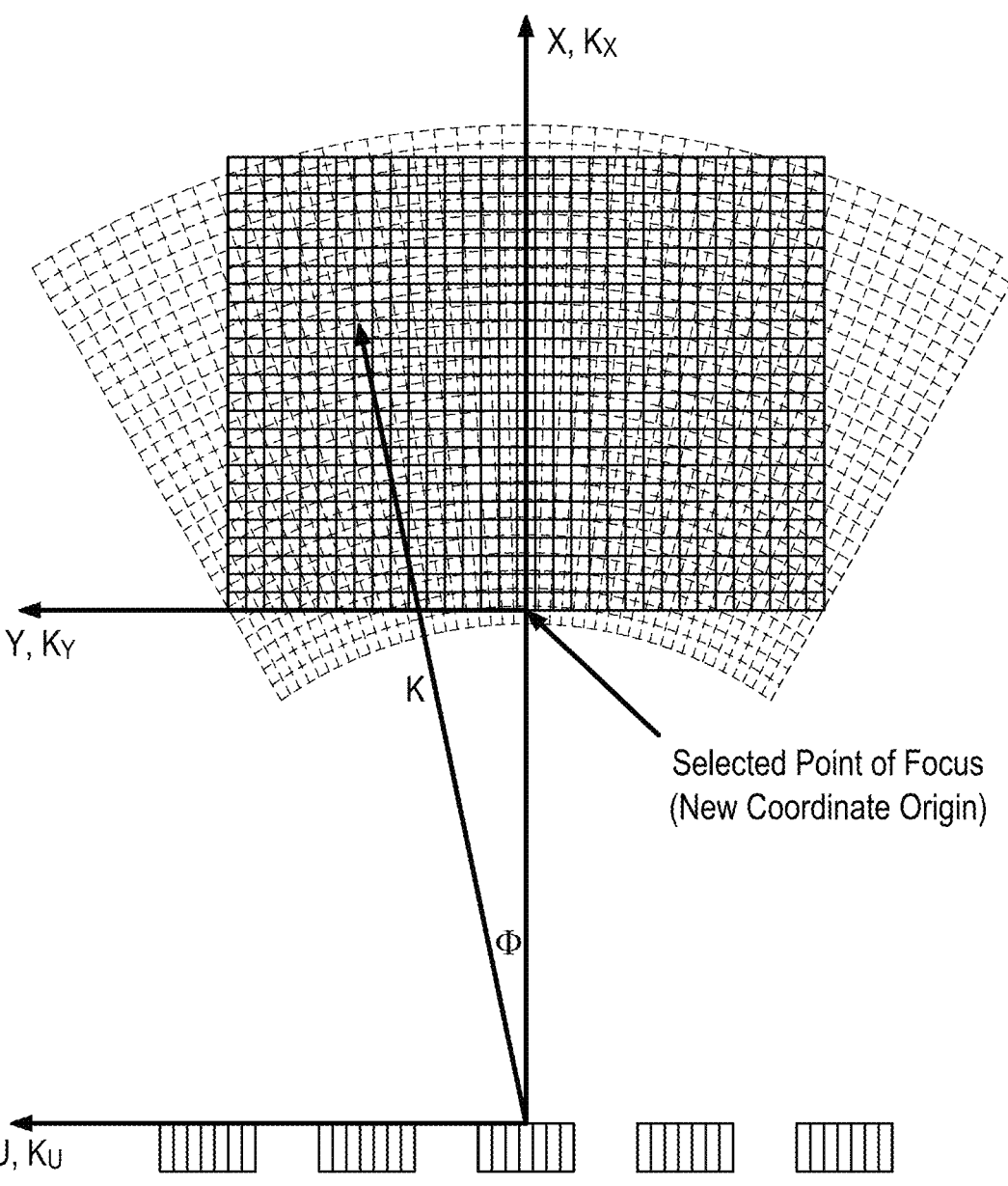
FIG. 9 shows a diagram illustrating an exemplary implementation of the Stolt Transform process.

FIG. 9 shows a diagram illustrating an exemplary implementation of the Stolt Transform process, which converts the multiple-sample image that were collected over the synthetic aperture from polar coordinates to one higher-resolution image in a new coordinate system with an origin at the desired point of focus. For illustrative purposes, it is assumed that the synthetic aperture in this example includes a one-dimensional transducer probe translating along the U axis. Following usual convention, the temporal wavenumber is defined as $K=2\pi f/c$ in the direction of propagation. The spatial wavenumber is defined as $K_U=K \sin \Phi$, where the angle $\Phi$ is given by the following expression:

$$\Phi = \sin^{-1}\left(Y/\sqrt{X^2 + Y^2}\right), \tag{6}$$

which is centered (e.g., focused) on the origin of the X-Y coordinate system. The spatial wavenumbers $K_X$ and $K_Y$ are in the direction of the X and Y axes respectively. For this specific example of the geometry shown in FIG. 9, the Stolt mapping is the following:

$$K_X(f, K_U) = \sqrt{4K^2 - K_U^2} \qquad (7)$$

$$K_Y(f, K_U) = K_U$$

The process 630 can include an Inverse Fourier Transform step subsequent to the Stolt Transform step, as shown in FIG. 8. A two-dimensional, inverse Discrete Fourier Transform can be applied to the results from the previous Stolt Transform step. For example, since the inverse DFT is essentially the same algorithm as the DFT, except for a 1/N factor and an opposite sign in the exponent, like the DFT there are many alternative inverse DFTs that are available for implementation of this step. For example, a commonly used DFT includes the Cooley-Tukey algorithm, but since any of the DFT algorithms can be implemented, but any of the inverse DFT algorithms may suffice. In the process 630, the selection of the Inverse Fourier Transform algorithm to be implemented may be left to the operator to the operator of the SAU System 200.

In some implementations of the process 630, for example, an autofocusing step may be performed. For example, the focusing of a synthetic aperture open-loop formed image may optionally be improved using any number of well-known Synthetic Aperture Radar (SAR) and Synthetic Aperture Sonar (SAS) autofocus algorithms that lower the side-lobes of Point Spread Function (PSF) of the resultant image. Since the received synthetic aperture data is block-processed, those portions of the image away from the point of focus may be imperfectly focused, due to arbitrary phase errors. Implementing one or more autofocus techniques may at least partially correct to improve image quality.

In synthetic aperture image formation, open-loop synthetic aperture digital processing algorithms, such as those described previously, can assume medium homogeneity, stationarity, and precise transmit-and-receive transducer-sampling locations with respect to the scene. For example, the desired level of homogeneity, stationarity and transducer location may not be completely realizable with living mammalian subjects. Therefore, in some exemplary implementations, it may be desirable to form the synthetic aperture image by applying a set of open-loop synthetic aperture algorithms and then apply a global or a series of regional autofocus algorithms taking advantage of the coherent, spread-spectrum nature of the waveforms to improve image quality by lowering the sidelobes of the PSF that are not coherent from aperture sampling point to sampling point. For example, open-loop synthetic aperture algorithms use the best available estimates for transducer sample locations and tissue parameters using the best available estimates for transducer sample locations and tissue parameters, then the autofocus algorithm searches for optimal image quality to refine the image formation parameters, e.g., mitigating estimate imprecision in transducer location, inhomogeneous tissue characteristics, and incoherent PSF sidelobes. Since autofocus techniques rely on coherency and redundancy in the raw data, the received-echo signal preferably can be over-sampled both temporally and spatially than the Nyquist limit, e.g., if significant improvement in image quality is to be realized. For example, the temporal sampling interval can be less than $1/(2Nf_0)$, and the spatial sampling interval can be less than a half wavelength at mid-frequency or $c/[(N+M)f_0]$.

Figure 10:
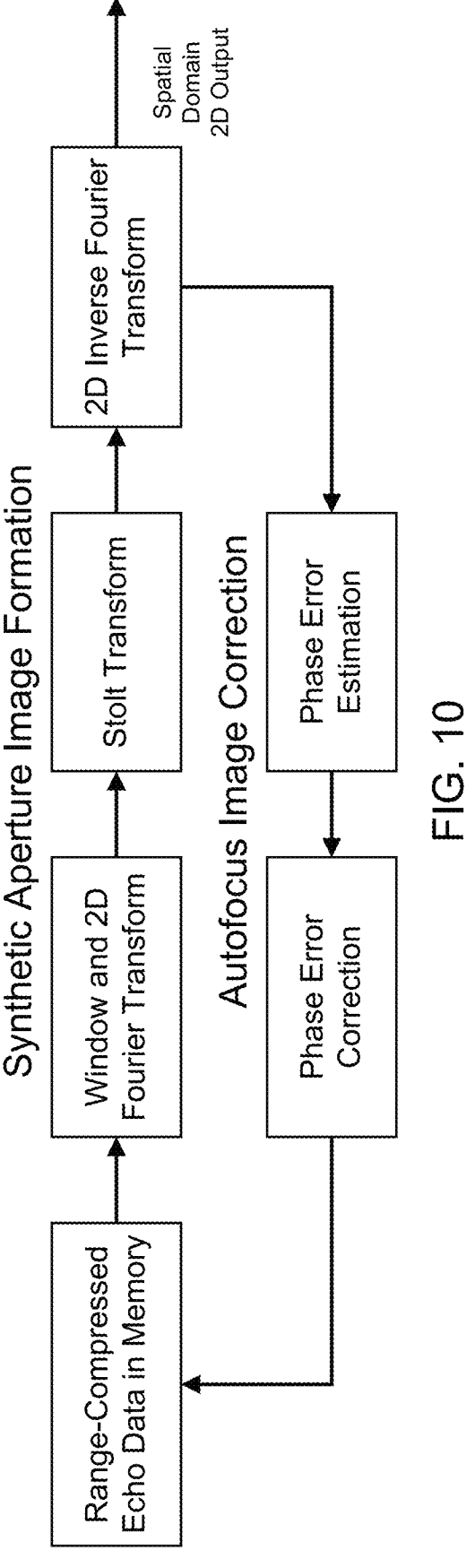
FIG. 10 shows a block diagram of an exemplary iterative, closed-loop, synthetic aperture image autofocus subroutine.

FIG. 10 shows a block diagram of an exemplary coherent, iterative, closed-loop, synthetic aperture image autofocus subroutine. The exemplary coherent, iterative, closed-loop, autofocus image correction process can be implemented to improve the quality of the image compensation for undesirable variations in axial-lateral synthetic aperture phase history, but at the expense of additional digital signal-processing load.

In the exemplary iterative, closed-loop, synthetic aperture image autofocus subroutine of FIG. 10, first, the phase error based on the raw received-echo data is estimated, and then the estimated/incoherent phase errors in these data are removed. For example, depending on the nature and magnitude of the phase errors, they can significantly degrade the image quality in terms of geometry, resolution, contrast and reduced signal-to-noise ratio (SNR), as shown in Table 1, which shows the effect of various types of phase errors on reconstructed images.

TABLE 1

| Type of Error | Phase Error Variation over Entire Synthetic Aperture | Effect on Image |
|---|---|---|
| Slowly Varying (Affects Main Lobe) | Linear | Geometric Displacement |
| | Quadratic | Defocus/Reduced Resolution |
| | Higher Order Polynomial | Distortion |
| Rapidly Varying (Affects Side Lobes) | Sinusoidal | Image Artifacts |
| | Random Wideband Incoherent Noise | Reduced Contrast & SNR |

While there are many well-known autofocus algorithms, they can be grouped, in general, into either non-parametric, or model-based, or a combination of the two types. For example, one commonly-used non-parametric algorithms includes the phase-gradient algorithm, which exhibits an ability to remove higher order phase errors over a variety of scenes. In addition, there are several algorithms that have been developed that are enhancements to the phase-gradient algorithm. For example, the eigenvector algorithm, which is a maximum-likelihood estimator, and the weighted least-square algorithm that minimizes the variance of the phase error, are two examples from among many.

Model-based, autofocus algorithms employ a model of the systematic, position-dependent, slowly varying, phase errors present in every physical measurement system. For example, a device-dependent, sampling position error model is developed for the mechanical elements of the transducer scanning assembly. Given such a model, the phase errors are estimated and phase error corrections are iterated until the best image is obtained based on some predetermined quality metric.

One example of a hybrid non-parametric, model-based approach is to segment the image into sub-images using an error model of the scanning system, such that the phase errors present on each sub-image are position invariant. A non-parametric autofocus algorithm, e.g., such as the phase-gradient algorithm, can then be applied individually to each sub-image. Lastly, for example, the individual sub-images are reassembled together to form a complete autofocused image.

One of the advantages of the coherent, broadband waveform of Equation 5 is that the received signal may be segmented into sub-bands and the lowest frequency (e.g., longest wavelength) sub-band may be selected first for phase-error estimation. This longest wavelength sub-band effectively has the least impact of phase errors, e.g., due to the inhomogeneous tissue and sampling position uncertainties, as compared to the higher frequency (shorter wavelength) sub-bands. Upon achieving a predefined level of image quality, e.g., by employing a selected autofocus algorithm such as the phase gradient algorithm, selected and progressively shorter wavelength sub-band data may be used for further refine the estimate of the phase errors present, if desired. Lastly, for example the phase-corrected sub-band data are reassembled to form a complete autofocused image.

Several applications and uses of the disclosed technology can be implemented to exploit the described features of the aforementioned systems, methods, and devices. Some examples are described for clinical use of the disclosed technology.

In one exemplary application, the resultant image quality, and the ATS and CAD modes of an exemplary spread-spectrum ultrasound device can enable the primary care physician to incorporate this modality into a routine examination screening protocol to locate early stage malignancies (e.g., Stage 0 or 1), as well as later stage cancers. As the result of this application, the device can potentially, for example, enhance the survival rate of hard-to-diagnose asymptomatic patients suffering from malignancies, e.g., such as stomach, pancreatic, bladder cancers, etc.

In another exemplary application, the resultant image quality, ATS and CAD modes of an exemplary spread-spectrum ultrasound device can permit board-certified radiologists to diagnose neoplasms as benign or malignant prior to any surgical biopsy or resection intervention. As a result of this application, the ability of radiologists to locate and diagnose early stage malignancies (e.g., Stage 0 or 1) can potentially improve patient survival rate. Additionally, unnecessary biopsies potentially can be avoided, along with their attendant risk of hard-to-treat or even lethal complications such as, for example, methicillin-resistant *Staphylococcus aureus* (MRSA staph) infections.

In another exemplary application, the resultant 2D or 3D image quality of an exemplary spread-spectrum ultrasound device and, optionally, its 4D imaging capability (e.g., which can be derived from the sequential storage of 3D images) can be used in fine needle biopsy and other medical procedures. For example, the exemplary spread-spectrum ultrasound device can be integrated into an exemplary fine-needle biopsy instrument (e.g., with the device's transducer probe), which can permit the fine-needle biopsy of very small, early stage (e.g., Stage 0 or 1) neoplasms to confirm noninvasive diagnoses. As a result of this application, the ability of surgeons to avoid open biopsies and the potential for hard-to-treat and lethal complications that may result is clearly beneficial to the patient.

In another exemplary application, the integration of this device's spread-spectrum transducer probe with minimally invasive surgical high definition video instrumentation can permit the fusing of the optical and ultrasound images. Given the improved 2D or 3D image quality of this spread-spectrum ultrasound device, optionally, its 4D imaging capability, and the ATS and CAD modes, such fused video and ultrasound images can give surgeons the added ability to locate and surgically excise diseased tissue without excising excessive healthy tissue.

In another exemplary application, the integration of this device's spread-spectrum, 2D or 3D high-definition imaging mode of operation, with this device's HIFU minimally invasive mode of operation, can permit the precision minimally invasive surgical therapeutic options. Given the improved 2D or 3D image quality of this spread-spectrum ultrasound device, optionally, and its 4D imaging capability, and the ATS and CAD modes, such ultrasound images can give surgeons the added ability to locate and surgically destroy diseased tissue with rapid heat elevation without destroying excessive healthy tissue.

In another exemplary application, given the improved 3D image quality of this spread-spectrum ultrasound device, optionally, its 4D imaging capability, and the ATS modes, an exemplary spread-spectrum ultrasound device can reduce the amount of time for the brachytherapy treatment of malignant neoplasms by precisely guiding the insertion of catheters and sealed radioactive sources into the proper location. The application of this spread-spectrum ultrasound device to brachytherapy can be especially useful for the treatment of small, hard-to-locate neoplasms and their margins.

In another exemplary application, given the improved 3D image quality of this spread-spectrum ultrasound device, optionally, its 4D imaging capability, and the ATS modes, an exemplary spread-spectrum ultrasound device can enable the effective insertion of high-dose, localized pharmaceutical treatments of diseases by precisely guiding the insertion of catheters and pharmaceuticals into the proper location. The application of this spread-spectrum ultrasound device to brachytherapy can be especially useful for the treatment of small, hard-to-locate neoplasms.

EXAMPLES

The following examples are illustrative of several embodiments of the present technology. Other exemplary embodiments of the present technology may be presented prior to the following listed examples, or after the following listed examples.

In one example of the present technology (example 1), a method of producing acoustic waveforms in an acoustic imaging device includes synthesizing, in one or more waveform synthesizers, one or more composite waveforms to be transmitted toward a target, in which a composite waveform is formed of a plurality of individual orthogonal coded waveforms that are mutually orthogonal to each other and correspond to different frequency bands, such that each of the individual orthogonal coded waveforms includes a unique frequency with a corresponding phase; transmitting, from one or more transmitting positions relative to the target, one or more composite acoustic waveforms including a plurality of acoustic waveforms, in which the transmitting includes selecting one or more transducing elements of an array to transduce the plurality of individual orthogonal coded waveforms of the respective one or more composite waveforms into the plurality of corresponding acoustic waveforms of the respective one or more composite acoustic waveforms; and receiving, at one or more receiving positions relative to the target, returned acoustic waveforms that are returned from at least part of the target corresponding to the transmitted acoustic waveforms, in which the receiving includes selecting at least some of the transducing elements of the array to receive the returned acoustic waveforms, in which the transmitting positions and the receiving positions each include one or both of spatial positions of an array of transducer elements relative to the target and beam phase center positions of the array, and in which the transmitted acoustic waveforms and the returned acoustic waveforms produce an enlarged effective aperture of the acoustic imaging device.

Example 2 includes the method of example 1, in which, in transmitting the acoustic waveforms to the target, controlling the transducer elements of the array to cause the composite waveforms to change in orientation with respect to the target so that the target receives the acoustic waveforms at different waveform orientations over an imaging period.

Example 3 includes the method of example 2, in which the controlling the transducer elements includes translating the array along the plurality of spatial positions relative to the target to cause the change in orientation of the composite waveform with respect to the target.

Example 4 includes the method of example 2, in which the controlling the transducer elements includes changing the beam phase center positions of the transmitted acoustic waveforms on the one or more transducer elements of the array to cause the change in orientation of the composite waveform with respect to the target.

Example 5 includes the method of example 1, in which each waveform of the plurality of individual orthogonal coded waveforms includes a plurality of amplitudes and a plurality of phases that are individually amplitude weighted and individually phase weighted, respectively.

Example 6 includes the method of example 1, in which the synthesizing the individual orthogonal coded waveforms of the composite waveform includes selecting the frequency bands, and determining one or more amplitudes, a time-bandwidth product parameter, and a phase parameter of each individual orthogonal coded waveform.

Example 7 includes the method of example 6, in which the phase parameter is determined from a set of a pseudo-random numbers or from a set of deterministic numbers.

Example 8 includes the method of example 1, in which the transmitting the plurality of the acoustic waveforms includes sequentially or simultaneously transmitting the acoustic waveforms from at least one position of the plurality of positions.

Example 9 includes the method of example 1, in which the individual orthogonal coded waveforms include coherent waveforms.

Example 10 includes the method of example 1, further including forming a radio frequency (RF) waveform based on the composite waveform, in which in the transmitted acoustic waveforms are generated by transducing the RF-based composite waveform at the one or more transducer elements of the array.

Example 11 includes the method of example 10, further including amplifying the RF-based composite waveform.

Example 12 includes the method of example 1, further including amplifying the received returned acoustic waveforms.

Example 13 includes the method of example 1, further including converting the received returned acoustic waveforms from analog format to digital format as one or more received composite waveforms corresponding to the one or more composite waveforms, each received composite waveform including information of the target, in which the information includes an amplitude and a phase associated with the corresponding frequency bands of the received composite waveform.

Example 14 includes the method of example 13, in which at least one of the amplitude or the phase is individually amplitude weighted or phase weighted, respectively, for at least one frequency band of the corresponding frequency bands of the received composite waveform.

Example 15 includes the method of example 1, further including processing the received returned acoustic waveforms to produce an image of at least part of the target.

Example 16 includes the method of example 15, further including converting the received returned acoustic waveforms from analog format to digital format as one or more received composite waveforms corresponding to the one or more composite waveforms, each received composite waveform including information of the target; and storing the one or more composite waveforms and the corresponding one or more received composite waveforms in a memory map of data blocks, in which each data block stores the received returned acoustic waveform of the composite waveform for each sample point, the corresponding individual orthogonal coded waveform, and corresponding position data of the one or more transducer elements for the sample point.

Example 17 includes the method of example 15, in which the processing includes performing axial range compression of the stored received composite waveforms; and forming a synthetic aperture image by processing each stored block of axial-range compressed data that encompass the effective aperture using one or more frequency- or time-domain processing techniques.

In one example of the present technology (example 18), a synthetic aperture acoustic waveform imaging system includes a waveform generation unit including one or more waveform synthesizers coupled to a waveform generator, in which the waveform generation unit synthesizes a composite waveform including a plurality of individual orthogonal coded waveforms corresponding to different frequency bands that are generated by the one or more waveform synthesizers according to waveform information provided by the waveform generator, in which the individual orthogonal coded waveforms are mutually orthogonal to each other and correspond to different frequency bands, such that each of the individual orthogonal coded waveforms includes a unique frequency with a corresponding phase; a transmit/receive switching unit that switches between a transmit mode and a receive mode; an array of transducer elements in communication with the transmit/receive switching unit to transmit a composite acoustic waveform including a plurality of acoustic waveforms from one or more transmitting positions relative to the target, the transmitted acoustic waveforms of the composite acoustic waveform based on the synthesized individual orthogonal coded waveforms of the composite waveform, and to receive at one or more receiving positions relative to the target returned acoustic waveforms corresponding to the plurality of transmitted acoustic waveforms that return from at least part of the target, in which the transmitted acoustic waveforms and the returned acoustic waveforms produce an enlarged effective aperture of the synthetic aperture acoustic waveform imaging system, and in which the transmitting positions and the receiving positions each include one or both of spatial positions and beam phase center positions; a multiplexing unit in communication with the array of transducer elements to select one or more transducing elements of an array to transduce the plurality of individual orthogonal coded waveforms into the plurality of corresponding acoustic waveforms, and to select one or more transducing elements of the array to receive the returned acoustic waveforms; an array of analog to digital (A/D) converters to convert the received returned acoustic waveforms that are received by the array of transducer elements from analog format to digital format, in which the received returned acoustic waveforms provide information of the target; a controller unit in communication with the waveform generation unit and the array of A/D converters, the controller unit including a memory unit to store data and a processing unit coupled to the memory unit to process the information as data; and a user interface unit in communication with the controller unit.

Example 19 includes the system of example 18, in which the stored data includes the digital format of the received returned acoustic waveforms, the corresponding synthesized composite waveform, and corresponding position data of the array of transducers elements in the one or more transmitting and receiving positions.

Example 20 includes the system of example 18, in which the waveform generation unit further includes one or more amplifiers, configured between the transmit/receive switching unit and the one or more waveform synthesizers, which modifies the composite waveform.

Example 21 includes the system of example 18, further including an array of one or more pre-amplifiers, configured between the transmit/receive switching unit and the array of A/D converters, which modifies the received returned acoustic waveform.

Example 22 includes the system of example 18, in which the processing unit includes a digital signal processor.

Example 23 includes the system of example 18, in which the controller unit further includes a master clock that synchronizes time in at least one of the elements of the acoustic waveform imaging system.

Example 24 includes the system of example 18, in which the controller unit is configured to process the information to produce an image of at least part of the target.

Example 25 includes the system of example 18, in which the user interface unit includes a display that displays the image and a user input terminal to receive user input data including a mode of operation for operation of the system.

Example 26 includes the system of example 25, in which the mode of operation includes at least one of ATS-Mode (Artificial Tissue Staining Mode) for imaging biological tissue that enables image color coding based on at least one feature of one or more measured properties that are obtained from the returned acoustic waveform.

Example 27 includes the system of example 25, in which the mode of operation includes at least one of CAD-Mode (Computer Aided Diagnostic Mode) for imaging biological tissue that uses one or more algorithmic classifiers to classify biological tissue types using at least one feature of one or more measured properties that are obtained from the returned acoustic waveform.

Example 28 includes the system of example 25, in which the display is configured to display a color coded image of the biological tissue based on the classified biological tissue types.

Example 29 includes the system of example 18, in which, in transmitting the acoustic waveforms to the target, the controller unit is configured to control the array of transducer elements to cause the composite waveform to change in orientation with respect to the target so that the target receives the composite acoustic waveform with different waveform orientations over an imaging period.

Example 30 includes the system of example 18, in which the array of transducer elements is operable for moving in one dimension, two dimensions, or three dimensions along the transmitting positions to transmit the plurality of acoustic waveforms and along the receiving positions to receive the returned acoustic waveforms.

Example 31 includes the system of example 18, in which at least one of the transducer elements of the array is capable of moving separately in the one dimension, two dimensions, or three dimensions from the other transducer elements of the transmitter array.

In one example of the present technology (example 32), a method of creating an image from an acoustic waveform includes combining a plurality of coded waveforms corresponding to different frequency bands to produce a composite waveform including individual orthogonal wave signals at the different frequency bands, in which the coded waveforms include a unique frequency with a corresponding phase and amplitude; producing an acoustic wave using the composite waveform for transmission toward a target from a first spatial position relative to the target, in which the acoustic wave includes individual acoustic wave signals corresponding to the coded waveforms of the composite waveform; transmitting the acoustic wave to the target, in which the individual acoustic wave signals vary in orientation with respect to each other so that the target receives the individual acoustic wave signals with different waveform orientations over an imaging period; receiving returned acoustic signals from at least part of the target after the transmitted acoustic wave is sent to the target; repeating the combining step, the producing step, and the transmitting step from at least a second position relative to the target, in which the combining, producing, and transmitting steps are repeated for plurality of positions to form a synthetic aperture; converting the received returned acoustic signals from the plurality of positions into corresponding digital composite waveforms each including information of the target; and processing the received composite waveforms to produce an image of at least part of the target.

Example 33 includes the method of example 32, further including processing the received composite waveforms in real time to produce a synthetic aperture image.

Example 34 includes the method of example 33, further including steering a direction of the transmitted acoustic waves, based on the produced synthetic aperture image, at one or more positions of the plurality of positions in a direct path toward the target.

In one example of the present technology (example 35), a method of creating an image from an acoustic waveform includes combining a plurality of coded waveforms corresponding to different frequency bands to produce a composite waveform including individual orthogonal wave signals at the different frequency bands, in which the coded waveforms include a unique frequency with a corresponding phase and amplitude; producing an acoustic wave formed of individual acoustic wave signals corresponding to the coded waveforms of the composite waveform for transmission toward a target; transmitting the acoustic wave to the target, in which the individual acoustic wave signals are transmitted from a first set of beam phase center positions at one or more spatial positions relative to the target, and in which the individual acoustic wave signals vary in orientation with respect to each other so that the target receives the individual acoustic wave signals with different waveform orientations over an imaging period; receiving returned acoustic signals from at least part of the target after the transmitted acoustic wave is sent to the target; repeating the combining step, the producing step, and the transmitting step from at least a second set of beam phase center positions relative to the target at the one or more spatial positions relative to the target, thereby forming a synthetic aperture; converting the received returned acoustic signals into corresponding digital composite waveforms each including information of the target; and processing the received composite waveforms to produce an image of at least part of the target.

Example 36 includes the method of example 35, further including processing the received composite waveforms in real time to produce a synthetic aperture image.

Example 37 includes the method of example 36, further including steering a direction the transmitted acoustic waves based on the produced synthetic aperture image.

In one example of the present technology (example 38), a synthetic aperture acoustic waveform imaging system includes a waveform generation unit including one or more waveform synthesizers coupled to a waveform generator, in which the waveform generation unit synthesizes a composite waveform including a plurality of individual orthogonal coded waveforms corresponding to different frequency bands that are generated by the one or more waveform synthesizers according to waveform information provided by the waveform generator, in which the individual orthogonal coded waveforms are mutually orthogonal to each other and correspond to different frequency bands, such that each of the individual orthogonal coded waveforms includes a unique frequency with a corresponding phase; a transmitter array of transducer elements in communication with the waveform generation unit to transmit a composite acoustic waveform including a plurality of acoustic waveforms from one or more transmitting positions relative to the target, the transmitted acoustic waveforms of the composite acoustic waveform based on the synthesized individual orthogonal coded waveforms of the composite waveform, in which the transmitting positions include one or both of spatial positions of the transmitter array and beam phase center positions of the transducer elements of the transmitter array; a receiver array of transducer elements in communication with the waveform generation unit to receive at one or more receiving positions relative to the target returned acoustic waveforms corresponding to the transmitted acoustic waveforms that return from at least part of the target, in which the transmitted acoustic waveforms and received acoustic waveforms produce an enlarged effective aperture of the synthetic aperture acoustic waveform imaging system, and in which the transmitting positions and the receiving positions each include one or both of spatial positions and beam phase center positions; a first multiplexing unit and a second multiplexing unit in communication with the transmitter array and receiver array, respectively, to select one or more of the transducing elements of the transmitter array to transduce the plurality of individual orthogonal coded waveforms into the plurality of corresponding acoustic waveforms, and to select one or more transducing elements of the receiver array to receive the returned acoustic waveforms; an array of analog to digital (A/D) converters to convert the received returned acoustic waveforms that are received by the receiver array of transducer elements from analog format to digital format, in which the received returned acoustic waveforms provide information of the target; a controller unit in communication with the waveform generation unit and the array of A/D converters, the controller unit including a memory unit to store data and a processing unit coupled to the memory unit to process the information as data; and a user interface unit in communication with the controller unit.

Example 39 includes the system of example 38, in which the stored data includes the digital format of the received returned acoustic waveforms, the corresponding synthesized composite waveform, and corresponding position data of the transmitter array and the receiver array in the one or more transmitting and receiving positions, respectively.

Example 40 includes the system of example 38, in which the waveform generation unit further includes one or more amplifiers, configured between the transmit/receive switching unit and the one or more waveform synthesizers, which modifies the composite waveform.

Example 41 includes the system of example 38, further including an array of one or more pre-amplifiers, configured between the receiving array and the array of A/D converters, which modifies the received returned acoustic waveform.

Example 42 includes the system of example 38, in which the processing unit includes a digital signal processor.

Example 43 includes the system of example 38, in which the controller unit further includes a master clock that synchronizes time in at least one of the elements of the acoustic waveform imaging system.

Example 44 includes the system of example 38, in which the controller unit is configured to process the information to produce an image of at least part of the target.

Example 45 includes the system of example 38, in which the user interface unit includes a display that displays the image and a user input terminal to receive user input data including a mode of operation for operation of the system.

Example 46 includes the system of example 45, in which the mode of operation includes at least one of ATS-Mode (Artificial Tissue Staining Mode) for imaging biological tissue that enables image color coding based on at least one feature of one or more measured properties that are obtained from the returned acoustic waveform.

Example 47 includes the system of example 45, in which the mode of operation includes at least one of CAD-Mode (Computer Aided Diagnostic Mode) for imaging biological tissue that uses one or more algorithmic classifiers to classify biological tissue types using at least one feature of one or more measured properties that are obtained from the returned acoustic waveform.

Example 48 includes the system of example 45, in which the display is configured to display a color coded image of the biological tissue based on the classified biological tissue types.

Example 49 includes the system of example 38, in which, in transmitting the acoustic waveforms to the target, the controller unit is configured to control the transmitter array to cause the composite waveform to change in orientation with respect to the target so that the target receives the composite acoustic waveform with different waveform orientations over an imaging period.

Example 50 includes the system of example 38, in which the transmitter array of transducer elements is operable for moving in one dimension, two dimensions, or three dimensions along the plurality of positions to transmit the plurality of acoustic waveforms.

Example 51 includes the system of example 38, in which one or more transducer elements of the transmitter array is capable of moving separately in the one dimension, two dimensions, or three dimensions from the other transducer elements of the transmitter array.

Example 52 includes the system of example 38, in which the receiver array of transducer elements is operable for moving in one dimension, two dimensions, or three dimensions along the plurality of positions to receive the returned acoustic waveforms.

Example 53 includes the system of example 38, in which one or more transducer elements of the receiver array is capable of moving separately in the one dimension, two dimensions, or three dimensions from the other transducer elements of the transmitter array.

Example 54 includes the system of example 38, in which the number of transducer elements of the transmitter array is greater than the number of transducer elements of the receiver array.

Implementations of the subject matter and the functional operations described in this specification, such as various modules, can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer program products, e.g., one or more modules of computer program instructions encoded on a tangible and non-transitory computer-readable medium for execution by, or to control the operation of, data processing apparatus. The computer-readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special-purpose logic circuitry, e.g., an FPGA (field programmable gate array) or an ASIC (application specific integrated circuit).

Processors suitable for the execution of a computer program include, by way of example, both general and special-purpose microprocessors, such as, for example, digital signal processors (DSP), and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer-readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special-purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is:

1. A system for synthetic aperture acoustic imaging, comprising:

an acoustic imaging device comprising an array of transducer elements, in communication with one or more computing devices, to produce and transmit a composite acoustic beam, based on a composite waveform, toward a material of interest, wherein the composite waveform comprises a plurality of individual coded waveforms, wherein the acoustic imaging device is configured to transmit the composite acoustic beam by selection of one or more of the transducer elements of the array to transduce the plurality of individual coded waveforms of the composite waveform into a plurality of corresponding acoustic waveforms that form the composite acoustic beam, wherein the acoustic imaging device is configured to receive returned acoustic waveforms that are returned from at least part of the material of interest corresponding to at least some transmitted acoustic waveforms that form the composite acoustic beam, wherein transmitted acoustic waveforms and received returned acoustic waveforms create an enlarged effective aperture of the acoustic imaging device.

2. The system of claim 1, wherein the returned acoustic waveforms are received by selection of at least some of the transducer elements of the array to receive the returned acoustic waveforms at one or more receiving positions of the array of transducer elements relative to the material of interest.

3. The system of claim 2, wherein the composite acoustic beam is transmitted from one or more transmitting positions of the array of transducer elements relative to the material of interest.

4. The system of claim 3, wherein one or both of the one or more transmitting positions and the one or more the receiving positions include one or both of (i) spatial positions of the array of transducer elements relative to the material of interest and (ii) beam phase center positions of the array of transducer elements.

5. The system of claim 1, wherein the plurality of individual coded waveforms each correspond to distinct frequency bands, such that each of the individual coded waveforms includes a unique frequency with a corresponding phase.

6. The system of claim 1, wherein at least some of the selected individual coded waveforms that form the composite waveform are individually amplitude weighted, individually phase weighted, or both individually amplitude weighted and individually phase weighted, thereby providing at least one of steering, focus, or forming of the composite acoustic beam.

7. The system of claim 1, wherein the selected individual coded waveforms include frequency-coded waveforms, phase-coded waveforms, or frequency-coded and phase-coded waveforms.

8. The system of claim 1, wherein at least one of the selected individual coded waveforms that form the composite waveform includes two or more amplitudes, two or more phases, or two or more amplitudes and two or more phases.

9. The system of claim 1, further comprising:
  one or more computing devices, comprising a processor and a memory, configured to process the received returned acoustic waveforms to produce a tomographic image containing information of the material of interest based on the received returned acoustic waveforms.

10. The system of claim 9, wherein the tomographic image includes a volume tomographic rendering of the at least part of the material of interest that provides one or more of a sagittal plane view, coronal plane of view, transverse plane of view, or an arbitrary plane of view.

11. The system of claim 9, wherein the one or more computing devices includes a controller unit and a user interface unit in communication with the controller unit, wherein the controller unit is configured to process the received composite waveform to produce the tomographic image of at least part of the material of interest and display the image via the user interface.

12. The system of claim 9, wherein the one or more computing devices is configured to produce the composite waveform from the plurality of individual coded waveforms.

13. The system of claim 12, wherein the one or more computing devices is configured to generate the plurality of individual coded waveforms.

14. The system of claim 12, wherein the one or more computing devices is configured to store the plurality of individual coded waveforms.

* * * * *